US010822396B2

(12) United States Patent
Choe et al.

(10) Patent No.: US 10,822,396 B2
(45) Date of Patent: Nov. 3, 2020

(54) REPEAT-CHAIN FOR THE PRODUCTION OF DIMER, MULTIMER, MULTIMER COMPLEX AND SUPER-COMPLEX

(71) Applicant: MuHyeon Choe, Seoul (KR)

(72) Inventors: MuHyeon Choe, Seoul (KR); YongChan Lee, Asan-si (KR); JaeSeon Won, Seoul (KR)

(73) Assignee: MuHyeon Choe (KR)

(*) Notice: Subject to any disclaimer, the term of this patent is extended or adjusted under 35 U.S.C. 154(b) by 0 days.

(21) Appl. No.: 13/904,824

(22) Filed: May 29, 2013

(65) Prior Publication Data
US 2013/0323717 A1    Dec. 5, 2013

Related U.S. Application Data

(63) Continuation-in-part of application No. 13/516,367, filed as application No. PCT/KR2009/007510 on Dec. 15, 2009, now abandoned.

(51) Int. Cl.
| C07K 16/00 | (2006.01) |
| C07K 14/31 | (2006.01) |
| C07K 14/315 | (2006.01) |
| C12P 21/02 | (2006.01) |
| C07K 14/195 | (2006.01) |
| G01N 33/537 | (2006.01) |
| C07K 16/28 | (2006.01) |

(52) U.S. Cl.
CPC ............ *C07K 16/00* (2013.01); *C07K 14/315* (2013.01); *C07K 16/2896* (2013.01); *C07K 2317/35* (2013.01); *C07K 2317/55* (2013.01); *C07K 2317/624* (2013.01); *C07K 2319/00* (2013.01)

(58) Field of Classification Search
CPC ... G01N 33/537; C12P 21/02; B01D 15/3809; C07K 1/22; C07K 14/195; C07K 16/00; C07K 16/2896; C07K 14/315; C07K 14/31; C07K 2319/00; C07K 2317/55; C07K 2317/52; C07K 2317/51; C07K 2317/522; C07K 2317/54; C07K 2317/35; C07K 2319/55; C07K 2317/624
See application file for complete search history.

(56) References Cited

U.S. PATENT DOCUMENTS

| 6,492,498 B1 | 12/2002 | Vallera et al. | |
| 6,822,075 B2* | 11/2004 | Bjorck et al. | ................. 530/350 |
| 2003/0073149 A1* | 4/2003 | Archer | ..................... B82Y 5/00 |
| | | | 435/7.92 |
| 2005/0048512 A1 | 3/2005 | Kolkman et al. | |
| 2005/0100543 A1 | 5/2005 | Hansen et al. | |
| 2007/0009987 A1* | 1/2007 | Choe | ..................... C07K 14/21 |
| | | | 435/69.1 |
| 2007/0092933 A1 | 4/2007 | Garnier et al. | |
| 2007/0178541 A1* | 8/2007 | Pedersen et al. | ............. 435/7.32 |
| 2007/0269902 A1* | 11/2007 | Beechem et al. | ............. 436/501 |
| 2008/0292646 A1* | 11/2008 | Benhar | .................. C07K 14/21 |
| | | | 424/178.1 |
| 2012/0259099 A1 | 10/2012 | Choe et al. | |

FOREIGN PATENT DOCUMENTS

| EP | 1900754 | * | 3/2008 |
| EP | 1246925 | | 5/2008 |
| JP | 2008-542194 | | 11/2008 |
| JP | 2009-517337 | | 4/2009 |
| WO | WO 2005/000902 | | 1/2005 |
| WO | WO 2008/035217 | | 3/2008 |
| WO | WO 2008/052933 | | 5/2008 |
| WO | WO 2009/055653 | | 4/2009 |

OTHER PUBLICATIONS

Colman et al., Research in Immunology (145(1):33-35, 1994.*
Derrick et al., Nature 359: 752-754, Oct. 1992.*
Roque et al., J Chromatatogra A 1160: 44-55, 2007.*
Lee et al., J Biol Chem 285(8): 5127-5131, Feb. 19, 2010.*
Lee et al., J Biol Chem 285: 5127-5131 (Year: 2010).*
Willuda et al. "Tumor Targeting of Mono-, Di-, and Tetravalent Anti-p185HER-2 Miniantibodies Multimerized by Self-associating Peptides," The Journal of Biological Chemistry, Apr. 2001, vol. 276, No. 17, pp. 14385-14392.
Colman et al. "Effects of amino acid sequence changes on antibody-antigen interactions," Research in Immunology, 1994, vol. 145, No. 1, pp. 33-36.
Deyev et al. "Design of multivalent complexes using the barnase-barstar module," Nature Biotechnology, Dec. 2003, vol. 21, No. 12, pp. 1486-1492.
Park et al. "A Divalent Recombinant Immunotoxin Formed by a Disulfide Bond between the Extension Peptide Chains," Molecules and Cells, Dec. 2001, vol. 12, No. 3, pp. 398-402.
Won et al. "Disulfide Bond Bridged Divalent Antibody-Toxin, (Fab-PE38fl)2, with the Toxin PE38 Fused to the Light Chain" Journal of Microbiology and Biotechnology, Aug. 2008, vol. 18, No. 8, pp. 1475-1481.
Wu et al. "Humanization of a Murine Monoclonal Antibody by Simultaneous Optimization of Framework and CDR Residues," Journal of Molecular Biology, Nov. 1999, vol. 294, pp. 151-162.
International Search Report with English translation prepared by the Korean Intellectual Property Office dated Oct. 15, 2010 for International Application No. PCT/KR2009/007510.

(Continued)

*Primary Examiner* — Phuong Huynh
(74) *Attorney, Agent, or Firm* — Sheridan Ross P.C.

(57) ABSTRACT

The invention provides a method for preparing a super-complex which comprises repeat-chains containing single or multiple kinds of monomer-specific protein binding domains having at least two binding sites for a monomer repeated therein; preparing single complexes of the repeat-chains and a protein monomer having at least two binding sites for the monomer-specific binding domain of the repeat-chains, by mixing the repeat-chains and the protein monomer, and then generating the super-complex by forming cross-binding between the single complexes of repeat-chains and the protein monomers.

6 Claims, 32 Drawing Sheets

Specification includes a Sequence Listing.

(56) References Cited

OTHER PUBLICATIONS

Guss et al. "Structure of the IgG-binding regions of streptococcal protein G," The Embo Journal, 1986, vol. 5, No. 7, pp. 1567-1575.
Chen et al. "Fusion Protein Linkers: Property, Design and Functionality," Advanced Drug Delivery Reviews, Oct. 2013, vol. 65, No. 10, pp. 1357-1369.
Crasto et al. "LINKER: a program to generate linker sequences for fusion proteins," Protein Engineering, 2000, vol. 13, No. 5, pp. 309-312.

* cited by examiner

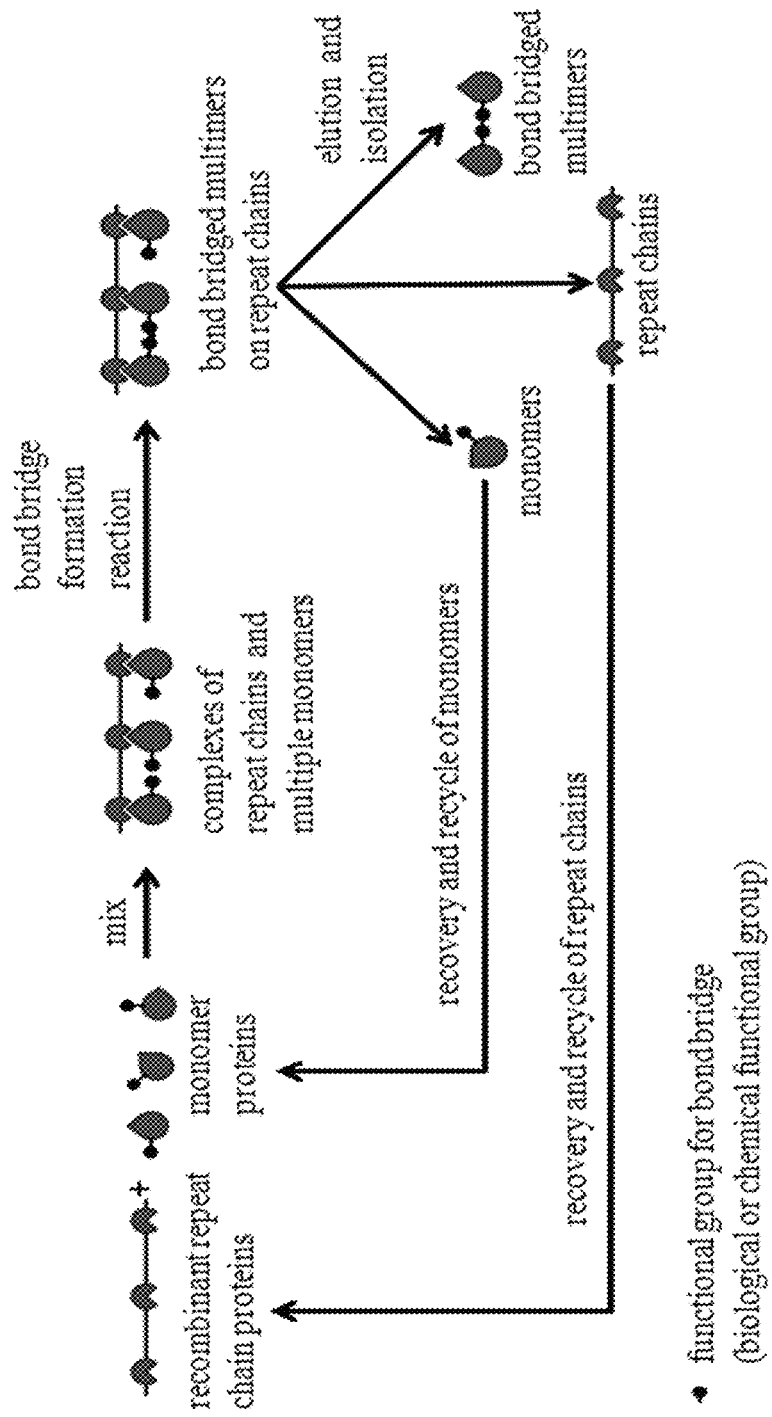
[Fig. 1]

[Fig. 2]
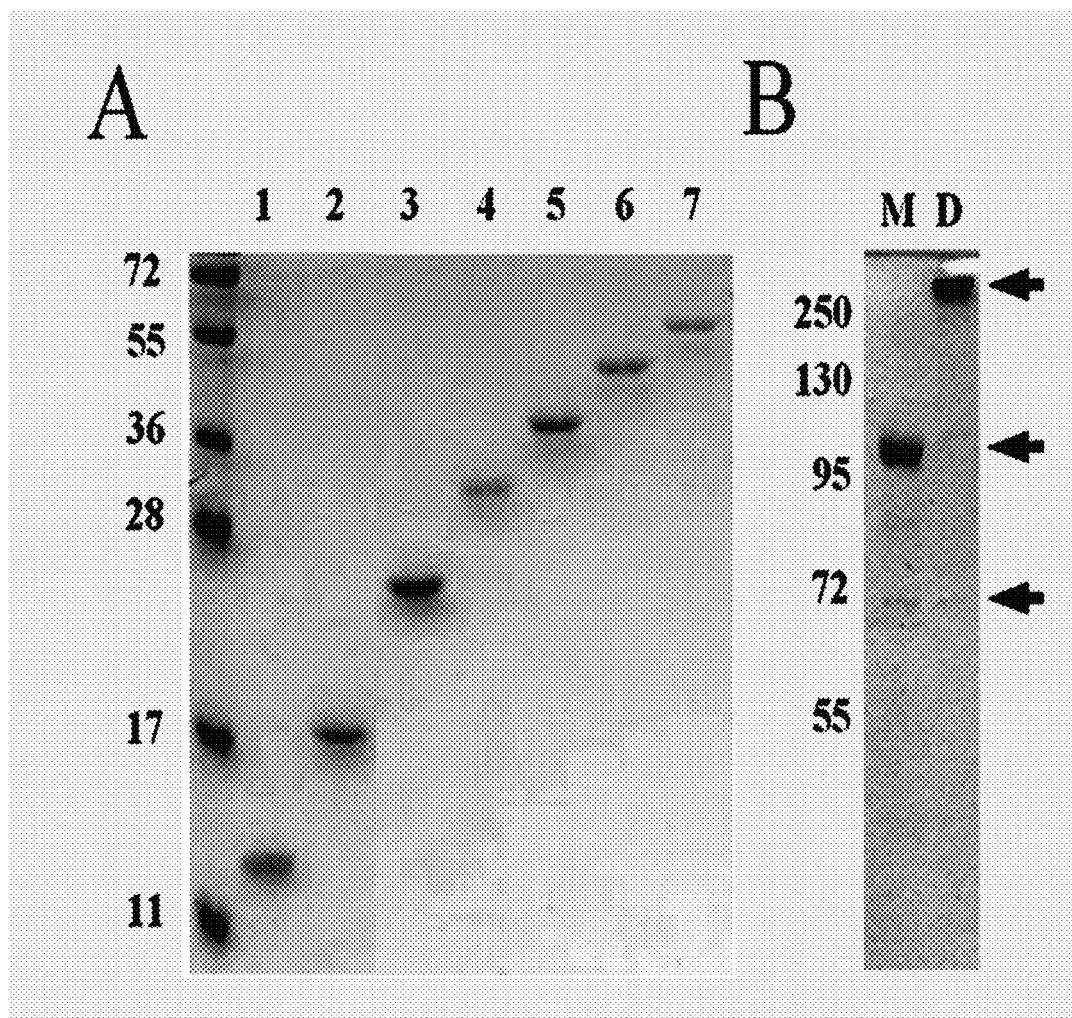

[Fig. 3]
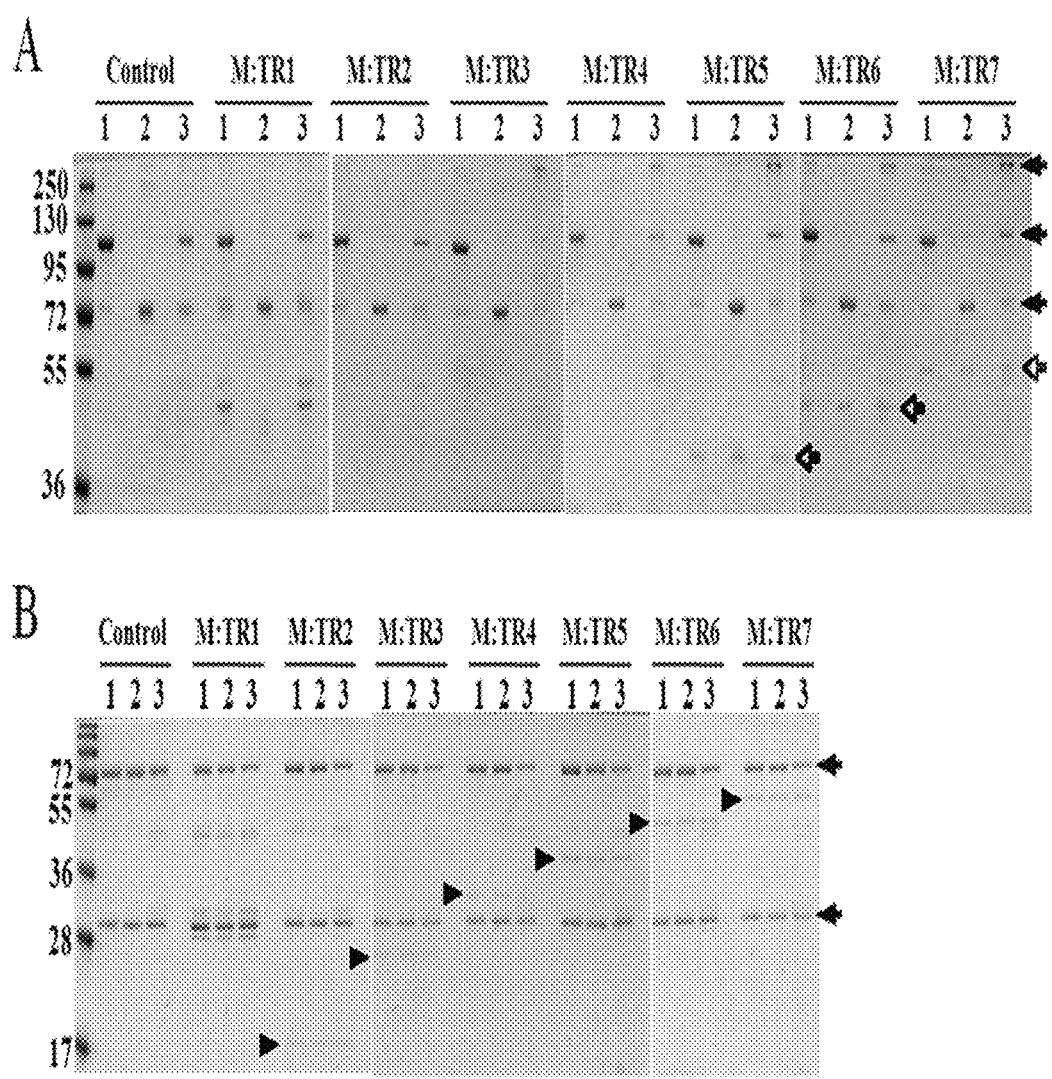

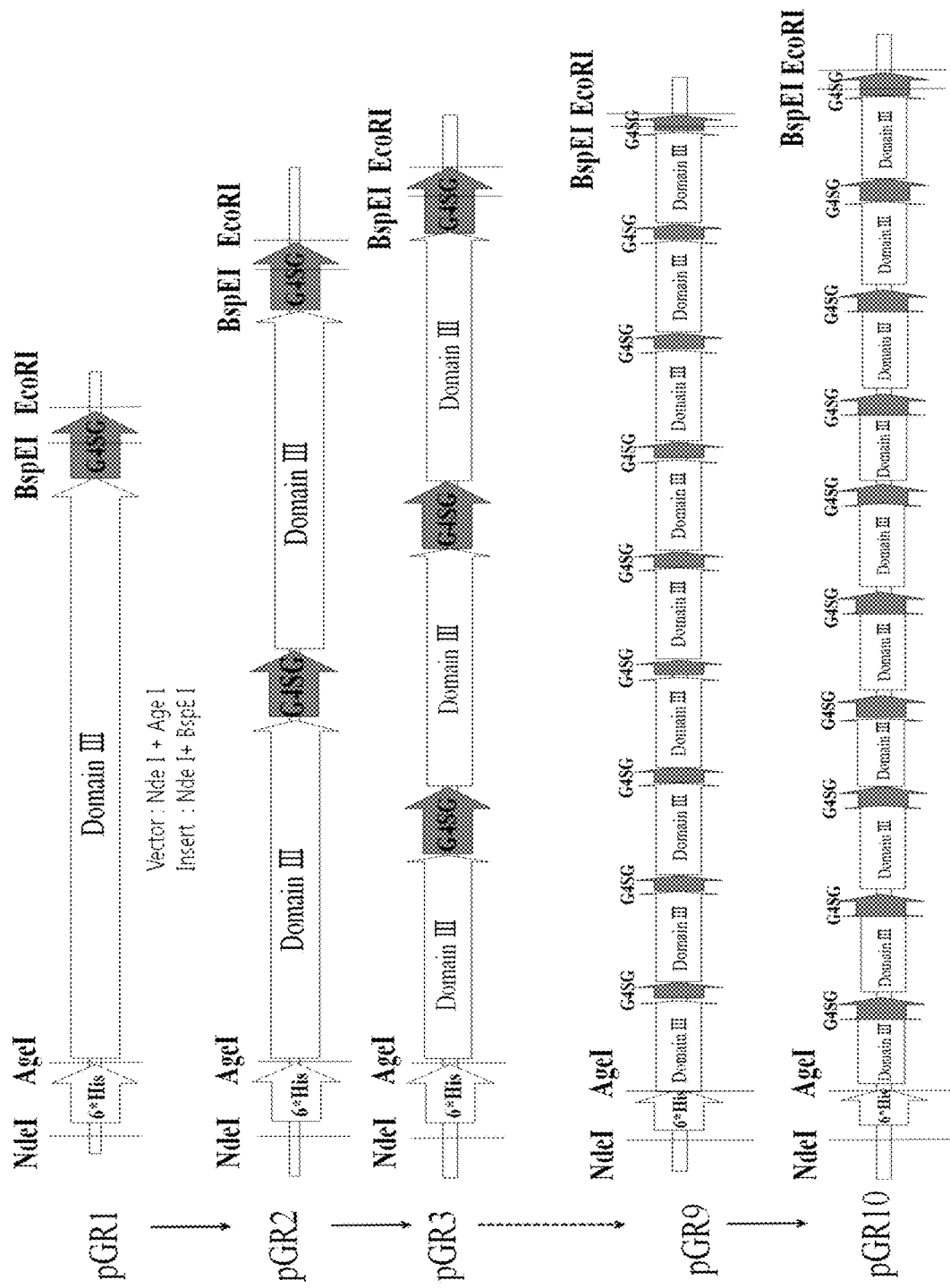

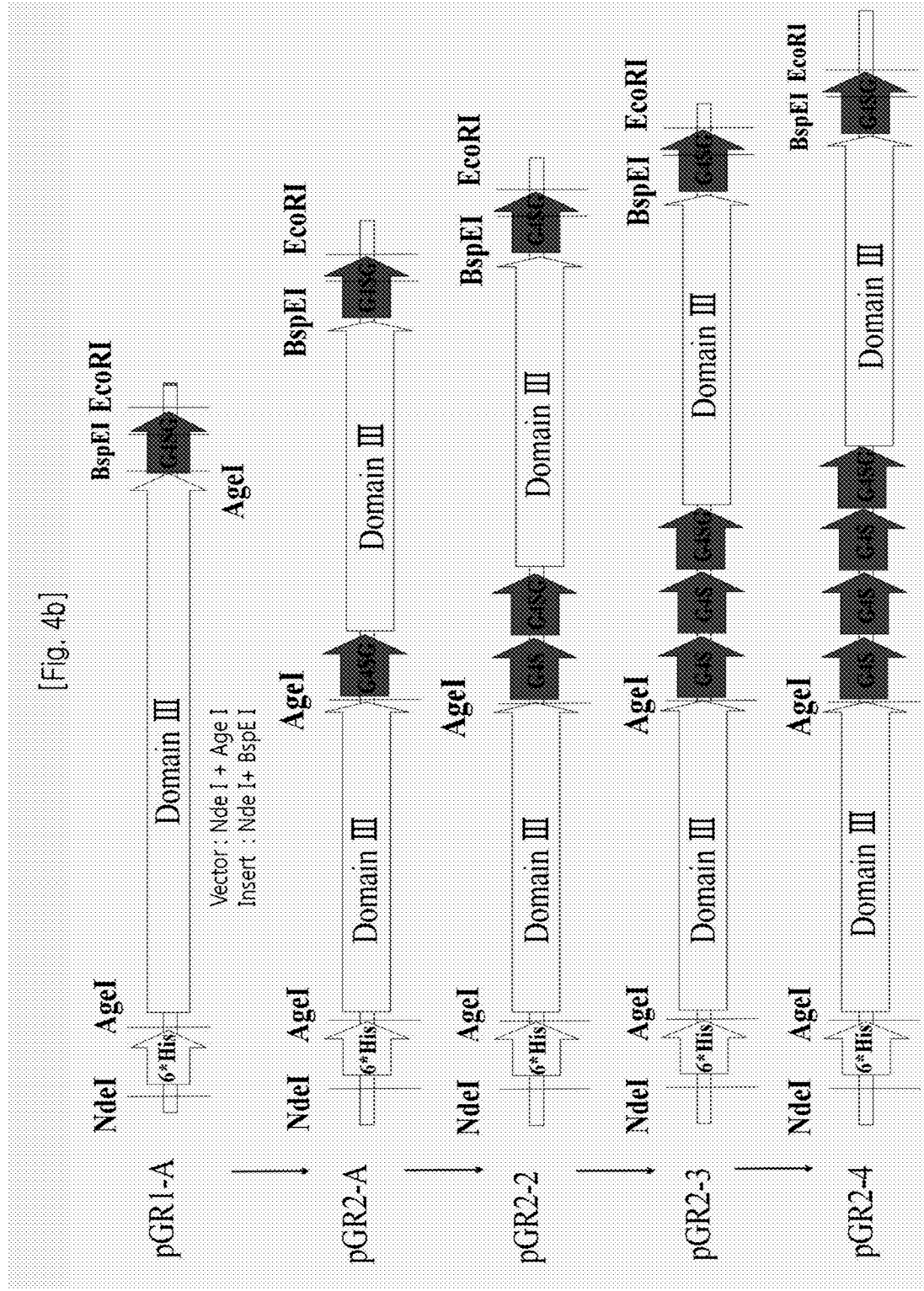

[Fig. 5]
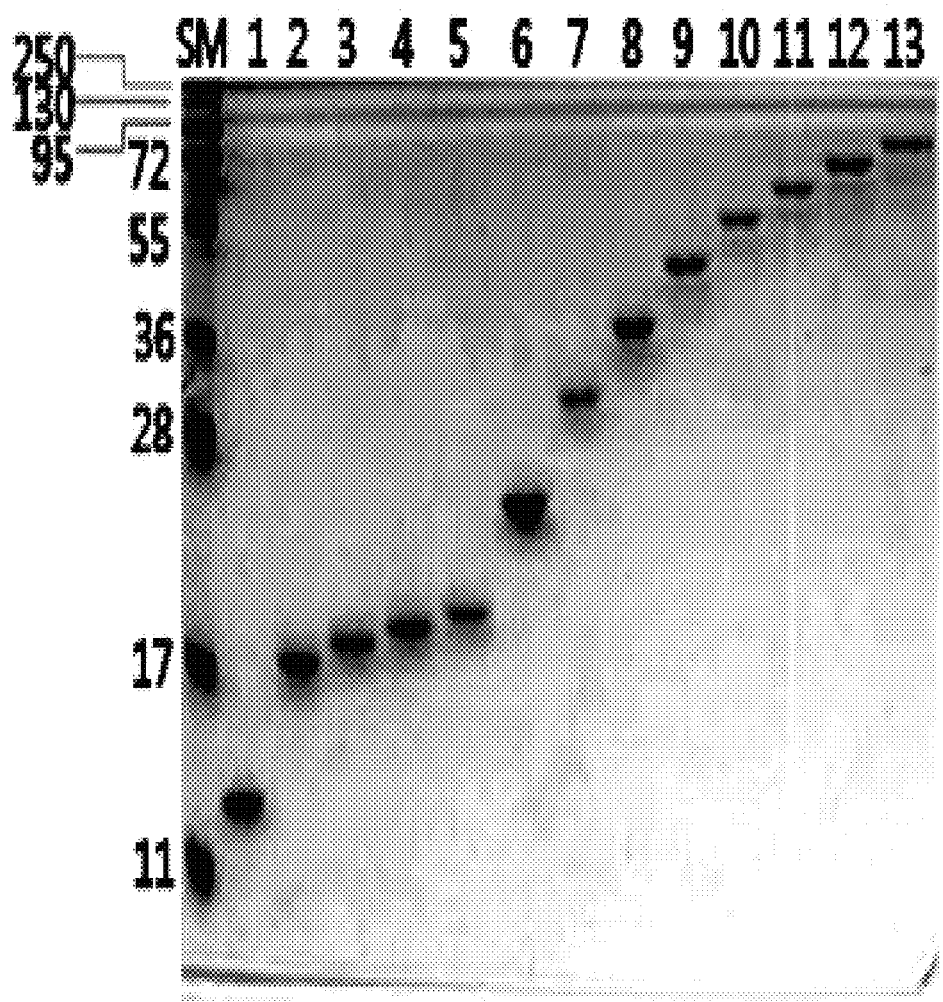

[Fig. 6]
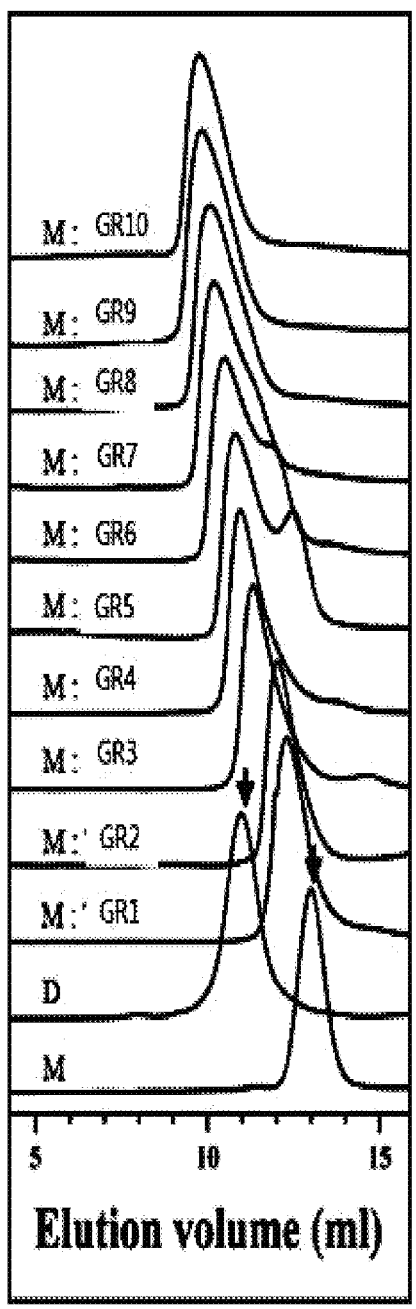
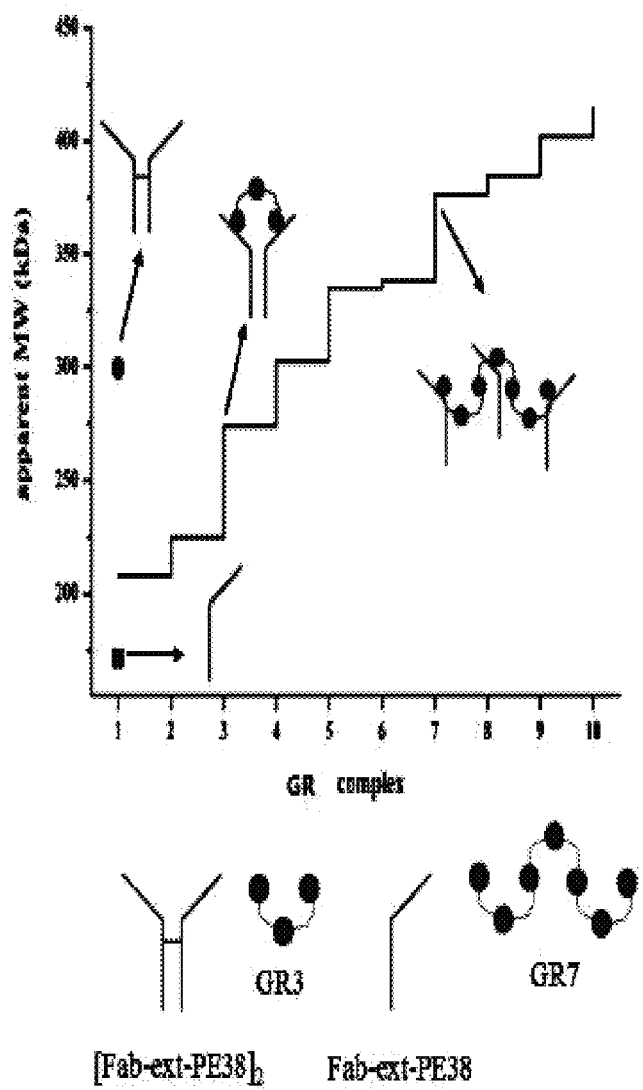

[Fig. 7]
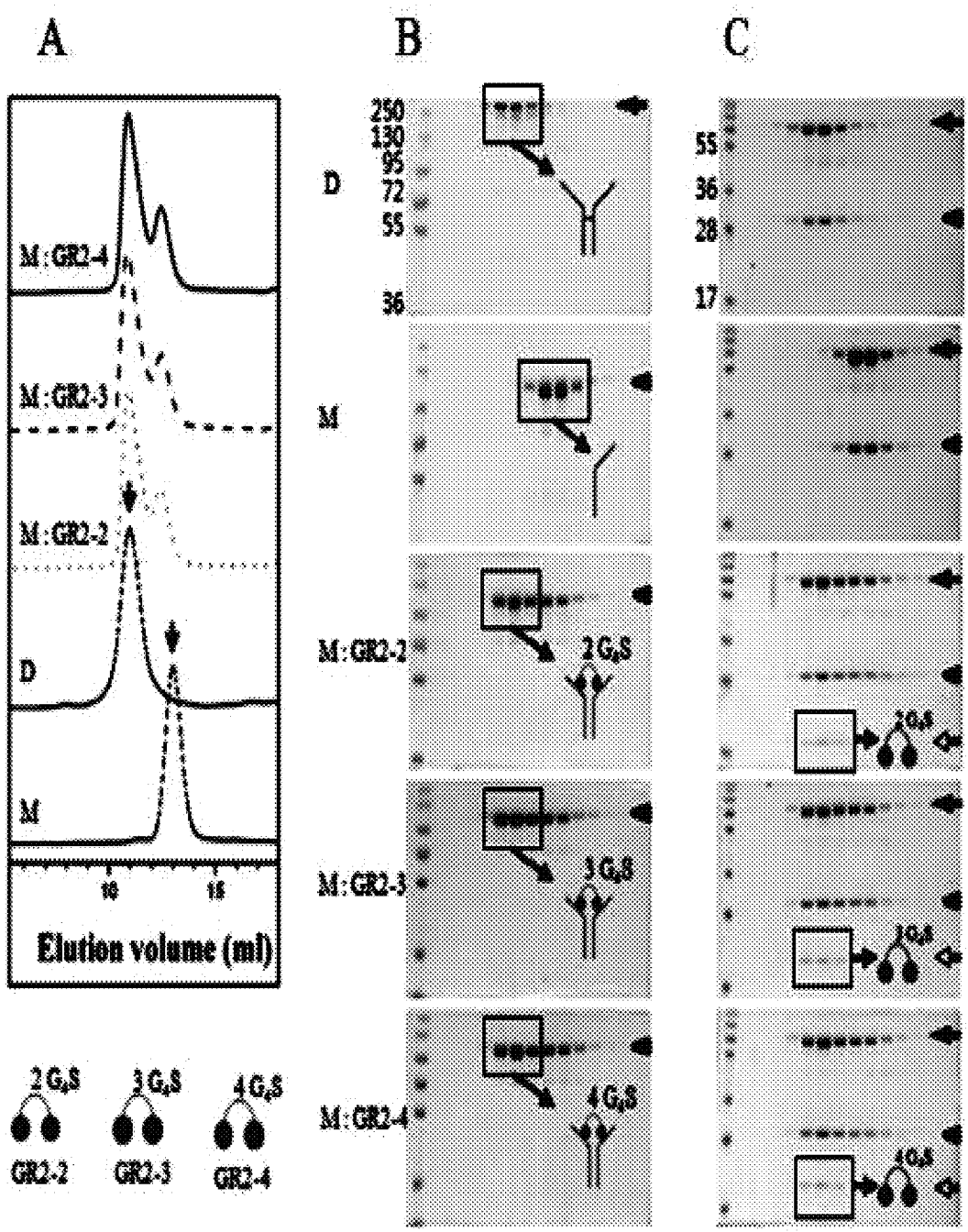

[Fig. 8]
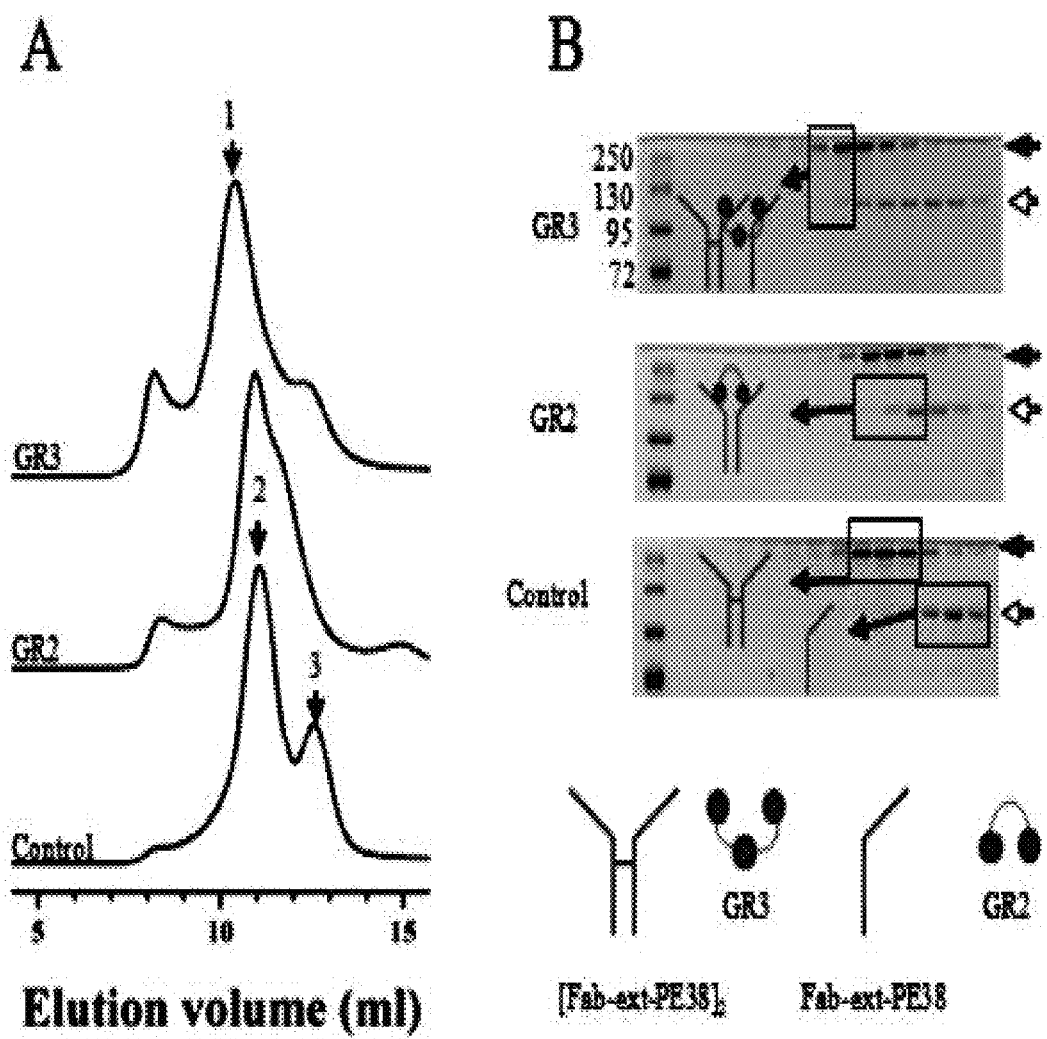

[Fig. 9]
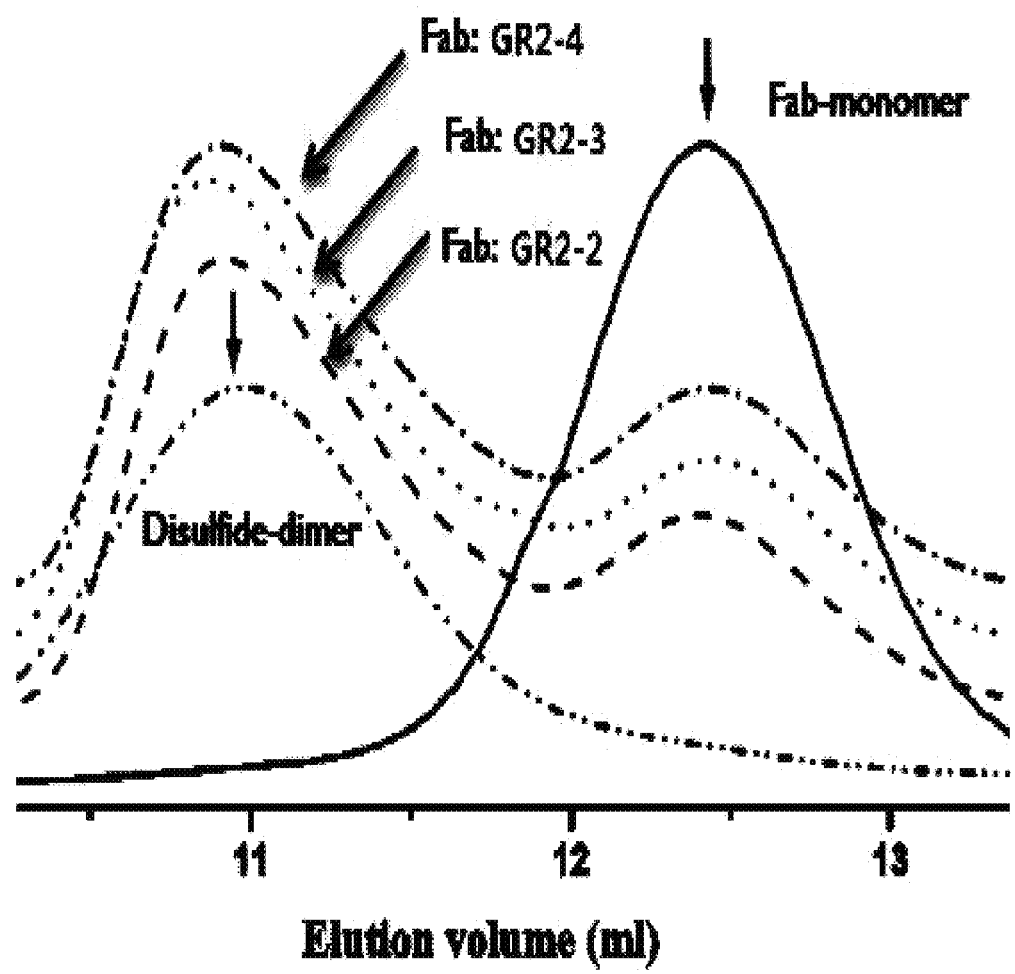

[Fig. 11]
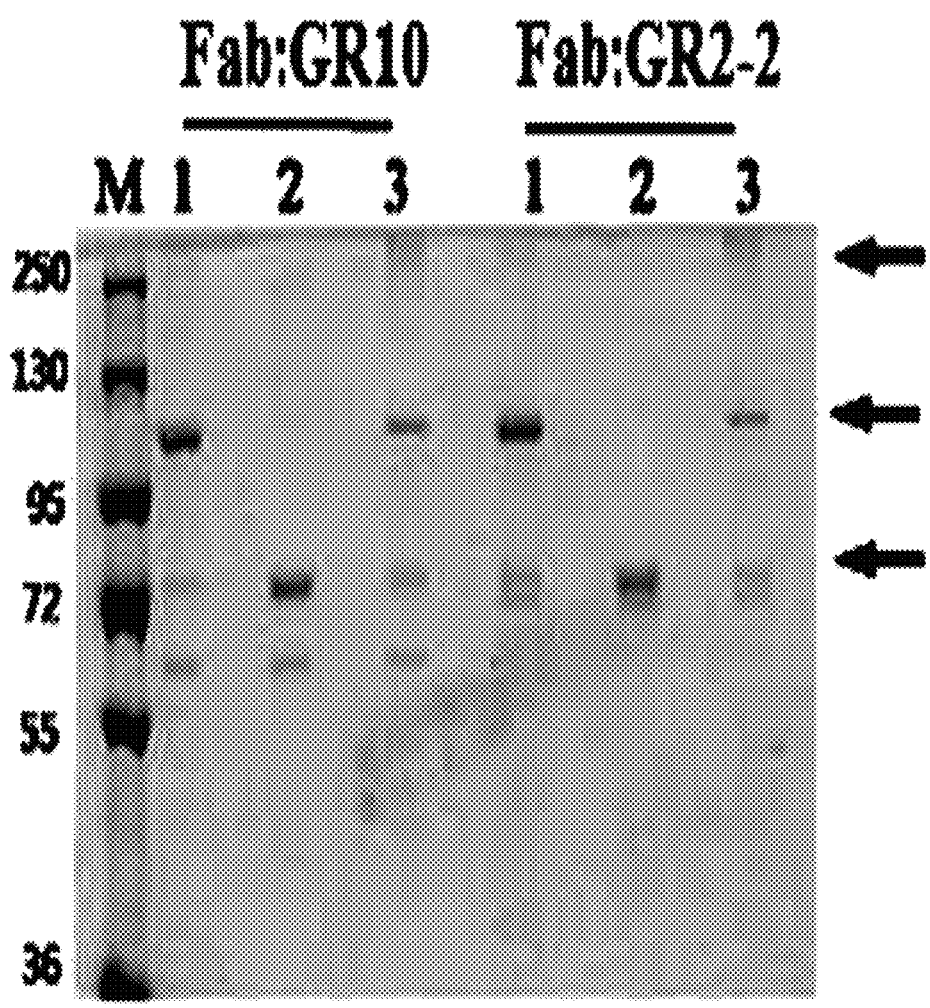

[Fig. 12]
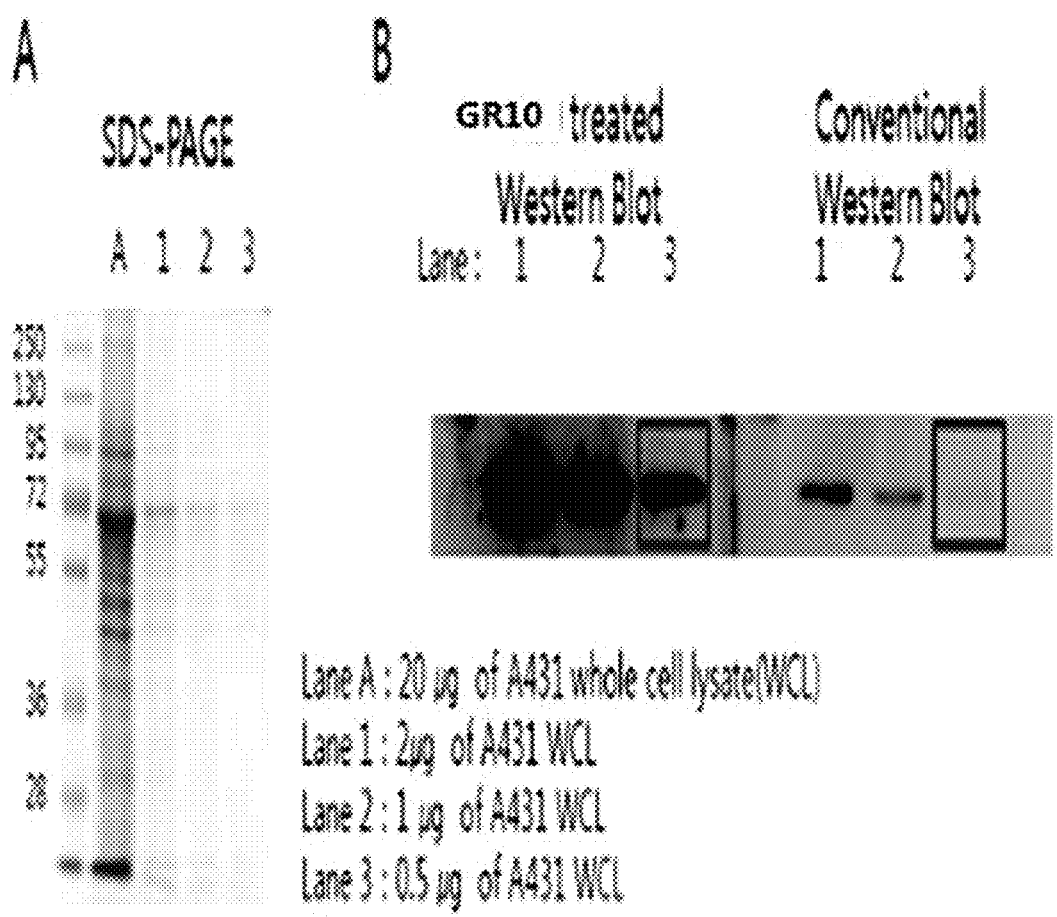

[Fig. 13]
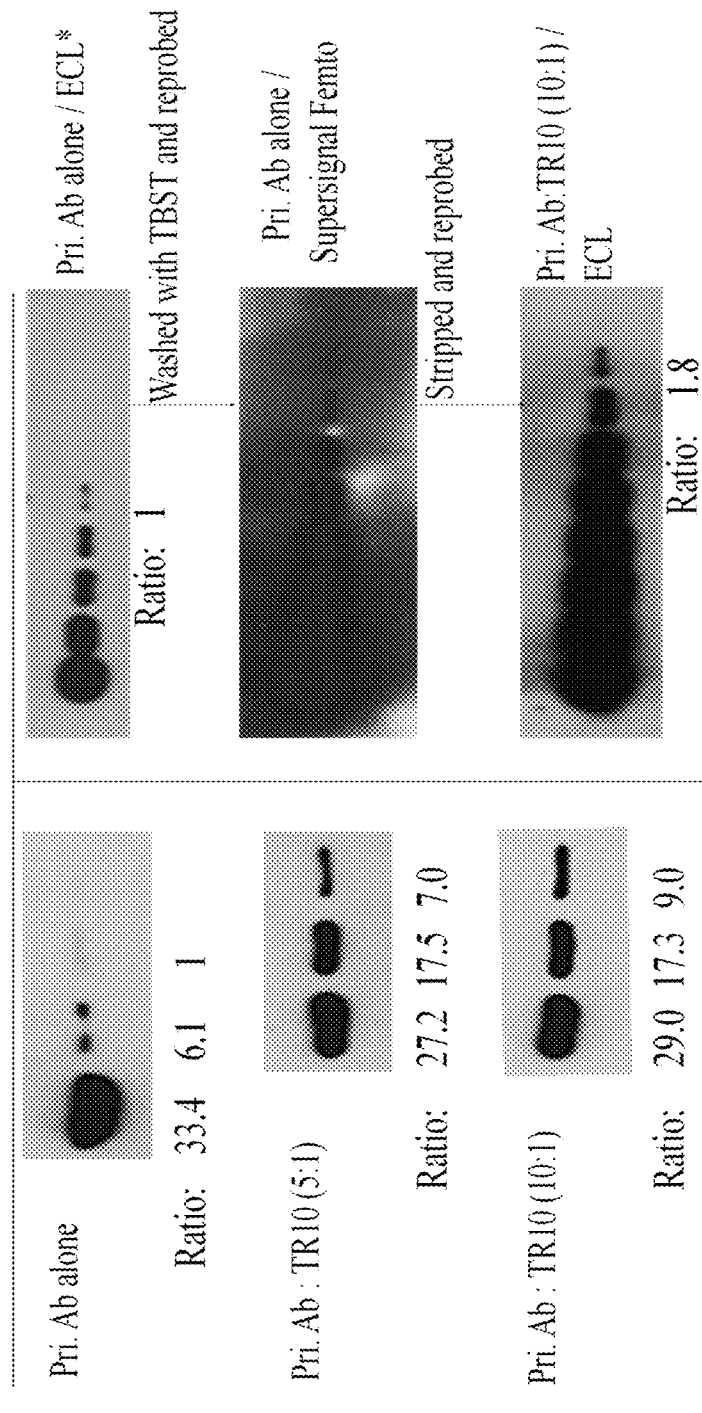

[Fig. 14]
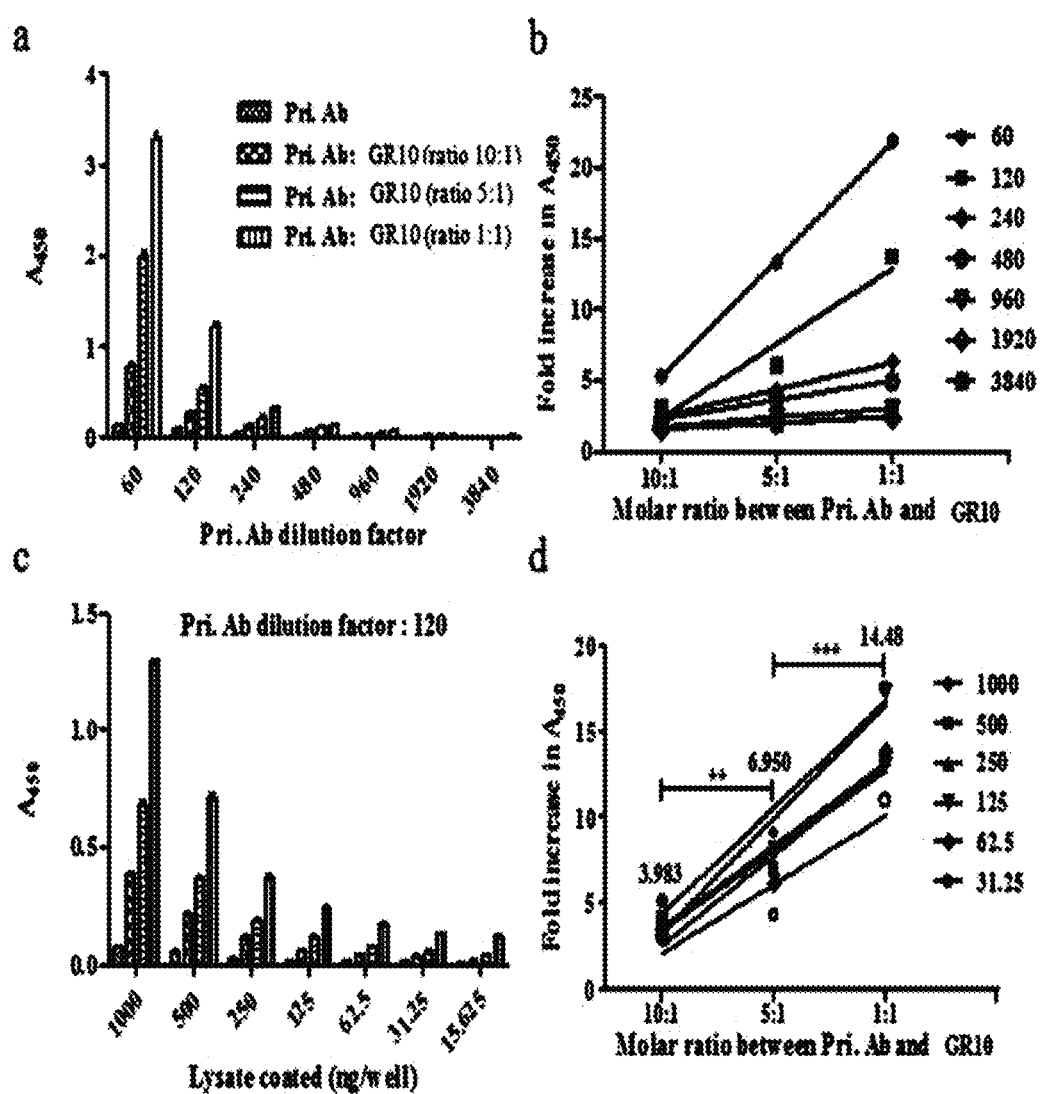

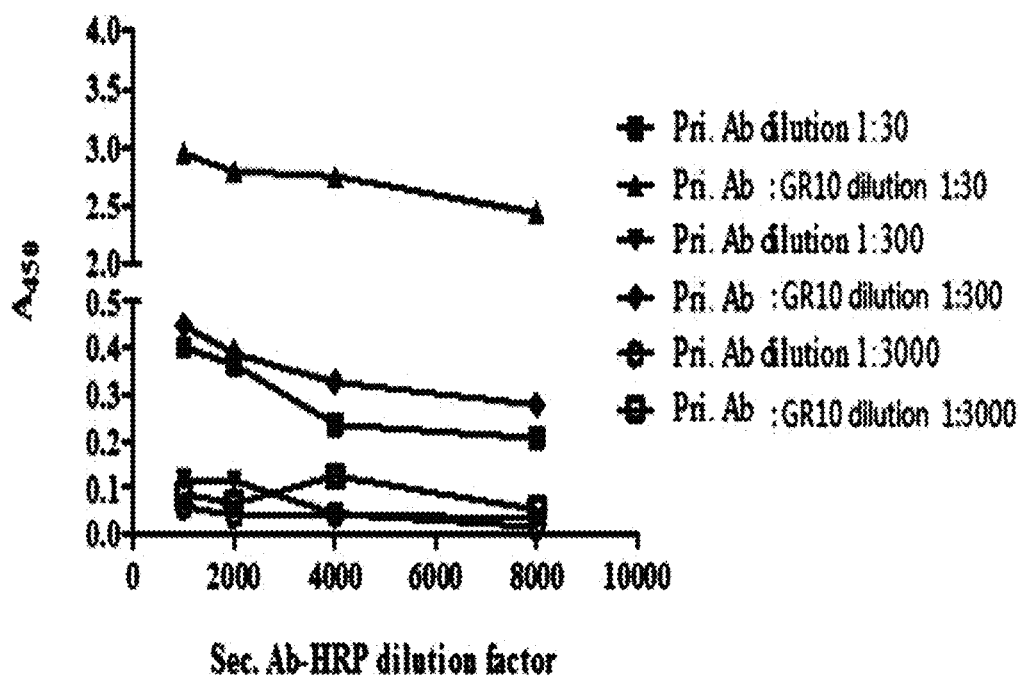
[Fig. 15]

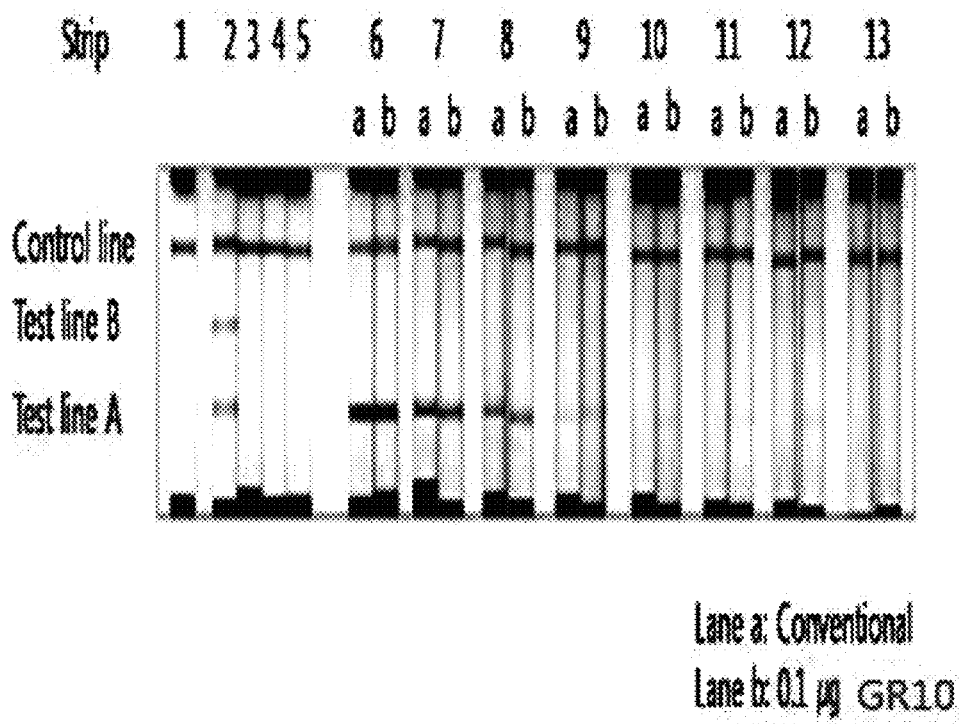
[Fig. 16]

[Fig. 17]
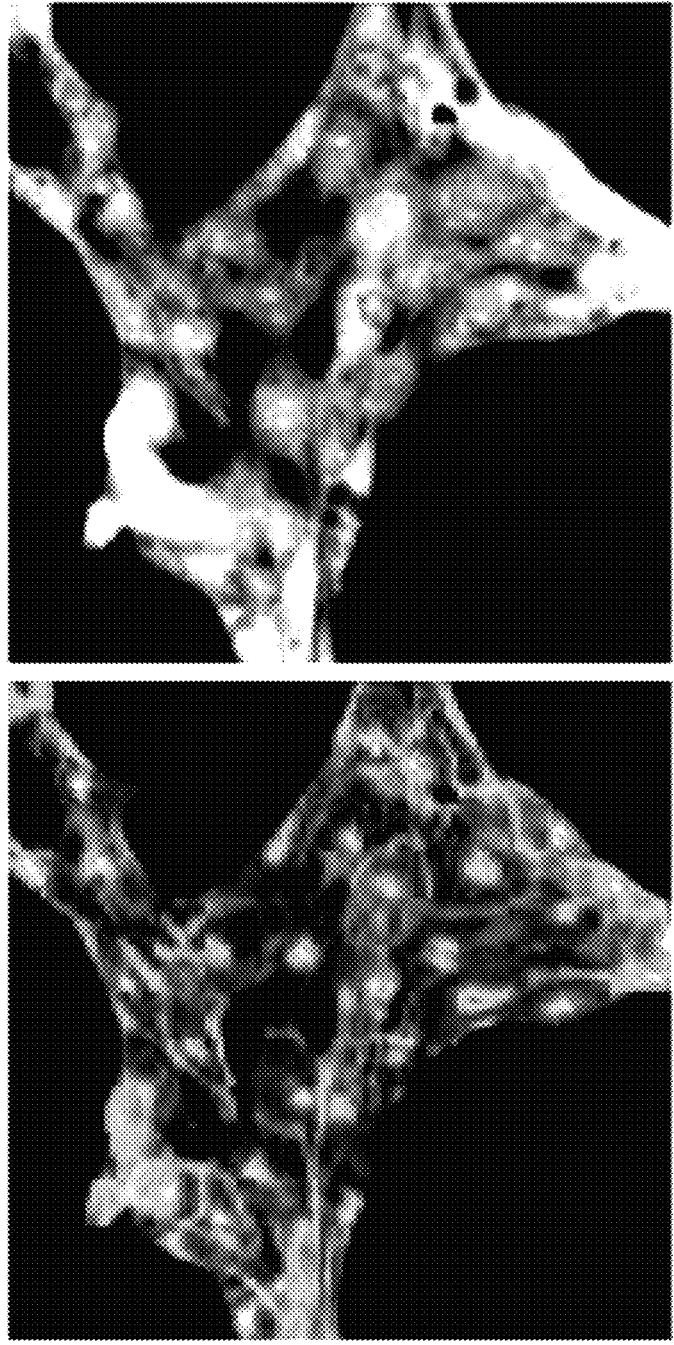

[Fig. 18]
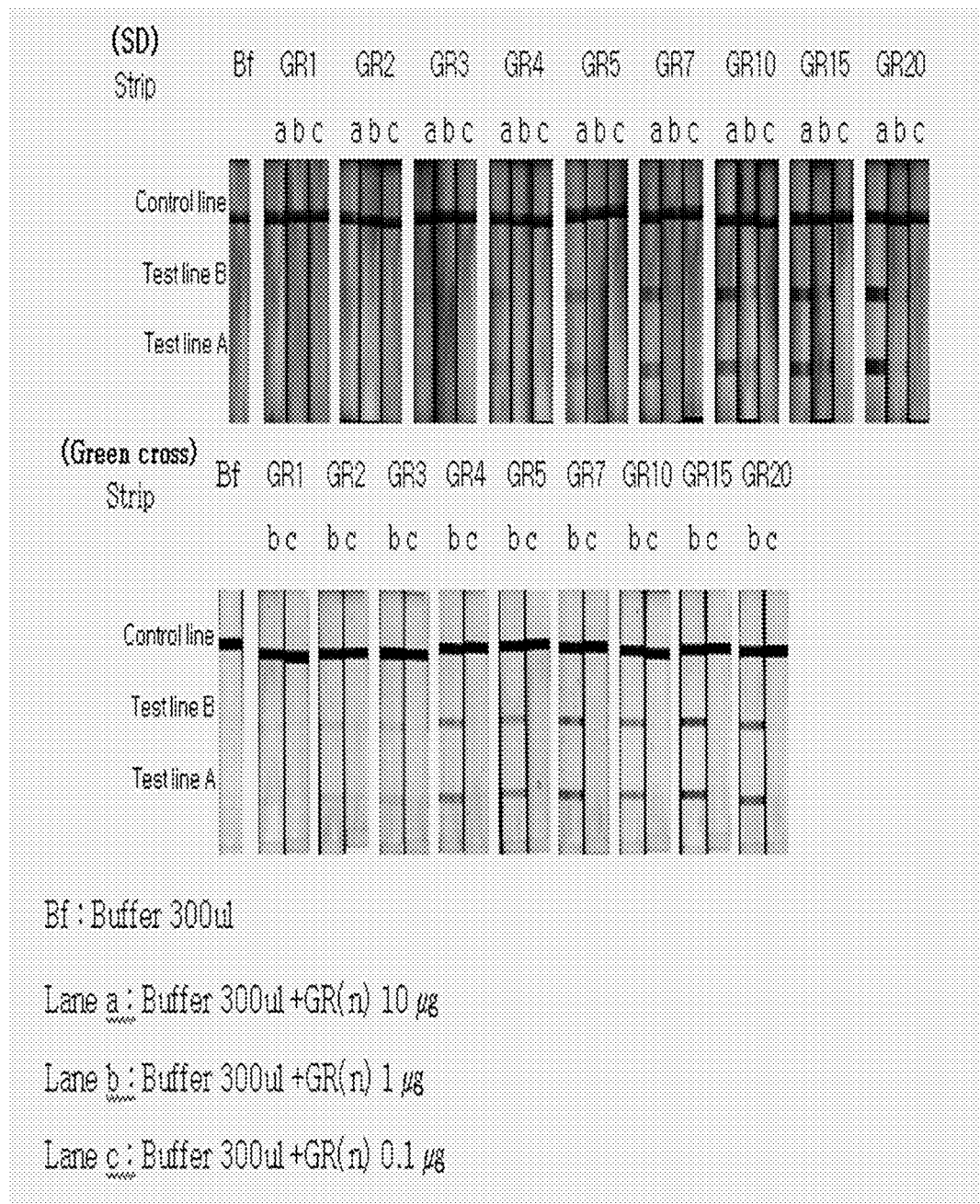

[Fig. 19]
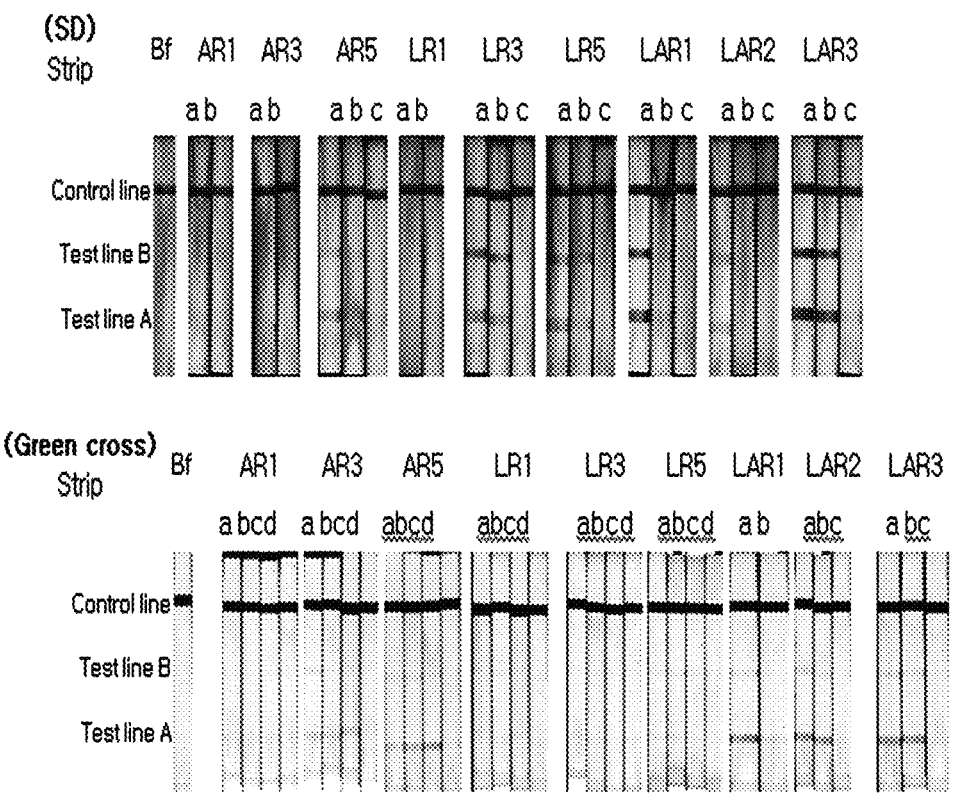
Bf : Buffer 300ul
Lane a : Buffer 300ul +Repeat chain 10 μg
Lane b : Buffer 300ul +Repeat chain 1 μg
Lane c : Buffer 300ul +Repeat chain 0.1 μg
Lane d : Buffer 300ul +Repeat chain 0.01 μg

[Fig. 20]
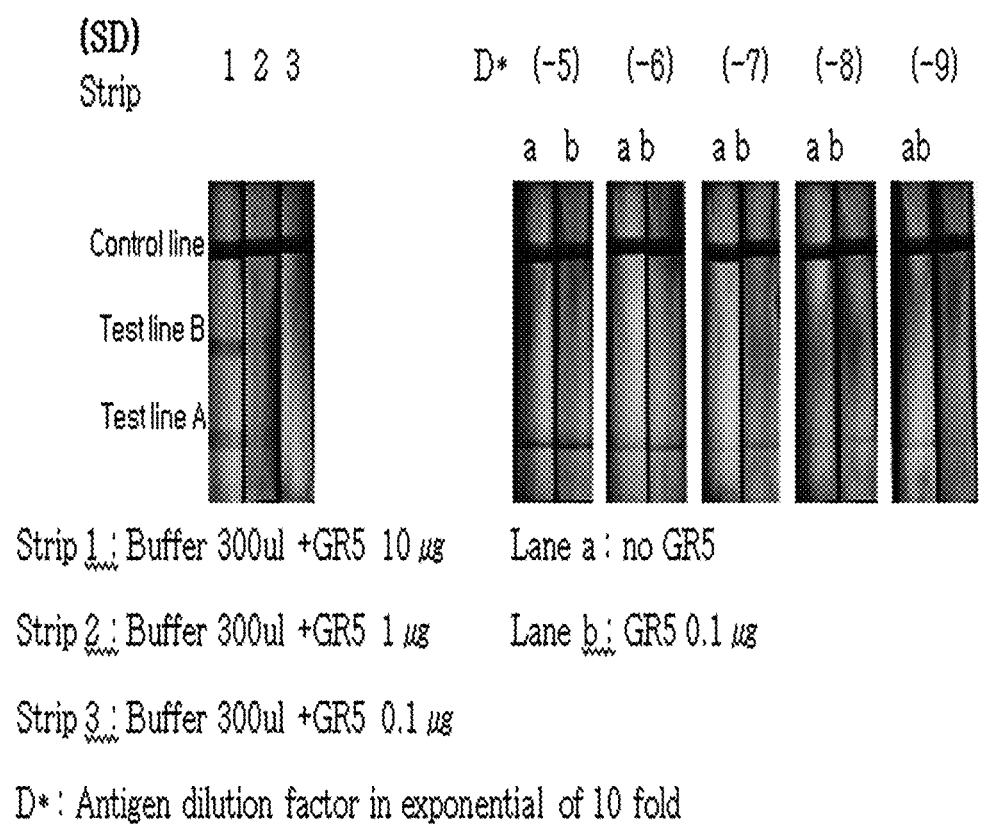

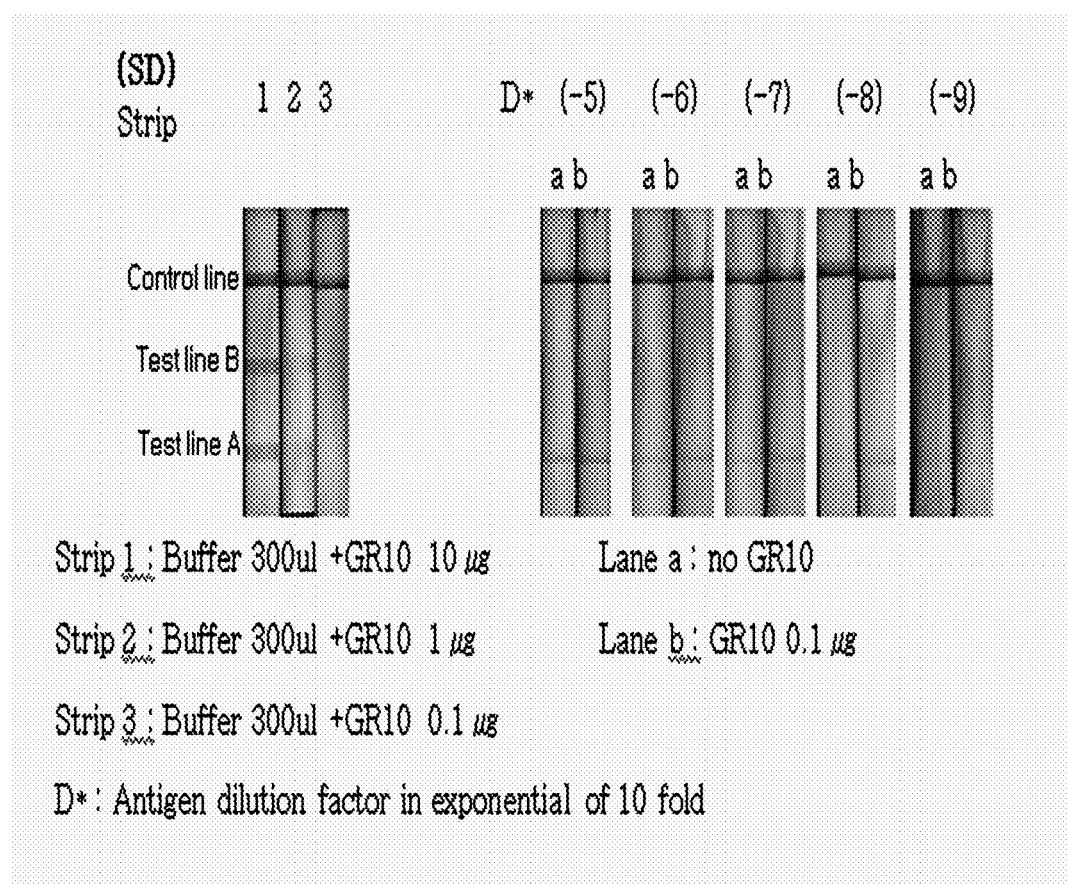
[Fig. 21]

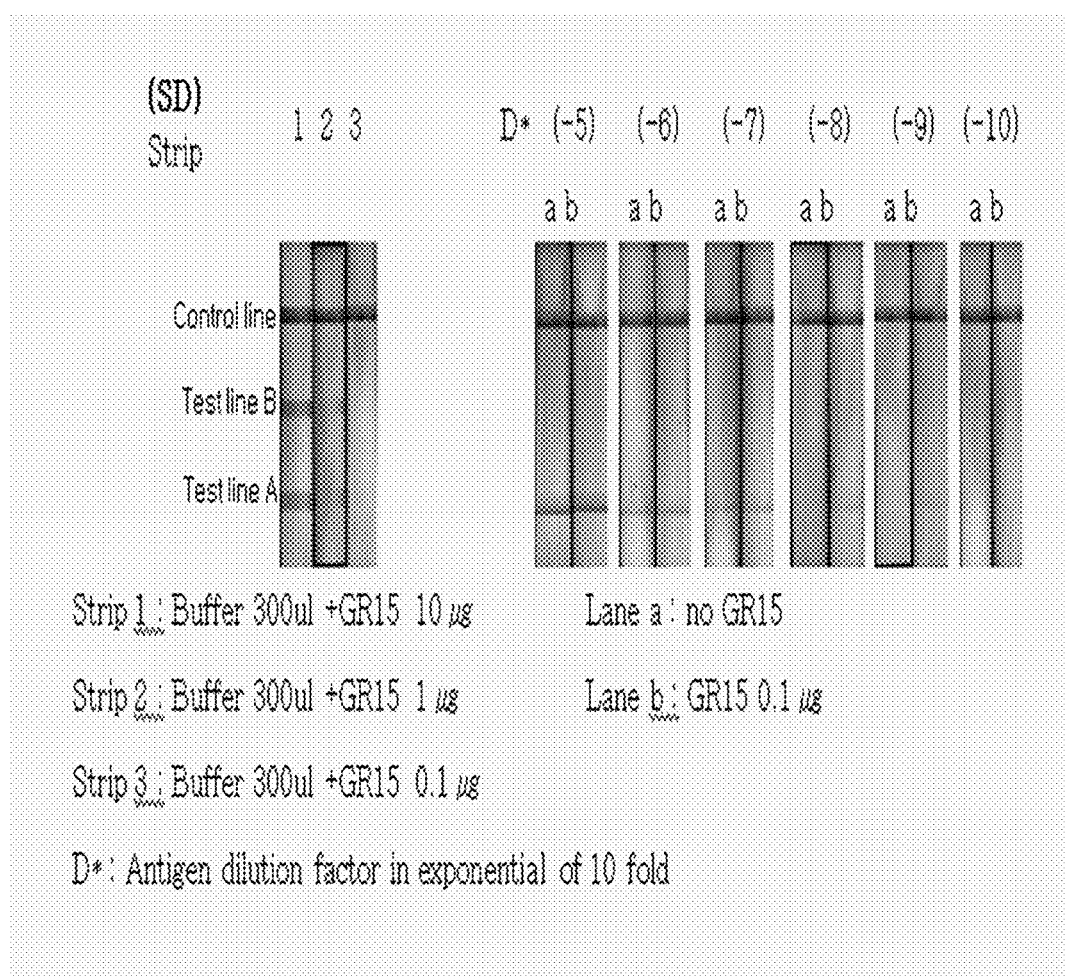
[Fig. 22]

[Fig. 23]
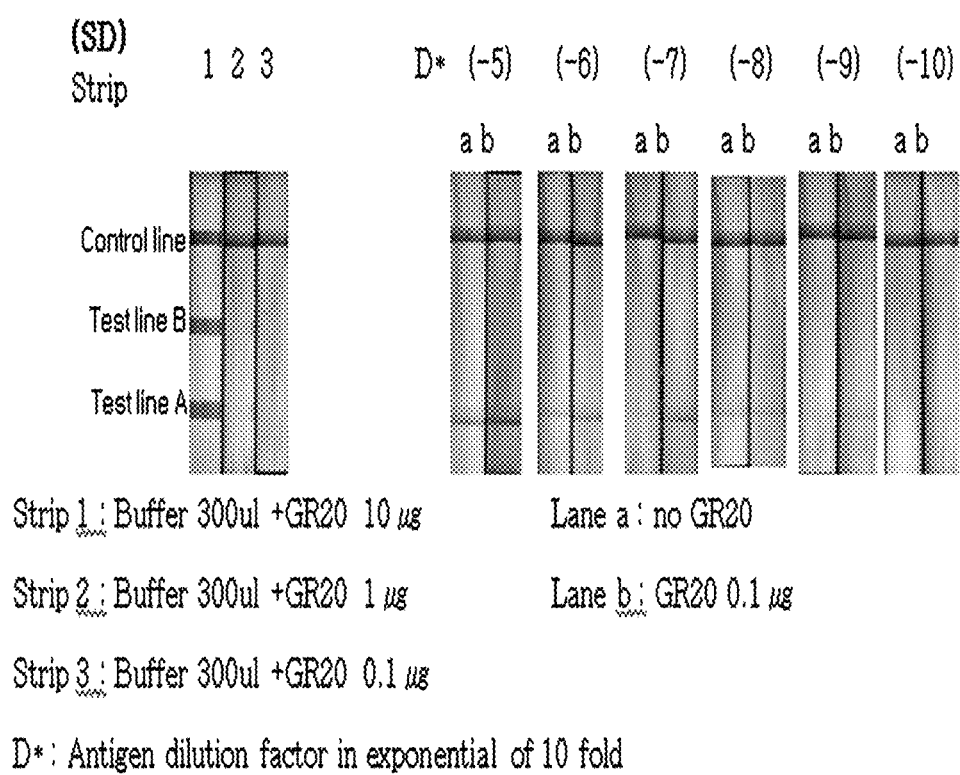

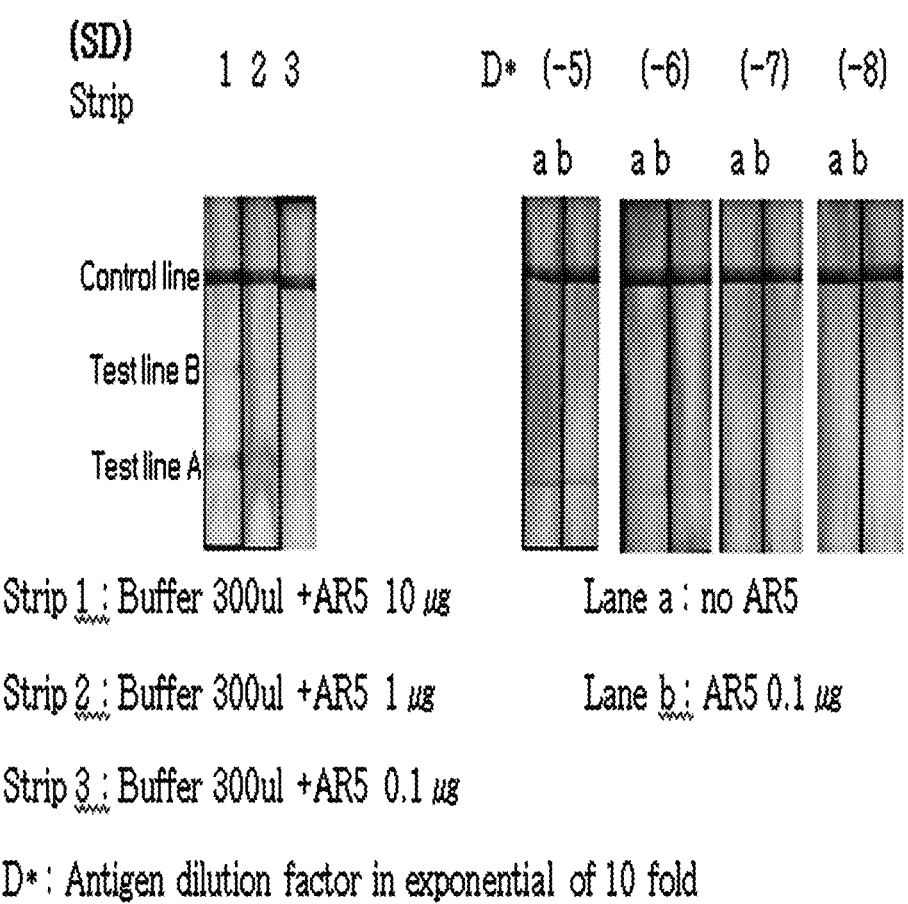
[Fig. 24]

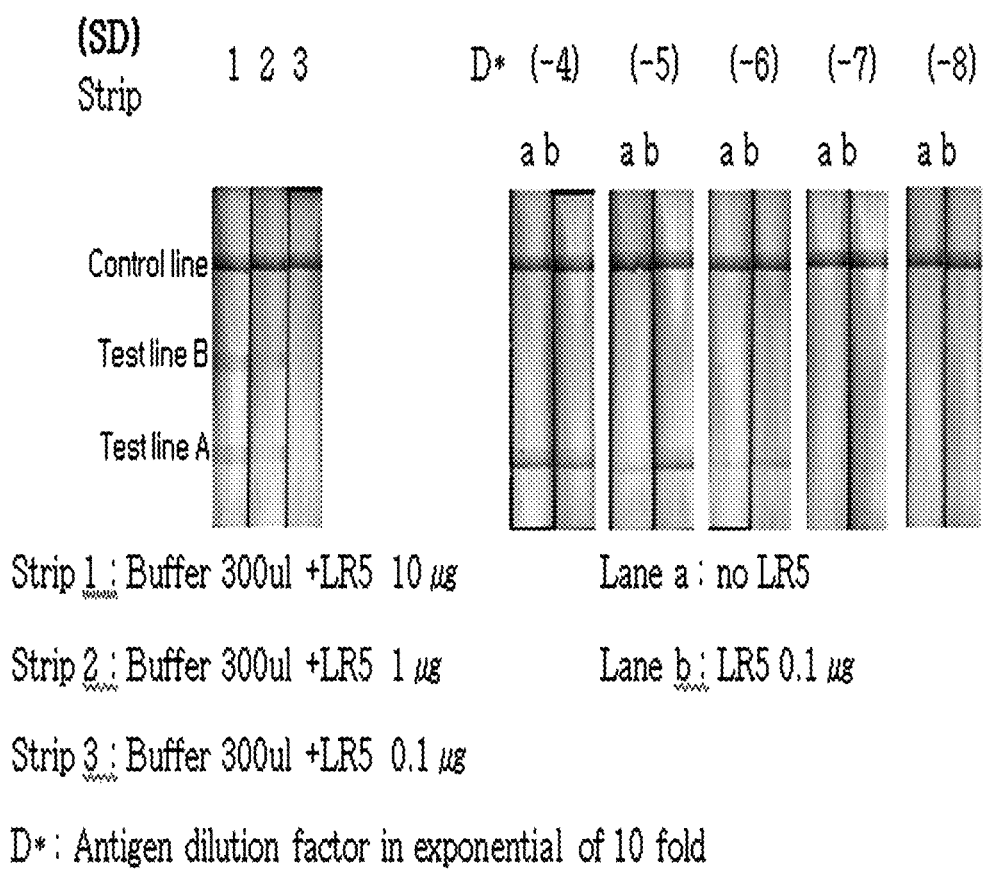
[Fig. 25]

[Fig. 26]
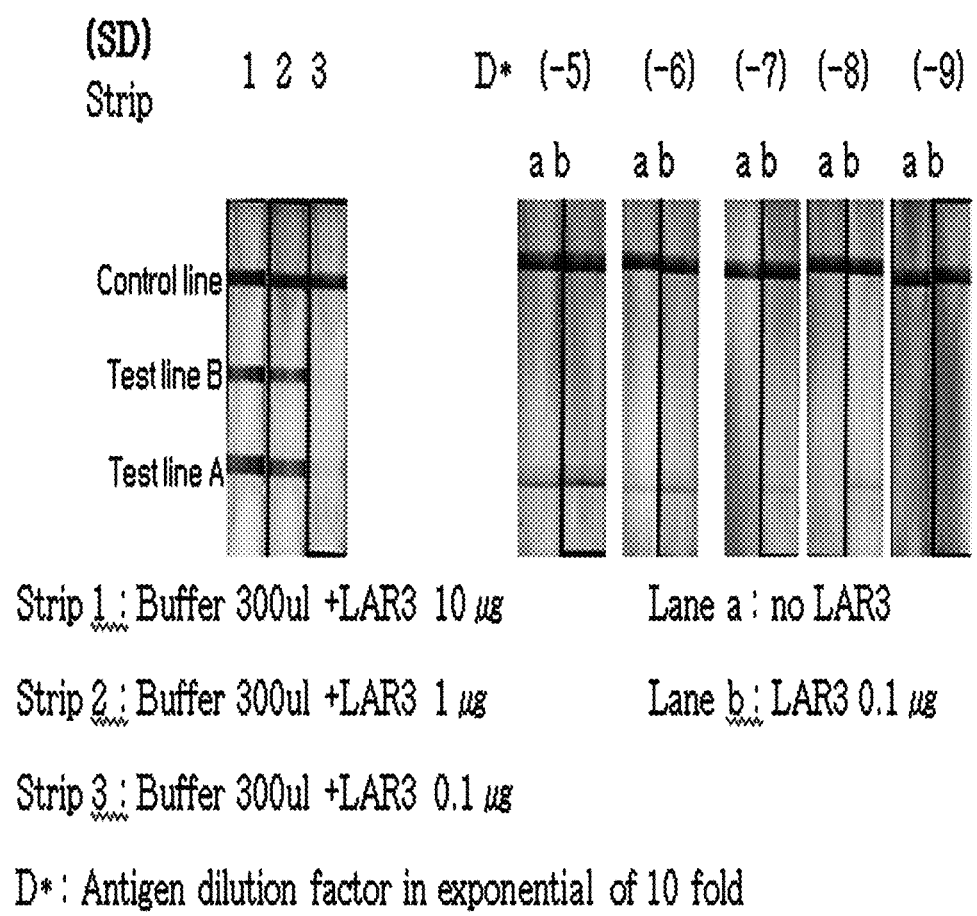

[Fig. 27]
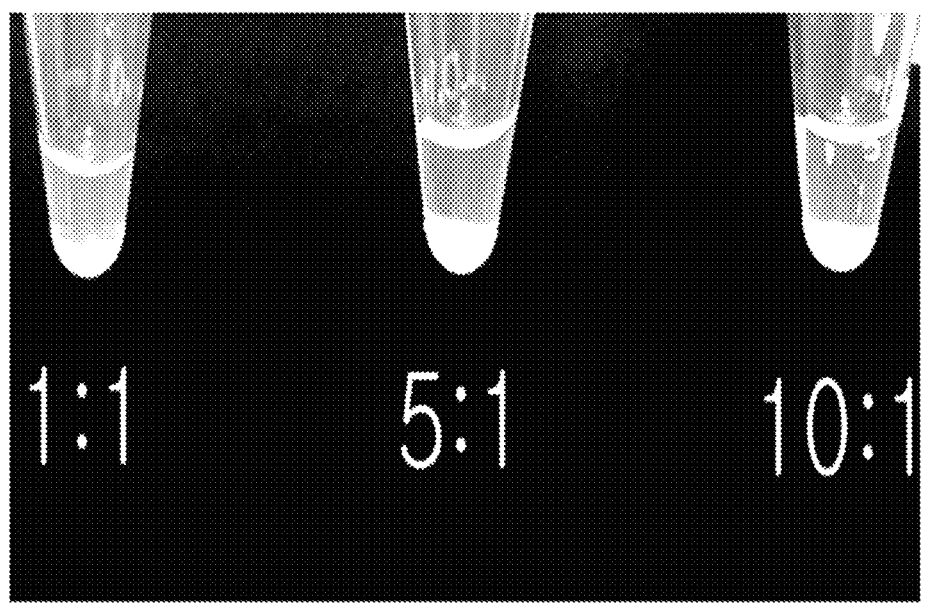

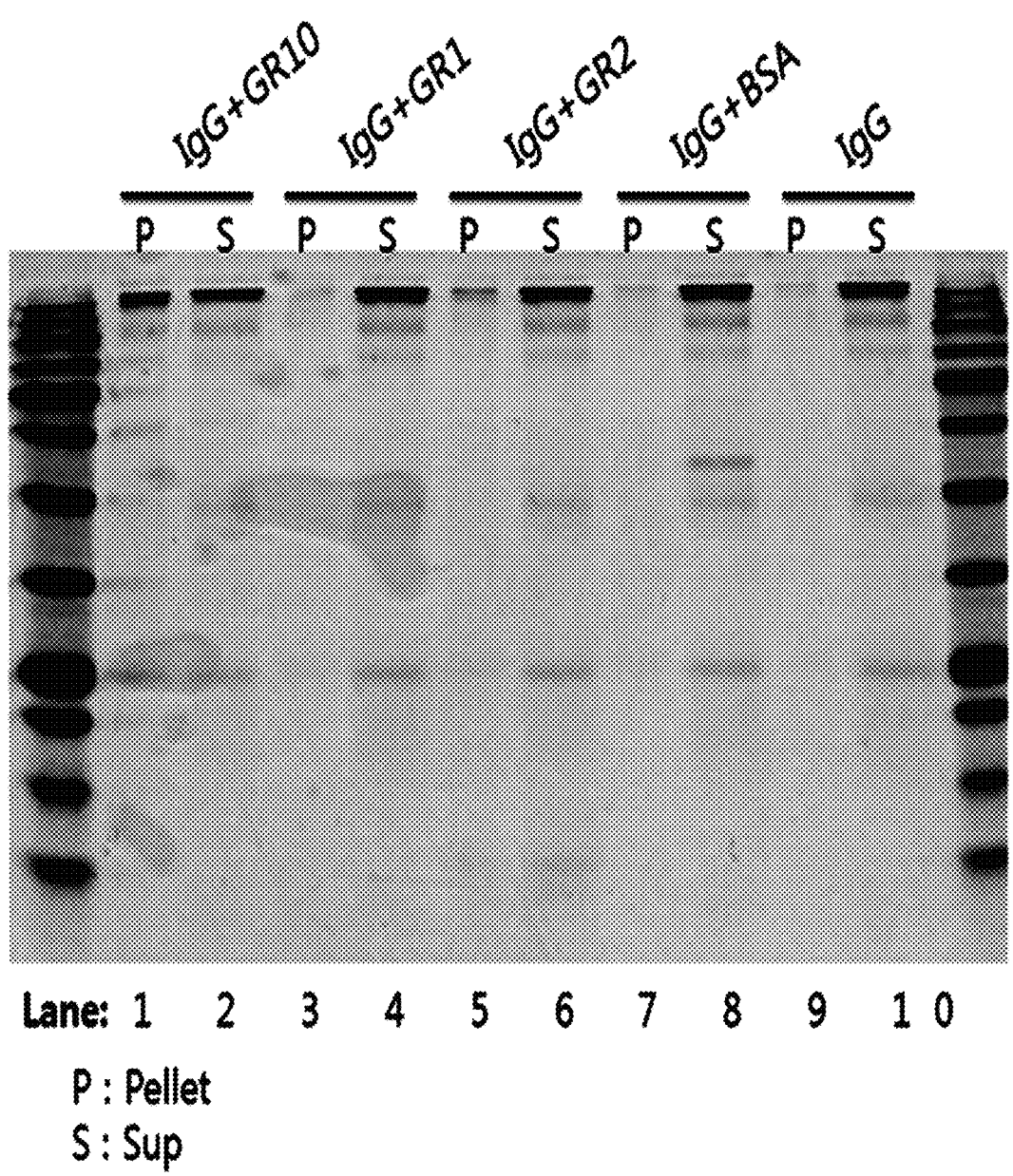
[Fig. 28]

[Fig. 29]
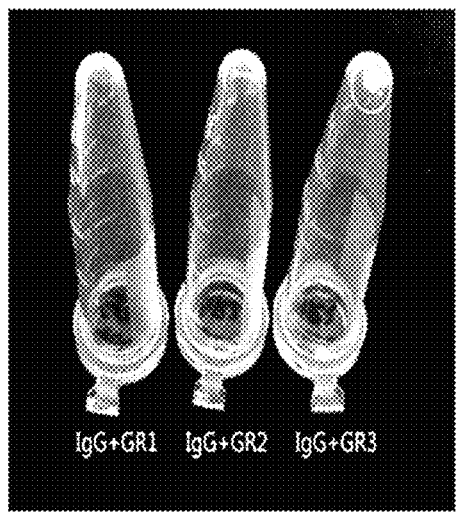
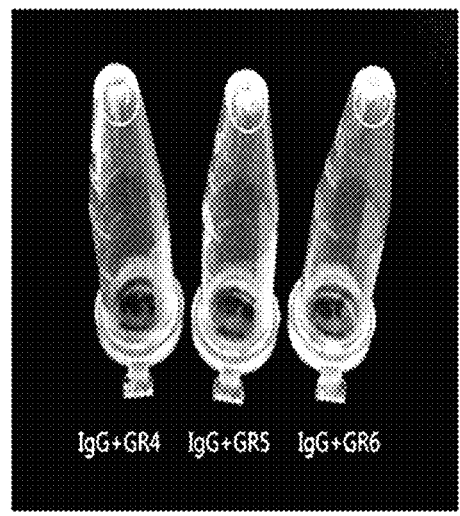
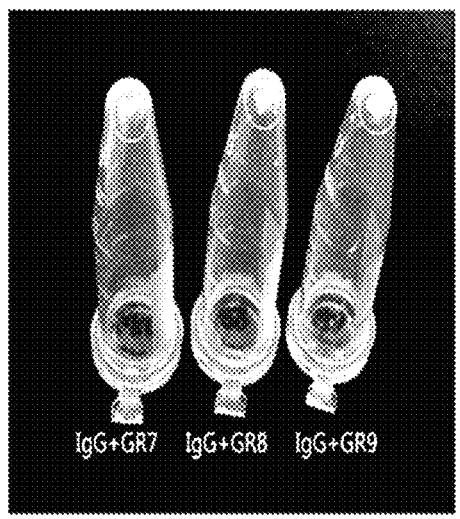
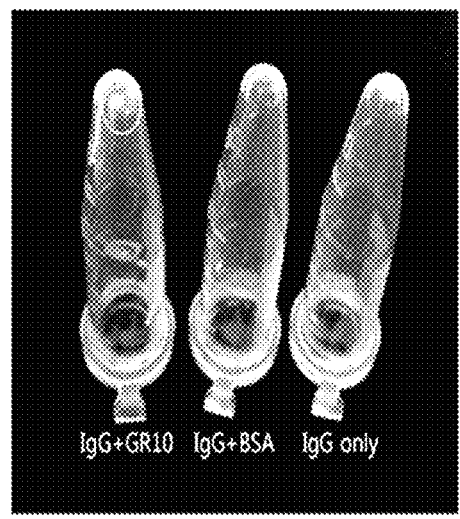

[Fig. 30]
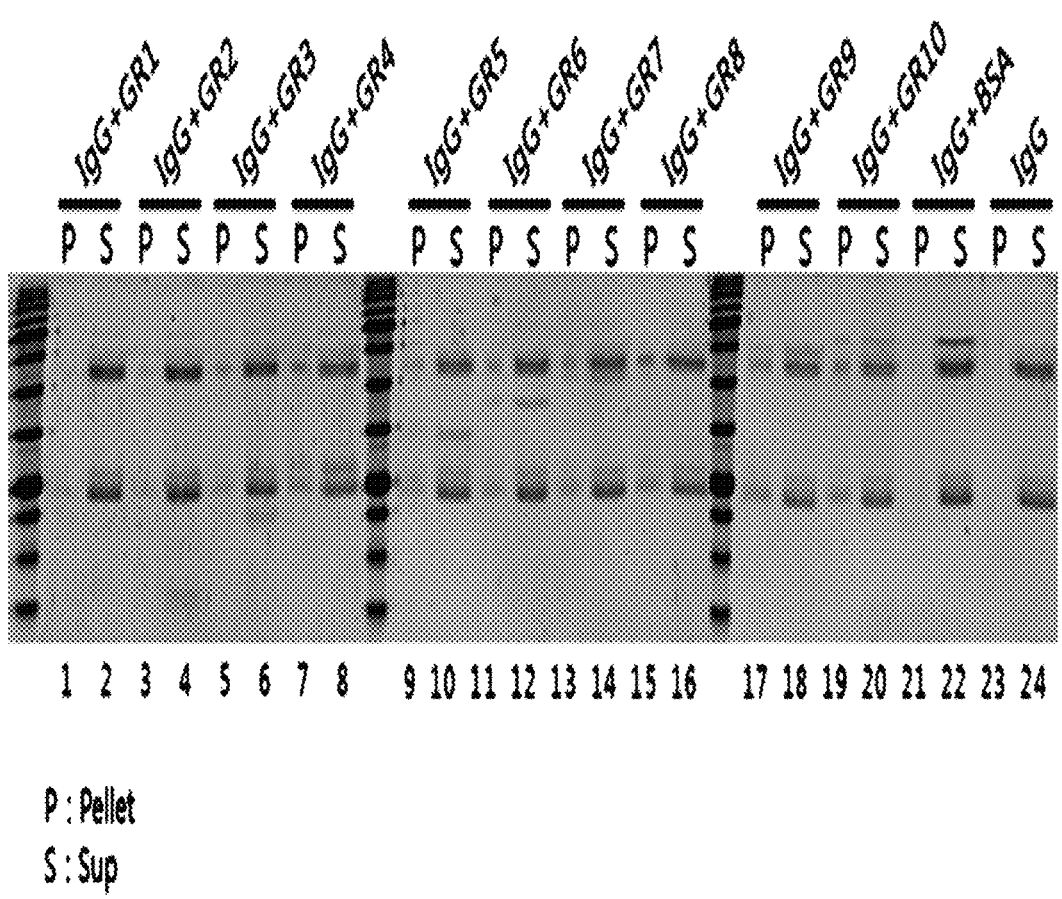
P : Pellet
S : Sup

[Fig. 31]
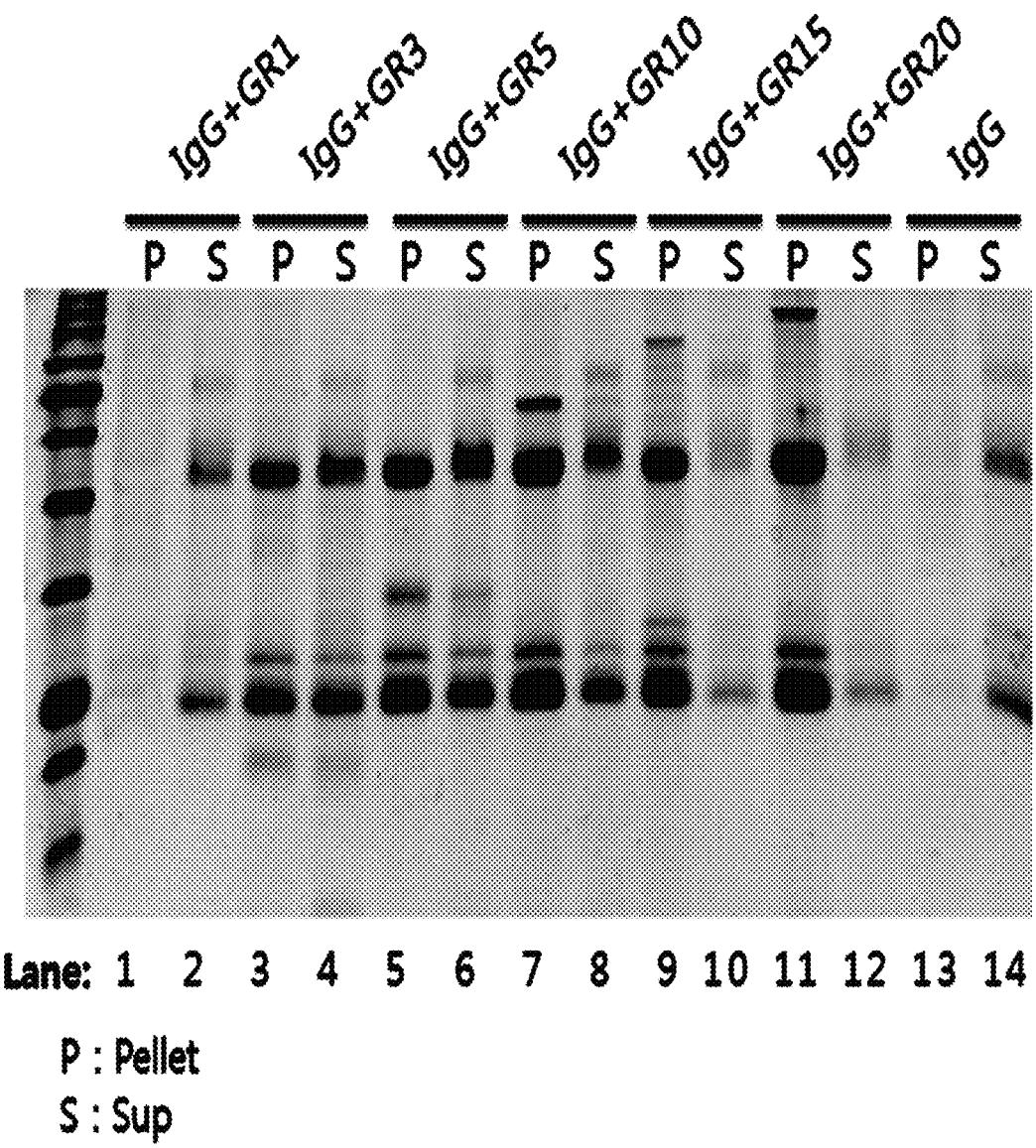
Lane: 1 2 3 4 5 6 7 8 9 10 11 12 13 14
P : Pellet
S : Sup

SEQUENCE LISTING

```
<160> NUMBER OF SEQ ID NOS: 11

<210> SEQ ID NO 1
<211> LENGTH: 49
<212> TYPE: DNA
<213> ORGANISM: Artificial Sequence
<220> FEATURE:
<223> OTHER INFORMATION: P1 primer for domain III of protein G

<400> SEQUENCE: 1
gggcatatgc atcaccatca ccatcacacc ggtacaccag ccgtgacaa          49

<210> SEQ ID NO 2
<211> LENGTH: 45
<212> TYPE: DNA
<213> ORGANISM: Artificial Sequence
<220> FEATURE:
<223> OTHER INFORMATION: P2 Primer for domain III of protein G

<400> SEQUENCE: 2
cccgaattct tatccggacc cgcctccacc ttcagttacc gtaaa              45

<210> SEQ ID NO 3
<211> LENGTH: 261
<212> TYPE: DNA
<213> ORGANISM: Artificial Sequence
<220> FEATURE:
<223> OTHER INFORMATION: Nucleic acid sequence of Protein A Domain B

<400> SEQUENCE: 3
catatgcatc atcatcatca ccacaccggt tctcaagccc caaaagccga caataaattt     60
aataaagagc agcagaacgc gttttatgaa atcttgcatc tgccgaatct gaatgaagaa    120
caacgtaacg gattcattca gagccttaaa gatgatccta gtcagtccgc taacttactc    180
gcagaagcta agaaactgaa tgatgcacag gcgccgaagg gaggggtgg atccggtggt    240 ggcggctccg gataagaatt c                                              261

<210> SEQ ID NO 4
<211> LENGTH: 5
<212> TYPE: PRT
<213> ORGANISM: Artificial Sequence
<220> FEATURE:
<223> OTHER INFORMATION: synthetic peptide linker G4

<400> SEQUENCE: 4

Gly Gly Gly Gly Ser
1               5

<210> SEQ ID NO 5
<211> LENGTH: 315
<212> TYPE: DNA
<213> ORGANISM: Artificial Sequence
<220> FEATURE:
<223> OTHER INFORMATION: Nucleic acid sequence of Protein L Domain B1
```

```
<400> SEQUENCE: 5
catatgcatc accatcacca tcataccggt atcaagttcg ccggtaaaga agaaacgccg     60 gaaaccctg agacagacag tgaagaggaa gtgacaataa aagcaaatct gattttcgcc    120
aacgggtcaa cccagacggc cgaattcaaa gggacatttg aaaaagcaac ttctgaggct    180
tatgcatacg cggacactct gaagaaggat aatggtgaat ataccgtaga tgttgctgat    240
aaaggttata ccctgaatat taaatttgcg ggtggcggcg gcggaagcgg tggcggaggt    300
tccggataag aattc                                                     315

<210> SEQ ID NO 6
<211> LENGTH: 537
<212> TYPE: DNA
<213> ORGANISM: Artificial Sequence
<220> FEATURE:
<223> OTHER INFORMATION: Nucleic acid sequence of Domain B1-Domain B

<400> SEQUENCE: 6
catatgcatc accatcacca tcataccggt atcaagttcg ccggtaaaga agaaacgccg     60 gaaaccctg agacagacag tgaagaggaa gtgacaataa aagcaaatct gattttcgcc    120
aacgggtcaa cccagacggc cgaattcaaa gggacatttg aaaaagcaac ttctgaggct    180
tatgcatacg cggacactct gaagaaggat aatggtgaat ataccgtaga tgttgctgat    240
aaaggttata ccctgaatat taaatttgcg ggtggcggcg gcggaagcgg tggcggaggt    300
tccggttctc aagccccaaa agccgacaat aaatttaata agagcagca gaacgcgttt    360 tatgaaatct tgcatctgcc gaatctgaat gaagaacaac gtaacggatt cattcagagc    420
cttaaagatg atcctagtca gtccgctaac ttactcgcag aagctaagaa actgaatgat    480
gcacaggcgc cgaagggagg gggtggatcc ggtggtggcg gctccggata agaattc      537

<210> SEQ ID NO 7
<211> LENGTH: 4
<212> TYPE: PRT
<213> ORGANISM: Artificial Sequence
<220> FEATURE:
<223> OTHER INFORMATION: synthetic peptide G4

<400> SEQUENCE: 7

Gly Gly Gly Gly
1

<210> SEQ ID NO 8
<211> LENGTH: 10
<212> TYPE: PRT
<213> ORGANISM: Artificial Sequence
<220> FEATURE:
<223> OTHER INFORMATION: synthetic peptide linker

<400> SEQUENCE: 8

Gly Gly Gly Gly Ser Gly Gly Gly Gly Ser
1               5                   10

<210> SEQ ID NO 9
<211> LENGTH: 15
<212> TYPE: PRT
<213> ORGANISM: Artificial Sequence
<220> FEATURE:
<223> OTHER INFORMATION: synthetic peptide linker

<400> SEQUENCE: 9

Gly Gly Gly Gly Ser Gly Gly Gly Gly Ser Gly Gly Gly Gly Ser
```

-continued

```
1               5               10              15

<210> SEQ ID NO 10
<211> LENGTH: 43
<212> TYPE: DNA
<213> ORGANISM: Artificial Sequence
<220> FEATURE:
<223> OTHER INFORMATION: P3 primer for domain III of protein G

<400> SEQUENCE: 10
agacctttac ggtaactcaa accggtggag gcgggtccgg ata                    43

<210> SEQ ID NO 11
<211> LENGTH: 43
<212> TYPE: DNA
<213> ORGANISM: Artificial Sequence
<220> FEATURE:
<223> OTHER INFORMATION: P4 primer for domain III of protein G

<400> SEQUENCE: 11
tatccggacc cgcctccacc ggtttcagtt accgtaaagg tct                    43
```

REPEAT-CHAIN FOR THE PRODUCTION OF DIMER, MULTIMER, MULTIMER COMPLEX AND SUPER-COMPLEX

CROSS REFERENCE TO RELATED APPLICATIONS

This application is a continuation-in-part of U.S. application Ser. No. 13/516,367, filed on Jun. 15, 2012, now abandoned, which is a national stage application under 35 U.S.C. 371 of PCT Application No. PCT/KR2009/007510 having an international filing date of 15 Dec. 2009, which designated the United States, the entire disclosures of which are incorporated herein by reference.

REFERENCE TO SEQUENCE LISTING

This application contains a Sequence Listing submitted as an electronic text file named "Sequence_Listing_ST25.txt", having a size in bytes of 4 kb, and created on May 27, 2013 and amended on Aug. 9, 2013. The information contained in this electronic file is hereby incorporated by reference in its entirety pursuant to 37 CFR § 1.52(e)(5).

BACKGROUND OF THE INVENTION

1. Field of the Invention

The present invention relates to a method for manufacturing dimers and multimers from monomers based on increased yield. To achieve this, multimers in the form of repeat-chain/multiple-monomer complexes are produced by using repeat-chains of affinity domains specifically binding to monomers, and multimers made by inter-monomeric bond bridges are produced by utilizing the fact that inter-monomeric bond bridges are easily formed between monomers within the complexes. That is, the present invention relates to a method for manufacturing large volume of dimers and multimers by maximizing the formation of multimers in the form of repeat-chain/multiple-monomer complexes by using repeat-chains as binding matrix, and by increasing the formation efficiency of producing inter-monomeric bond bridges among monomers within the formed repeat-chain/multiple-monomer complexes.

The present invention relates to a super-complex formed by cross-binding between the repeat-chain/multiple-monomer complexes and a method for amplifying the biological and chemical effects of monomers using the same.

Particularly, repeat-chain/multiple-monomer complexes are produced with containing repeat-chains of binding domain having binding specificity to monomers as active ingredients, and then a super-complex that is an aggregate generated by cross-binding between such complexes is produced. The super-complex contains multiple monomers, so that it can multiply the biological and chemical effect which is not like any other monomer can give to its target, suggesting the amplification of effects of such monomers.

The repeat-chain herein can be prepared in the form of a material or a partial domain of it that has binding affinity to monomers existing in the nature. There is a wide variety of monomers binding to such materials or domains, which are exemplified by ligands, receptors, antibodies, and enzymes, etc. It is expected that the repeat-chain/multiple-monomer complex and the super-complex generated by the said complexes can amplify the effects of monomers. Such monomers can have biological or chemical functional groups linked, conjugated, or fused, and at this time the effect of the functional group might be amplified significantly.

2. Description of the Related Art

Antibody-toxin is produced by fusing toxin to the antibody specifically binding to cancer cells (Pastan I. et al., Annu Rev Med. 58 (2007) 221-237).

Monoclonal antibody (MAb), B3 binds to carbohydrate antigen (LeY) over-expressed on the surface of colon, stomach, ovary, breast, or pulmonary cancer (L. H. Pai, et al., Proc Natl Acad Sci USA 88 (1991) 3358-3362; I. Pastan, et al., Cancer Res. 51 (1991) 3781-3787). PE38 used for fusion protein of antibody-PE38 is one of the derivatives of Psudomonas exotoxin (PE) and is the protein toxin having molecular weight 38 kd when N-terminus of PE is truncated (J. Hwang, et al., Cell. 48 (1987) 129-136; V. K. Chaudhary, et al., J Biol Chem 265 (1990) 16306-16310).

Fab, a fragment having antigen binding part of antibody, includes Fd chain (VH and CH1) and light chain (VL and CL). The Fab used for the fusion protein in the form of Fab antibody-toxin includes Fd chain (VH and CH1) and light chain (VL and CL), too. Fab-toxin has two advantages compared to single chain Fv-toxin (scFv-toxin, wherein Fv is formed as a single chain by linking $V_H$ and $V_L$ with linker and there is no $C_{H1}$ and $C_L$). First, the yield of Fab-toxin is 10 times higher than that of scFv-toxin (J. Buchner, et al., Biotechnology (N Y). 9 (1991) 157-162; J. Buchner, et al., Biotechnology 10 (1992) 682-685). Second, stability of Fab-toxin is improved in plasma of mouse (M. Choe, et al., Cancer Res. 54 (1994) 3460-3467).

It has been reported that divalent Fab-toxin dimers ([Fab-toxin]$_2$) in which two Fab-toxin are linked by inter-monomeric disulfide bond bridges have higher cytotoxicity than monovalent scFv-toxin (S. H. Choi, et al., Bull. Kor. Chem. Soc. 22 (2001) 1361-1365; J. H. Park, et al., Mol Cells 12 (2001) 398-402; M. H. Yoo, et al., J. Microbiol. Biotechnol. 16 (2006) 1097-1103). Disulfide dimers ([Fab-toxin]$_2$) made by inter-monomeric disulfide bond bridge are manufactured by disulfide bond of intra-monomer counterpartless Cysteine (cys) residues from two Fab-toxin monomers. The intra-monomer counterpartless cysteine residues are located between Fab domain and the toxin of Fab-toxin monomers.

Dimeric (divalent) antibody-toxin is the simplest form of multimer and expected to have more advantages than monomeric (monovalent) antibody-toxin. For example, since dimers have two antigen binding domains, dimers have stronger binding force than the affinity of each domain of monomer and thus, dimers have high avidity for binding. Also, since two of toxin domains (biological or chemical functional group) are transferred at the same time to the target cells by dimers, it is possible that antibody-toxin of divalent dimers is able to kill the target cells with higher cytotoxicity than monovalent monomers. Furthermore, Fab-toxin has higher stability than scFv-toxin which often used to produce recombinant antibody-toxin (D. Rothlisberger, et al., J Mol Biol 347 (2005) 773-789).

[B3(Fab)-ext-PE38]$_2$ in which two B3(Fab)-ext-PE38 monomers are linked by inter-monomeric disulfide bond bridge, can be manufactured by fusing Fab domains of monoclonal antibody B3 to PE38 (KR 10-0566091), and it is reported that [B3(Fab)-ext-PE38]$_2$ has 11 times higher cytotoxicity than B3(Fab)-ext-PE38 when tested on CRL-1739 stomach cancer culture cell line (J. H. Park, et al., Mol Cells 12 (2001) 398-402).

Conventionally, dimers bound by inter-monomeric disulfide bond bridge were purified after refolding (S. H. Choi, et al., Bull. Kor. Chem. Soc. 22 (2001) 1361-1365; J. H. Park, et al., Mol Cells 12 (2001) 398-402; M. H. Yoo, et al., J. Microbiol. Biotechnol. 16 (2006) 1097-1103). In previous reported development in connection to refolding process of disulfide bonded dimers, the yield of dimers was about 0.014%-0.25%. During the refolding process, these disulfide dimers were formed by random accessing of intra-monomer counterpartless cysteine residues of two monomers located between Fab domains and PE38. The main produced molecules of refolding processes were Fab-toxin monomers and the yield thereof reached to almost 10%. Considering this, although the yields of disulfide dimers had been increased through the improvements of refolding processes, the yield of dimers were extremely low. Since antibody-toxin monomers (Fab-toxin) does not have self-binding-affinity among themselves, inter-monomeric disulfide bond bridged dimers are created through random collisions between the two intra-monomer counterpartless cysteine residues during the refolding process. That is, collision frequency among the intra-monomer counterpartless cysteine residues of monomers dissolved in refolding buffer solution during the refolding processes is very low and this results the inefficient formation of inter-monomer disulfide bond bridges during the refolding process, and thus the yield of dimmers is extremely low.

As a result, inventors have tried various methods to produce inter-monomer disulfide bonded dimers including methods for producing disulfide dimers by recycling of oxidation-reduction reactions and chemical cross-linker, but with these methods, the yield of dimers could not be greatly improved.

Therefore, in search for a method to produce more dimer, the inventors constructed repeat-chains which are recombinant proteins wherein Fab binding domains of Streptococcal protein G were repeated more than two times, and with using this chain as binding matrix, multimers in the form of complexes, in which multiple monomers are bounded simultaneously to the chains, were produced. In previous studies, it has been reported that the third domain (domain III) of protein G is able to bind to Fab fragment of IgG, and CH1 domain of Fab fragment has high binding affinity toward the domains of protein G (J. P. et al., Nature 359 (1992) 752-754). As comparing to the refolding process, the repeat-chains of the present invention have the following advantages: High binding affinity for antibody-toxin monomer is shown to the domains of the repeat-chains. Since the monomers are attached to the repeat-chains and are in fixed state on the repeat-chain, space allowed for the monomers is quite restricted and monomers cannot move away from each other freely, and accordingly, the local concentration of the monomers is very high in the repeat-chain/multiple monomer complexes created by attaching a plurality of monomers to the repeat-chains. Increased local concentration brings high collision frequency among intra-monomer counterpartless cysteine residues of each monomer antibody-toxin, and it accelerates the disulfide bond formations between monomers. Therefore, it is possible to produce large quantity of inter-monomer disulfide bond bridged dimers. Typical example of same mechanism is the proximity effect in enzyme reaction kinetics, which increases the local concentration and gives high enzyme reaction rate (Nicholas C. Price and Lewis Stevens. Fundamentals of Enzymology, 3rd Ed. Oxford University Press). As a result, the inventors were able to easily manufacture the antibody-toxin multimer complexes by simply mixing the repeat-chains with monomer antibody-toxins, and completed the present invention by confirming that large quantity of $[B3(Fab)\text{-}ext\text{-}PE38]_2$ are produced through oxidation and reduction shuffling reactions within the complexes accelerating inter-monomer disulfide bond bridge formation of cysteine residues between two monomers.

When a monomer is bound to a target in order to detect the target and then gives a detection signal, the strength of such detection signal indicating the effect of the monomer is determined by the concentration of the target material, binding affinity between the target and detection probe, the concentration of the probe, and the signal effect strength of the probe. In general, the probe is in the form of a monomeric molecule and the detection target is a binding target of the monomer, and the measured signal is the effect of the monomer.

Immunochromatographic assay, using antibodies, is also called rapid antigen test, lateral flow test particularly when a sample flow is lateral, or simply strip test. This assay has been widely used to develop many diagnostic kits. Immunochromatographic assay has been used for the diagnosis of drug abuse, blood components, group A streptococcal antigen, *Helicobacter pylori, Mycobacterium tuberculosis*, hepatitis B surface antigen and antibody, Dengue virus, influenza, and parasite (*Plasmodium falciparum* for the diagnosis of malaria). The advantages of using immunochromatographic assay are simplicity in use, quick detection time taking 5~10 minutes at longest, excellent preservation of reagents at room temperature, and inexpensive costs, which make the assay the best and optimum technique for the diagnosis of a variety of diseases.

As a chromogen for immunochromatographic assay, colloidal gold has been widely used, and hence colloidal gold-labeled immunoglobulin has been effectively used for the diagnosis kit of disease. Colloidal gold particles conjugated with immunoglobulin have been used for the direct detection of antigen molecules. Leuvering et al developed gold particle agglutination assay which is also called sol particle immunoassay (SPIA) in 1981, and thereafter they developed a pregnancy diagnostic kit using the same. Since then, membrane assay using gold has been introduced for the detection of bacterial, viral, parasitic, and fungal diseases. In the meantime, rapid antigen test has been established as rapid field diagnostic method characterized by simple and fast detection that can be done in 10~15 minutes. Such rapid antigen test is important because it enables early prevention of human contagious disease and early diagnosis and prevention of animal contagious disease as well.

The problem of rapid antigen diagnostic kit being widely used these days is that the reliable result can only be obtained when the test is done in 2~3 days from the development of acute disease symptoms. For example, in the case of diagnosing viral disease, if the assay is performed 3 days after the symptom is developed, the kit might confirm the result negative because virus is rapidly reduced 3 days after the first expression. In the case that a patient is young, the decrease of the viral concentration in patient sample starts later, which means it is still possible to perform the assay even 5 days after the first symptom. However, when a patient is an adult, the viral concentration decrease rapidly with time, so that the detection has to be done at least in 4~5 days after the symptom has been shown. That is, antigen diagnosis depends on age. The sensitivity of the conventional rapid antigen diagnostic reagents to the sample containing low concentration of antigen is worse than expected. Rapid diagnostic reagents against various influenza viruses have been introduced in the world market. The sensitivity of these products has been continuously improved, but the sensitivity against seasonal disease is 60~83% and the sensitivity against new swine virus is only 40-69%. The diagnosis test was performed with three kits, 'BinaxNow', 'EZ flu A+B' (Becton Dickinson), and 'Quickvue' (Quidel), which are available in the US market, in order to confirm the diagnostic effect thereof. As a result, H1N1 detection rate of BinaxNow was 40% which was the lowest. Quickvue demonstrated 69% H1N1 detection rate, while EZ flu A+B showed 49% detection rate (Centers for Disease Control and Prevention (CDC), Evaluation of rapid influenza diagnostic tests for detection of novel influenza A (H1N1) virus: United States, 2009. Morb Mortal Wkly Rep 2009; 58:826-829).

The reason of such low sensitivity of the conventional rapid antigen diagnostic reagent is that the virus concentration in the infectee except younger patients is not high enough or the virus concentration in the sample taken under non-optimum condition for the detection is not enough. That is, if the antigen concentration in the sample taken from a patient having virus infection is not enough, the disease cannot be diagnosed accurately. Therefore, it is requested to establish a method or a material for the detection of low concentration antigen in a sample.

Previously, the present inventors established a multiple-monomer/repeat-chain complex by using antibody-toxin as monomer and repeat-chains of binding domain having binding specificity to Fab of antibody as a binding matrix (scaffold), and hence the inventors developed a method to improve the yield of bond bridge multimers by accelerating bond bridge formation by increasing local concentration of monomers and collision frequency among monomers (Korean Patent No. 10-1161323). The previous invention of the present inventors related to the method for mass-production of bond bridge multimers by accelerating the formation of bond bridges between monomers by using repeat-chains of binding domain having binding specificity to monomers. However, the method for amplifying the effect of monomer antibody by using repeat-chains of binding domain having binding specificity to monomers for immunoassay has not been reported yet.

The present inventors tried to improve detection sensitivity of low concentration antigen diagnosis. As a result, the inventors confirmed that when repeat-chains of binding domain having binding specificity to antibody monomers were used as signal amplifiers in Western blotting, enzyme-linked immunosorbent assay (ELISA), and RAT (Rapid Antigen Test), it demonstrated high sensitivity at low concentration of antigen. Therefore, the present inventors confirmed that repeat-chains can be effectively used for the antigen detection analysis using an antibody as a probe monomer by maximizing the effect of the probe antibody monomer. In addition to the antibody-antibody binding protein, there are so many applicable pairs of the monomer and the monomer binding molecule in the nature.

SUMMARY OF THE INVENTION

The present invention aims to provide a method for mass-producing multimers from monomers with inter-monomer bond bridges between monomers, with using repeat-chains of monomer-specific affinity domains as binding matrix to attach the multiple monomers and to mass-produce multimer complexes in the form of the repeat-chain/multiple-monomer complexes, and forming the inter-monomer bridge bond between monomers in the repeat-chain/multiple-monomer complexes, and this provides higher and maximized production methods of multimers linked by inter-monomer bond bridges by the increased collision frequency between the intra-monomer counterpart-less cysteine residues in each monomers and subsequently facilitated formation of the inter-monomer disulfide bond bridges between the monomers compared to the low yield conventional method for producing inter-monomer bridge bonded multimers.

In order to achieve the object explained above, the present invention provides a method for preparing multimers, including steps of:
1) preparing repeat-chains of affinity domains binding specifically to monomers; and
2) preparing repeat-chain/multiple-monomer complexes of the repeat-chains and the monomers with mixing the repeat-chains of step 1) and the monomers.

According to the present invention, a method for producing multimers is provided, which includes steps of:
1) preparing repeat-chains of affinity domains binding specifically to monomers;
2) preparing repeat-chain/multiple-monomer complexes of the repeat-chains and the monomers with mixing the repeat-chains of step 1) and the monomers; and
3) after forming inter-monomer bond bridges between the monomers within the repeat-chain/multiple-monomer complexes of step 2), and separating repeat-chains from the complexes in which inter-monomer bond bridges are formed, but not limited thereto.

In an embodiment of this method of dimer formation in which antibody-toxin monomers are linked by disulfide bond bridges, the yield of inter-monomer disulfide bond bridge dimers of the antibody-toxin monomers increased to 200 and more fold of the yield of the conventionally-reported refolding method, and thus the dimer formation yield was increased very high. The dimers produced according to the present invention have higher antigen binding strength, higher cytotoxicity and higher stability than the previously-reported monomer antibody-toxin, and particularly show approximately 11 times higher cytotoxicity to stomach cancer cell line. Therefore, mass production of the dimers can be effectively used for the development of cancer treatment agents.

It is another object of the present invention to provide a super-complex formed by cross-binding between repeat-chain/multiple-monomer complexes containing repeat-chains of binding domain having binding specificity to monomers such as antibodies, receptors signal transmitters, and enzymes, etc. as active ingredients.

It is also an object of the present invention to provide a method for amplifying the effects of monomers by using the super-complex which includes multiple monomers so that the biological and chemical effects on the targets can be increased multiple times.

To achieve the above objects, the present invention provides the following [1]~[13].

[1] The present invention provides a method for preparing repeat-chains for the production of a super-complex, which comprises the step of preparing repeat-chains which contain a single or multiple kinds of monomer-specific binding domains having at least two binding sites for a monomer repeated therein.

[2] The present invention provides a method for preparing repeat-chain/multiple-monomer complexes for the production of a super-complex, which comprises the following steps: 1) preparing repeat-chains which contain a single or multiple kinds of monomer-specific binding domains having at least two binding sites for a monomer repeated therein; and 2) preparing repeat-chain/multiple-monomer complexes by mixing the repeat-chains of step 1) and the monomers having at least two binding sites for the repeat-chains.

[3] The present invention provides a method for preparing a super-complex, which comprises the following steps: 1)

preparing repeat-chains which contain a single or multiple kinds of monomer-specific binding domains having at least two binding sites for a monomer repeated therein; 2) preparing repeat-chain/multiple-monomer complexes by mixing the repeat-chains of step 1) and the monomers having at least two binding sites for the repeat-chains; and 3) preparing super-complexes in forms of aggregates of the complexes by forming cross-binding between the repeat-chain/multiple monomer complexes of step 2).

[4] The present invention provides repeat-chains prepared by the method of the above [1].

[5] The present invention provides repeat-chain/multiple-monomer complexes prepared by the method of the above [2].

[6] The present invention provides a super-complex prepared by the method of the above [3].

[7] The present invention provides a method for amplifying the effects of monomers, which comprises the step of preparing a super-complex binding to the target of the monomer by mixing the repeat-chain of [4], the repeat-chain-monomer complex of [5], or the super-complex of [6] with the target of the monomer.

[8] The present invention provides the kit for biochemical action, detection, analysis, diagnosis, and treatment which comprises the monomer having at least two binding sites for the repeat-chain and specificity to a biochemical target or a detection target, and the repeat-chains of binding domain having binding specificity to the said monomer.

[9] The present invention provides a method for preparing repeat-chain-biological and chemical effector group, which comprises the step of linking, conjugating, or fusing biological and chemical effector group or detection functional group to repeat-chains of binding domain having binding specificity to monomers.

[10] The present invention provides a method for preparing multiple-monomer/repeat-chain-biological and chemical effector group complex, which comprises the following steps: 1) preparing repeat-chain-biological and chemical effector group by linking, conjugating, or fusing the biological and chemical effector group to repeat-chain of binding domain having binding specificity to monomers; and 2) mixing the monomers to the repeat-chain-biological and chemical effector group of step 1).

[11] The present invention provides the repeat-chain-biological and chemical effector group of monomer binding domain prepared by the method of [9].

[12] The present invention provides the multiple-monomer/repeat-chain-biological and chemical effector group complex prepared by the method of [10].

[13] The present invention provides a method for biological and chemical action, detection, analysis, diagnosis, and treatment on the target of monomer, which comprises the step of forming a super-complex by mixing the multiple-monomer/repeat-chain-biological and chemical effector group complex of [12] with the target of monomer.

This invention can be applied to the antibody toxin (immunotoxin) therapeutics, and it makes the curing of the cancer possible by delivering the super-complexes of antibody-toxin to the cancer target cell. The super-complex of antibody-toxin has very high curing drug efficacies due to the high multiplicities of monomer antibody-toxin, and it still binds to the target maintaining the same specificity to the target. If the binding is one antibody of a super-complex to one antigen the binding strength is the same, and if the binding is multiple antibodies in one complex to multiple antigen the binding strength is multiplied to give very strong binding with maintaining the same specificity The complexes formed through the association of multiple monomers and repeat-chain can make insoluble super-complex aggregates by cross-binding between the complexes and precipitates at high concentration. At low concentration the super-complexes do not have high chance to form bigger super-complex and they do not form precipitating aggregates. The size of the super-complex has small to large size distributions, and the distributions depend on the concentration of the monomers and repeat-chain, and it also depend on the incubation time of monomer with repeat chain. At low concentration the small size super-complexes are dominant in population and they are soluble and do not precipitate.

The aggregation and the precipitation, and the size of the super-complex are also dependent on the structure of monomer and repeat-chain. The number of the repeat of the binding domain in the repeat-chain influences the chain of cross-binding between the complexes, and the solubility and molecular size of the monomer also affect the chance of cross-binding between the complexes.

BRIEF DESCRIPTION OF THE DRAWINGS

FIG. 1 presents outline of a method for producing multimers with bond bridges according to the present invention;

FIG. 2 presents the result of the experiments in which the purified proteins of the present invention are confirmed with SDS-polyacrylamide gel, in which:

FIG. 2A presents the result of the experiments in which recombinant repeat-chain proteins of protein G are mixed with SDS-PAGE sample buffer solution, and the mixture is analyzed in reducing 16% SDS-Polyacrylamide gel, wherein the lanes of No. 1 to 7 are TR1~TR7 respectively (In this specification, GR is also used instead of TR to indicate that it is from protein G.); and FIG. 2B presents the result of analyzing B3(Fab)-ext-PE38(Monomer) and [B3(Fab)-ext-PE38]2(Dimer) antibody-toxin molecules, produced according to the present invention, in non-reducing 8% SDS-Polyacrylamide gel, in which each arrow indicates [B3(Fab)-ext-PE38]2, B3(Fab)-ext-PE38 and B3(Fd)-ext-PE38 from the top (Since (H6-B3(L) has very small molecular weight (i.e., about 25 kDa), this cannot be seen in the drawings); and FIG. 3 presents the result of analyzing the [B3(Fab)-ext-PE38]2 that were formed in the complexes of B3(Fab)-ext-PE38 and TR1~TR7 proteins (In this specification, GR is also used instead of TR to indicate that it is from protein G.), by SDS-Polyacrylamide gel, in which:

FIG. 3A presents the result obtained after steps of: binding protein complex samples (10 g each) to metal chelating agarose bead (lane 1); reducing the samples with 40 mM of 2-Mercaptoethanol at room temperature for 30 min (lane 2); oxidizing the protein complex with 5 mM of oxidized Glutathione form GSSG, for 2 hours at 37° C. (lane 3); and separating ½ of the sample with non-reducing 8% SDS-Polyacrylamide gel, in which the closed arrows each indicate [B3(Fab)-ext-PE38]2, B3(Fab)-ext-PE38 and B3(Fd)-ext-PE38 from the top) The open arrows indicate TR proteins (In this specification, GR is also used instead of TR to indicate that it is from protein G.) from complex; and FIG. 3B presents the result of separating the rest ½ of the sample with reducing 12% SDS-Polyacrylamide gel, in which the two arrows indicate B3(Fd)-ext-PE38 (upper) and H6-B3(L) (bottom). The arrowheads indicate TR proteins (In this specification, GR is also used instead of TR to indicate that it is from protein G.) from complexes (TR1 protein (8 kDa of molecular weight) does not appear in the drawing since the size of TR1 proteins is too small).

Figure 10:
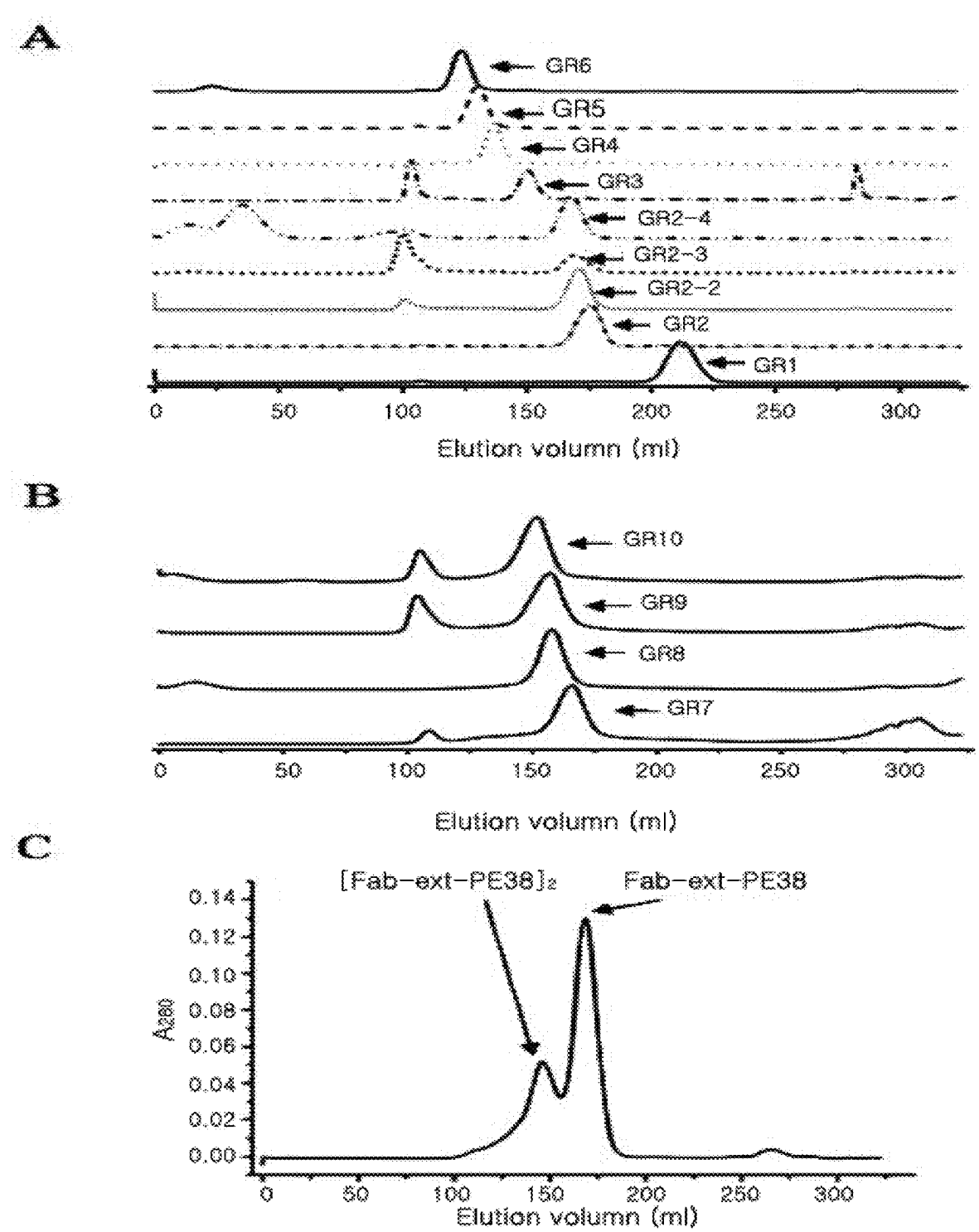

FIG. 4 is the schematic diagrams of expression plasmids constructions of GR1~10.

A: Using pGR1 as vector, pGR2 to pGR10 were made. Same method was used to construct up to pGR20. Each plasmid has one G4S linker between D(III) domains.

B: pGR2-2, 2-3, 2-4 series have two, three, and four G4S linker between two D(III) domains.

FIG. 5 shows the results of SDS-PAGE of purified repeat-chains of domain III of Protein G. The repeat-chain proteins were analyzed on 16% SDS-PAGE. From lane 1 to 13, the samples are GR1, GR2, GR2-2, GR2-3, GR2-4, GR3, GR4, GR5, GR6, GR7, GR8, GR9, and GR10.

FIG. 6 shows the results of size-exclusion chromatography of the GR complexes.

Two vertical arrow indicate the peak of disulfide-dimer (left), [Fab-ext-PE38]2 and monomer (right), Fab-ext-PE38, respectively. Right panel shows the comparison of apparent molecular weight of GR complexes. The apparent molecular weight of monomer (■) and disulfide-bridged dimer (●) are indicated. The schematic diagram represents the complex of Fab-ext-PE38 with GR3 or GR7.

FIG. 7 shows the results of size-exclusion chromatography of the complexes with GR2-2, -3, -4.

A: The size-exclusion chromatography. Two vertical arrows indicate the peak of [Fab-ext-PE38]2 (left) and Fab-ext-PE38 (right).

B: Elution profiles of size-exclusion chromatography of Fab-ext-PE38 associated with GR2-2, -3, and -4. The fractions were electrophoresed in non-reducing 8% polyacrylamide gel. The fractions from 9 to 15.5 ml of the elution volume were analyzed. The arrow indicates [Fab-ext-PE38]2. The arrowheads indicate Fab-ext-PE38.

C: The fractions were electrophoresed with reducing 12% polyacrylamide gel. The arrows, arrowheads, and open arrows indicate Fd-ext-PE38, H6-L, and GR proteins, respectively.

FIG. 8 shows the results of analysis on the mixture of [Fab-ext-PE38]2 and Fab-ext-PE38 complexed with GR2 or GR3.

A: Size-exclusion chromatography. 395 μg of the mixture of [Fab-ext-PE38]2 and Fab-ext-PE38 was associated with GR2 and GR3 proteins. 15 μg of GR protein was used. Vertical arrows and number indicate peak positions.

B: SDS-PAGE of eluted fractions. The mixture of [Fab-ext-PE38]2 and [Fab-ext-PE38] was used as a control. Non-reducing 8% polyacrylamide gel electrophoresis was performed. The elution fractions were compared according to the same fraction numbers from 13 to 26, which have the elution volume from 7 to 12.5 ml. The arrow and open arrow indicate [Fab-ext-PE38]2 and Fab-ext-PE38.

FIG. 9 shows the results of comparison of size-exclusion chromatograms of mixtures of Fab-PE38 monomer and GR2-2, 2-3, 2-4 proteins. Vertical arrows indicates Fab-PE38 monomer (right) and disulfide-dimer (left) as a control. Overlapped chromatograms are associated Fab-monomer with GR2-2 to GR2-4 showing the complex has two Fab-PE38 monomers, dimeric form of monomer on repeat-chain.

FIG. 10 shows the results of size-exclusion chromatography for the purification of the complexes of GR constructs and Fab-PE38 monomer.

A: For the purification of GR1~6, Hiload superdex-75 pg (26/60) column was used.

B: For the purification of GR7~10, Hiload superdex-200 pg (26/60) column was used.

C: For the final purification of Fab-PE38 monomer and disulfide bridged dimer, Hiload superdex-200 pg (26/60) column was used.

FIG. 11 shows the results of disulfide-bridged-dimer formation of Fab-toxin monomer by redox shuffling in the complex of Fab-toxin monomer with GR10, GR2-2, GR2-3 and GR2-4.

Lane 1: starting Fab-toxin monomer.

Lane 2: reduction with 40 mM 2-mercaptoethanol for 30 minute at RT.

Lane 3: oxidation with 5 mM glutathione oxidized form (GSSG) for 2 hours at 37° C. Arrows from top to bottom indicate disulfide-bridged-dimer that was formed by the redox shuffling reaction, Fab-toxin monomer, and Fd chain, respectively.

FIG. 12 shows the result of the amplification of chemi-luminescence signal by GR10 repeat-chain with conventional Western blotting reagents:

Lane A: 20 μg of A431 whole cell lysate (WCL);
Lane 1: 2 μg of A431 WCL;
Lane 2: 1 μg of A431 WCL;
Lane 3: 0.5 μg of A431 WCL; and GR10 treated Western blot gives 32 fold higher signal than that of Conventional Western blot.

FIG. 13 shows that Chemiluminescence signal of western blot was enhanced by GR10 repeat-chain.

FIG. 14 shows that GR10 significantly enhances the sensitivity of ELISA.

a: 1 g of AGS cell lysate was coated each well. The primary antibody was serially diluted.

b: The fold increase in A450 was calculated based on the absorbance of sample of primary antibody alone treated and plotted versus the molar ratio used for making the super-complex for each primary antibody dilution factors.

c: With fixed primary antibody dilution factor, 1:120, the AGS cell lysate was serially diluted and coated to the 96 well plate.

d: The fold increase in A450 was calculated based on the absorbance of sample of primary antibody alone treated and plotted versus the molar ratio used for making the super-complex for each lysate amount coated on the plate.

FIG. 15 shows the serial dilution of secondary antibody and signal amplification. It is shown that primary antibody and GR10 complex significantly increase the signal of ELISA and is rather consistent in the tested range of secondary antibody dilution.

FIG. 16 shows the signal amplification in rapid antigen test kit by GR10.

FIG. 17 shows Immuno-fluorescence probing of the human squamous carcinoma A431 cell with GR1-FITC.

FIG. 18 shows the Cross binding of gold antibody and test line antibody by GR series.

FIG. 19 shows the Cross binding of gold antibody and test line antibody by AR, LR, LAR series.

FIG. 20 shows the signal amplification in rapid antigen test kit by GR5

FIG. 21 shows the signal amplification in rapid antigen test kit by GR10

FIG. 22 shows the signal amplification in rapid antigen test kit by GR15

FIG. 23 shows the signal amplification in rapid antigen test kit by GR20

FIG. 24 shows the signal amplification in rapid antigen test kit by AR5

FIG. 25 shows the signal amplification in rapid antigen test kit by LR5

FIG. 26 shows the signal amplification in rapid antigen test kit by LAR3

FIG. 27 shows the result that insoluble precipitation is made by forming super-complex between GR10 and IgG. The molar ratios of IgG and GR10 were 1:1, 5:1 and 10:1 from left.

FIG. 28 is the SDS-PAGE result that shows that GR10 can make precipitation by super-complex much better than GR1 or GR2. 1/36 of each sample is loaded on a non-reducing 15% SDS-polyacrylamide gel. Lane 1 is the pellet from GR10+ IgG, and lane 2 is the supernatant of GR10+IgG. From lane 3 to 6 are the pellets and supernatants of GR1, GR2 with IgG. Lanes 7 to 10 are the pellet and supernatant of BSA+IgG and IgG only as controls.

FIG. 29 shows the precipitations of GR1 to GR10 mixed with IgG. The controls are BSA+IgG and IgG alone. Samples were incubated at room temperature and centrifuged at 13000 rpm, 20° C. for 30 minutes. In inverted micro-centrifuge tubes, precipitate pellets could be observed as white spots. The circles indicate pellets.

FIG. 30 is the SDS-PAGE result that shows precipitation between GR and IgG. From lane 1 to 20 are the pellets and supernatants of GR1~10 mixed with IgG. Lanes 21, 22 are the pellet and supernatant of control BSA+IgG, and lane 23, 24 are those of IgG alone. 1/30 of each sample was loaded on reducing 15% SDS-polyacrylamide gels.

FIG. 31 shows the result that GR bigger than GR10 also make precipitation. On SDS-PAGE 1/10 of each sample was loaded on reducing 15% SDS-polyacrylamide gels. Lanes from 1 to 12 are the pellets and supernatants of GR1, 3, 5, 10, 15, 20 mixed with IgG. The control lane 13 and 14 are the pellet and supernatant of IgG alone.

DESCRIPTION OF THE PREFERRED EMBODIMENTS

Features and advantages of the present invention will be more clearly understood by the following detailed description of the present preferred embodiments by reference to the accompanying drawings. It is first noted that terms or words used herein should be construed as meanings or concepts corresponding with the technical spirit of the present invention, based on the principle that the inventor can appropriately define the concepts of the terms to best describe his own invention. Also, it should be understood that detailed descriptions of well-known functions and structures related to the present invention will be omitted so as not to unnecessarily obscure the important point of the present invention.

Hereinafter, the terms used in this invention are described.

The term "binding domain repeat-chain" used in this invention indicates a recombinant protein or a material produced by repeating the region having binding specificity to monomers such as antibody. The region having binding specificity indicates the binding domain and in the case that the binding domain is from a natural protein it is a part of the protein that binds to monomer specifically.

The term "antibody monomer" used in this invention indicates a molecule originated from an antibody, which includes a fragment of an antibody and molecules fused with other proteins or biological-chemical functional molecules. When this molecule is mixed or contacted with repeated chains, it is called "antibody monomer". The natural antibody has two heavy chains and two light chains. Considering a set of a heavy chain and a light chain as a unit, the natural antibody is a dimer. However, in this invention, when the natural antibody is mixed or contacted with repeated chains, it is called antibody monomer.

The term "multiple-antibody-monomer/repeat-chain complex" used in this invention indicates a complex prepared by mixing or contacting the said antibody monomer with the repeat-chains of binding domain that bind specifically to the said antibody monomer.

The term "super-complex of multiple-antibody-monomer/repeat-chain complexes" used in this invention indicates a super-complex prepared by cross-binding among the complexes produced by mixing or contacting the antibody monomer with the repeat-chains of binding domain that bind specifically to the said antibody monomer.

In addition, the term "antigen/multiple-antibody-monomer/repeat-chain complex" used in this invention indicates the complex prepared by mixing or contacting the said multiple-antibody-monomer/repeat-chain complex with antigen.

In addition, the term "super-complex of antigen/multiple-antibody-monomer/repeat-chain complexes" used in this invention indicates the super-complex prepared by mixing or contacting the super-complex formed by cross-binding among the multiple-antibody-monomer/repeat-chain complexes with antigen or by preparing mixture of antigen and repeat-chain first and mixing or contacting the mixture of antigen and repeat-chain with the antibody monomer.

Hereinafter, the present invention is described in detail.

The present invention relates to a method for manufacturing multimers by making repeat-chains comprising repeatedly linked affinity domains binding specifically to monomers, and by using the same to create a repeat-chain/multiple-monomer complex created from the repeat-chains and a multiple number of monomers, thereby facilitating the formation of bond bridges between the monomers in the complex to produce inter-monomeric bond bridged multimer.

The present invention relates to a method for manufacturing multimers by making repeat-chain recombinant proteins resulting from the repeated linking affinity domain proteins binding specifically to protein monomers, and by using the same to create a repeat-chain/multiple-monomer complex created from the repeat-chains and a multiple number of monomers, thereby facilitating the formation of bond bridges between the monomers in the complex to produce inter-monomeric bond bridged multimer.

More specifically, the present invention relates to a method for manufacturing multimers by making a repeat-chain recombinant proteins resulting from the repeated linking affinity protein domains binding specifically to protein monomers, and by using the same to create a repeat-chain/multiple-monomer complex created from the repeat-chains and multiple number of monomers, thereby facilitating the formation of disulfide bond bridges between the monomers in the complex to produce inter-monomeric disulfide bond bridged multimer.

More specifically, it relates to a method for manufacturing dimers and multimers by creating repeat-chain recombinant proteins resulting from the repeated linking of the domain III (the Fab binding domain) of Streptococcal protein G, and by using the same as binding matrix (scaffold, skeleton) to create a repeat-chain/multiple-monomer complex created from the repeat-chains and multiple number of monomers derived from antibody, thereby facilitating the formation of disulfide bond bridges between the monomers in the complex to produce inter-monomeric disulfide bond bridged multimer.

The method of the present invention can be used to advantage in the large-volume manufacture of disulfide bond bridge dimers since it gives up to a 200 fold improvement in the yield of disulfide bond bridge dimers as compared with known refolding methods of the prior art.

The present invention aims to produce large quantity of multimers formed by inter-monomer bond bridges and to provide a method for enhancing yield of bond bridged multimers by using repeat-chains of affinity domains binding specifically to monomers as binding matrix, and producing complexes of repeat-chain and multiple numbers of monomers, thereby, increasing local concentration of the monomers on the chains of the complexes, increasing frequency of collision between the monomers and facilitating formation of inter-monomeric bond bridges.

While bond bridged multimers are produced by linking multiple monomers with inter-monomeric bond bridges, the amount of produced bond bridged multimers depends on how efficient the formation of bond bridges is. For the substance to be used in vivo, the bridge bonds for forming multimers are preferred to be covalent bonds so that the multimers are not decomposed into monomers and the stability of multimers is maintained in vivo. In order for covalent bond bridges to be formed, the contact among the bridge bond forming chemical functional groups is required. However, the size of the chemical functional groups in protein is extremely smaller compared to the total size of protein macromolecule. Accordingly, when the macromolecules are moving freely in reaction solution, the probability of small chemical functional groups contacting each other is very low and mass formation of multimers linked with inter-monomer bond bridges is hardly possible unless there is a method for greatly increasing the contact of the functional groups.

In order to increase the formation of bond bridges between monomers, the present invention creates repeat-chains of affinity domains binding specifically to monomers and binds multiple monomers to the repeat-chains making the distance between monomers within several nanometers, or tens of nanometers or hundreds of nanometers, which is the scale of molecular size. Therefore, the monomers bound to the repeat-chain cannot freely move away from each other into the solution. That is, the monomers are fixed in the limited space and contact each other moving in the monomer molecule sized space. Under this condition, local concentration of monomers is extremely high on each repeat-chain to which multiple monomers are bound. Therefore, the frequency of contact between bound monomers is remarkably increased and the frequency of contact between chemical functional groups which can form bond bridges is also increased. Therefore, the formation of multimers is remarkably increased.

The target of the present invention may include not only disulfide covalent bond bridges linking the proteins, but covalent bonds including amide bond, ester bond, glycosidic bond, or ether bond, linking the monomers of organic compounds, bio-molecules or proteins, or any other compounds. The covalent bond bridge may be the most preferable bond bridge to increase stability of multimers, but not limited thereto. That is, the concept of the present invention may still be applied when the multimers are formed with bond bridges such as ionic bond. In addition, the concept of the present invention may be applied for improving formation efficiency of linker connected monomers, as in the case where the dimers or multimers are formed by inserting linker chains between monomers to form bridges between monomers producing a monomer-linker-monomer structure (Greg T. Hermanson, Bioconjugate Techniques. Academic Press, Inc., 1995; Wong S. S., Chemistry of Protein Conjugation and Cross-Linking. CRC Press, Inc., 1991.)

More specifically, a method according to the present invention to produce multimers may preferably include the following step 1) to step 2) of, but not limited thereto:

1) preparing repeat-chains of affinity domains binding specifically to monomers; and 2) preparing repeat-chain/multiple-monomer complexes of the repeat-chains and monomers with mixing the repeat-chains of step 1) and monomers.

Further, the method according to the present invention may additionally include:

3) after forming inter-monomer bond bridges between the monomers within the repeat-chain/multiple-monomer complexes of step 2), and separating repeat-chains from the complexes in which inter-monomer bond bridges are formed, but not limited thereto.

According to the method, the monomers and the affinity domains binding specifically to monomers of step 1) may preferably be originated from protein, but not limited thereto. That is, all kinds of molecules having specific binding affinity there between may be used as the monomers and the affinity domains. For example, protein and small organic compound having specific binding affinity thereto may be used as the monomers and the affinity domains for a method according to the present invention.

According to the method explained above, the preparations of repeat-chains of affinity domains binding specifically to monomers (step 1) may include preparing repeat-chains of different kinds of affinity domains specifically binding to different kinds of monomers together on the same chain and using the repeat-chains as binding matrix. Accordingly, hetero-dimer and hetero-multimer may be manufactured in which different monomers are specifically bound to different affinity domains.

According to the method explained above, in step 1), protein monomers and the protein domains having specific binding affinity to monomers thereto may preferably be originated from native form of protein, but not limited thereto. That is, if monomers of recombinant protein have specific binding affinity to counterpart affinity domains, the recombinant monomers may be used for producing multimers with bond bridges according to the method of the present invention. DNA fragments encoding gene information of the protein may preferably be manufactured by PCR cloning from chromosomal DNA or from mRNA of organisms expressing the proteins using forward and reverse pair of primer, but not limited thereto.

According to the method explained above, the bond bridges in step 3) may include not only the disulfide covalent bond bridges linking the proteins, but also covalent bonds including amide bond, ester bond, glycosidic bond, or ether bond linking the monomers of organic compounds, bio-molecules or proteins. However, this is not limited thereto and multimers may be formed by ionic bond.

According to the method explained above, the repeat-chains of step 1) may be prepared by a method including the following a) to c) steps of, but not limited thereto:

a) preparing construct having repeated binding affinity proteins domains by repeatedly cloning the DNA fragment encoding an affinity domain and an affinity domain connecting linker in an expression vector;

b) preparing transformant by transforming host cell with the construct of step a); and c) cultivating the transformant of step b), and separating and purifying expressed repeat-chain proteins with chromatography, but not limited thereto.

The construct may preferably have a structure in which the affinity domain is repeated over more than 3 times within repeat-chains, but not limited thereto.

Regarding the construct, affinity domain may be linked by linker, and GGGGS (SEQ ID NO:4) may be used as G4S linker, but not limited thereto. The linker may be extended to, for example, GGGGSGGGGS (SEQ ID NO: 8) or GGGGSGGGGSGGGGS (SEQ ID NO:9), but also not limited thereto. The G4S linker has highly flexible structure (R. Arai, et al., Protein Eng 14 (2001) 529-532).

According to the present invention, plasmid pTR1 (In this specification, GR is also used instead of TR to indicate that it is from protein G.) was prepared by cutting DNA fragments encoding affinity domain and linker with NdeI and EcoRI, and cloning the fragments on the vector part of pCW1 cut with the same enzymes.

The DNA fragments encoding affinity domain and G4S linker of pTR1 were cut out again with NdeI and BspEI to separate and purify DNA fragments of 226 bp encoding the DNA fragment of affinity domain and one G4S as a linker thereof, and plasmid pTR2 was prepared by cloning the fragments onto the large vector fragment obtained by cutting the plasmid pTR1 with NdeI and AgeI. The above-mentioned cloning method was repeated 10 times and thus the plasmid having the construct in which affinity domains were repeated 10 times (See Table 1.). The proteins were overexpressed after transforming the *E. coli* BL21 (DE3), and separated and purified with chelating sepharose fast flow chromatography and size-exclusion chromatography.

According to the method, the monomers of step 2) have matrix binding sequence (MBS), the site specifically binding to the affinity domain binding matrix. When the monomers have an binding target, monomers have target binding sequence (TBS) for the target and the target substance of monomers may be used to prepare affinity domain repeat-chains, in this case, target binding sequence (TBS) and matrix binding sequence (MBS) of monomers are the same one. Also, when affinity domain repeat-chains are prepared by non-target substance of monomers which is specifically binding to monomers, but not to target binding sequence (TBS) of the monomers and used to make binding matrix, the matrix binding sequence (MBS) of monomers is different from the target binding sequence (TBS) and the monomers have matrix binding sequence (MBS) and target binding sequence (TBS) separately.

Regarding the formation of repeat-chains-multiple monomers complex of step 2), it is possible to manufacture hetero-dimer and hetero-multimer made of different monomers each specifically binding to each different affinity domains by using repeat-chains of affinity domains having different binding specificity on the same chain.

According to the method, inter-monomer counterpartless cysteine is preferably necessary to manufacture disulfide bond bridged multimers from a complex of multiple monomers of step 2), but not limited thereto. That is, various kinds of chemical bonds and chemical cross-linker may be used for bond bridges between monomers as well as disulfide bond bridges between the counterpartless cysteines on monomers. If the monomer has any counterpartless cysteine for bond bridge, one counterpartless cysteine is preferably included therein, but not limited thereto.

According to the method, the monomers of step 2) may be used to make new kind of monomers by linking the monomers to functional proteins (i.e., functional group, F) with extension sequence (Ext).

According to the method, functional group (F) may include all of biological and chemical compound such as enzyme, toxin functional group protein or virus, pharmaceutical compound for drug activity, functional group (F) such as liposomes, biosensor or prodrug.

The extension sequence (Ext) links monomers and functional group proteins (F) to fuse monomers and functional group proteins and the extension sequence (Ext) may include counterpartless cysteine on monomers, but not limited thereto. The counterpartless cysteine is oxidized between the two monomers and forms disulfide bond bridges; therefore, covalently bonded dimers are formed. Also the extension sequence (Ext) includes flexible amino-acid sequence (Flx) between the last one of counterpartless cysteines on monomers of disulfide bond bridge dimer formation and hetero functional groups (F). The flexible sequence (Flx) is preferably comprised with sequence including GASQEND amino-acids (i.e., glycine, alanine, serine, glutamine, glutamic acid, asparagines and aspartic acid) which is not bulky amino-acid, but not limited thereto.

According to the method, the mixing of step 2) is preferably performed by mixing with the monomers and incubating 3~5° C. overnight and incubating at 35~40° C. for 1~2 hrs. It is more preferable to perform by incubating 4° C. overnight and incubating for 1 hr at 37° C., but not limited thereto.

According to the method, the inter-monomeric bond bridges of step 3) include not only the disulfide covalent bond bridges with protein monomers, but covalent bonds including amide bond, ester bond, glycosidic bond, or ether bond, linked to monomers of organic compounds, biomolecules or proteins. The covalent bond bridge may be the most preferable bond bridge to increase stability of multimers, but not limited thereto. That is, the concept of the present invention may still be applied when the multimers are formed with bond bridges such as ionic bond.

According to the method, regarding the formation of bond bridges, bond bridge-heteromultimer may be manufactured by forming bond bridges between different monomers in a complex of hetero-multiple monomers formed by repeat-chains of affinity domains having different binding specificities on same chain.

According to the method, bond bridges of step 3) may be formed by using the various existing methods (Greg T. Hermanson, Bioconjugate Techniques. Academic Press, Inc., 1995; Wong S. S., Chemistry of Protein Conjugation and Cross-Linking. CRC Press, Inc., 1991.). If disulfide bond bridges are used, the thiol group (—SH) of counterpartless cysteine on monomers is reduced first to be in the —SH form. This reduction is preferably performed by adding the protein complex into reduction buffer solution including 2-merchaptoethanol, but not limited thereto. That is, regarding the reduction, the added amount of 2-merchaptoethanol is preferably 20-40 mM for full reduction of cysteine residues of monomers, but not limited thereto.

According to the method, if disulfide bond bridges are used to form bond bridges of step 3), multimers having disulfide bond bridges are produced by the oxidation of reduced cysteine residues of each of the paired monomer. The oxidation between the monomers is preferably performed by adding reduced protein complex into oxidation buffer solution containing glutathione oxidized form (GSSG), but not limited thereto.

In the present invention, the reduction of protein complex is preferably performed by adding Tris-HCl (pH8.2) in which 2-merchaptoethanol is contained, at room temperature, but not limited thereto. The reduced protein complex is preferably washed with the buffer solution including MOPS (pH6.5), but not limited thereto. The complex is washed 3 times more with Tris-HCl (pH8.2); oxidation buffer solution including GSSG and Tris-HCl (pH8.2) is added thereto for oxidation; and this is incubated at 37° C. for 2 hrs. According to the method, the temperature and time for incubation is preferably 37° C. and for 2 hrs respectively, but not limited thereto.

According to the method, the analysis of bond bridge multimers of step 3) is preferably performed with chromatography, but not limited thereto. All methods which are commonly used for separation and purification of proteins may be used.

According to the method, multimers of step 3) are preferably the dimers in which monomers are linked by disulfide bonds, but not limited thereto. The monomers according to the present invention can be of fusion protein molecule in the form of 'binding domain (B)-extension sequence (Ext)-functional protein (F), (B-Ext-F)', wherein target binding sequence (TBS) and independent matrix binding sequence are existed in the binding domain (B). In case of the extension sequence includes counterpartless cysteine in monomers, disulfide bond bridges are formed between the counterpartless cysteine in monomers of two binding domains (B)-extension sequence (Ext)-functional protein (F) molecules; therefore, the dimers are formed in the form of [binding domain (B)-extension sequence (Ext)-functional proteins (F), (B-Ext-F)]$_2$.

In order to complete the present invention, the inventors used antibody-toxin having Fab protein fragment of antibody as monomer's target binding domain (B) as in the form of 'binding domain (B)-extension sequence (Ext)-functional protein (F)' monomer and domain III (DIII), Streptococcal protein G's Fab binding domain, as affinity domain having specific binding affinity to Fab domain of antibody-toxin. All kinds of the antibody molecules (antibody derived molecule monomers or antibody-functional group fusion molecule monomers) that are originated from antibody and contains Fab fragment of antibody as its part can be used as monomers as well as the ones in antibody-toxin form. In order to maximize the formation of dimers having disulfide bond bridges between monomers ([antibody derived molecule monomer]$_2$), recombinant repeat-chains proteins are prepared wherein Fab binding domains (i.e., domain III) of Streptococcal protein G are repeated over 2 times, and the prepared proteins are used as binding matrix for preparing [antibody derived molecule monomer]$_2$. More specifically, the repeat-chains and antibody derived molecule monomer proteins are mixed to manufacture the multimers in the form of complex of recombinant repeat-chains-antibody derived molecule multiple monomers, in which many antibody monomers are bound to one recombinant repeat-chains protein with non-covalent bonds, and the cysteine residues of antibody monomers are reduced and oxidized to form the disulfide bond of cysteine residues located between Fab fragment and toxin of antibody derived molecule monomer, thus [antibody derived molecule monomers]$_2$ is prepared.

For comparing the formation level of [antibody derived molecule monomers]2 based on the present invention and the one of based on previous refolding method, the inventors of the present invention used SDS-PAGE and analyzed the yield of [antibody derived molecule monomers]2 through measuring the SDS-PAGE band density, and the result was that the yield of [antibody derived molecule monomers]2 based on the present invention is remarkably higher than the reported one performed based on the refolding method. That is, the yield of [antibody derived molecule monomers]$_2$ is in 36 to 52% range of the total antibody derived molecule monomers binding to recombinant repeat-chain proteins wherein Fab binding domain (i.e., domain III) of Streptococcal protein G is repeated over more than 2 times. Accordingly, it is confirmed that the yield range is about 200 and more times higher than the reported yield of existing refolding method.

As a result, it is confirmed that disulfide bond bridge dimers from bound antibody derived molecule monomers may be formed using repeat-chains of Fab binding domain (i.e., domain III) of protein G, and the use of the repeat-chains increases the formation of [antibody derived molecule monomers]$_2$ drastically. By using repeat-chains of Fab binding domains (i.e., domain III) of protein G and its binding specificity to antibody molecule monomers, simple reduction and oxidation can produce large amount of [antibody derived molecule monomers]$_2$.

In the present invention, the repeat-chains having specific binding affinity are characterized to form a repeat-chain/multiple-monomer complex. Therefore, as fixing the repeat-chains on resin, it is possible to perform affinity purification with high efficiency for the purification of useful protein molecules in monomeric or multimeric form in biotechnology and medical industry (Zachariou M., Affinity Chromatography: Methods and Protocols (Methods in Molecular Biology) Humana Press; 2nd edition).

In addition, the present invention provides the gene construct encoding the expression of recombinant repeat-chain protein of affinity domains binding specifically to monomers.

The present invention prepared the gene construct encoding recombinant repeat-chain proteins of domain III (Fab binding domain) of Protein G.

The recombinant repeat-chain proteins preferably include one linker, G4S (GGGGS) (SEQ ID NO:4), between two of Fab binding domains, but not limited thereto.

The recombinant repeat-chain proteins preferably have the structure in which domain III (Fab binding domains) of protein G is repeated 3 to 10 times, but not limited thereto.

Also, the present invention provides expression vector including gene construct.

The expression vector is preferably connected to the desired gene of the specific nucleic acid sequencing having information for controlling gene transcription toward mRNA and translation to proteins to give good expression of desired protein and to increase the possibility of protein formation.

Furthermore, the present invention provides transformant produced by the expression vector in the host cells.

The inducing of the expression vector into host cells is performed by one of appropriate methods including transformation, transfection, conjugation, protoplast fusion, electroporation, calcium phosphate-precipitation or direct microinjection. The host cells may be prokaryotic or eukaryotic cells. Eukaryotic cells are preferable. Eukaryotic cells are the cells of mammals such as CHO cells. These cells are preferably the cell providing correct folding at correct position or transformation for protein molecule including glycosylation after generating the proteins, but not limited thereto.

The present invention confirmed that [antibody derived molecule monomers]2 is able to be produced in large quantity from antibody derived molecule monomers with using recombinant repeat-chain proteins as binding matrix wherein Fab binding domain (i.e., domain III) of Streptococcal protein G is repeated 3 to 10 times within the recombinant repeat-chain proteins.

Accordingly, the repeat-chains of affinity domains having specific binding affinity may be used to improve the formation of dimers and multimers between monomers. Also, gene construct encoding these repeat-chains, expression vector including the gene construct and transformant transformed with the expression vector are very useful for mass formation of bond bridged multimers between antibody derived molecule monomers.

The present invention provides a method for preparing repeat-chains, which comprises the step of preparing repeat-chains which contain a single or multiple kinds of monomer-specific binding domains having at least two binding sites for a monomer repeated therein.

The present invention also provides a method for preparing repeat-chain/multiple-monomer complexes, which comprises the step of preparing repeat-chain/multiple-monomer complexes by mixing the repeat-chains prepared by the above method with multiple monomers.

The present invention also provides a method for preparing a super-complex, which comprises the step of preparing an aggregate of the complexes by cross-binding among the repeat-chain/multiple-monomer complexes prepared by the above method.

In the above method, the said monomer is preferably a protein, which is more preferably selected from the group consisting of antibodies, ligands, receptors or fragments thereof, or recombinants thereof, or derivatives thereof, or fusions of biological or chemical functional group therewith.

In the above method, the antibody is preferably selected from the group consisting of fragments of an antibody, Fab fragment, fragments containing Fab fragment, Fv fragment, fragments containing Fv fragment, Fc fragment, and fragments containing Fc fragment.

In the above method, the binding domain is preferably a protein, and more preferably a microorganism derived protein, and most preferably selected from the group consisting of Streptococcal protein G, *Staphylococcus aureus* protein A, *Peptostreptococcus magnus* protein L, and derivatives thereof.

The repeat-chain of the present invention can include flexible linker chain that helps free rotation of each domain in between repeated binding domains and maintains distance between domains. This prevents binding reaction rate constant and binding reaction equilibrium constant from being reduced because of inter-monomer collision steric hindrance during monomer binding, resulting in the improved binding reaction equilibrium.

The repeat-chain of the binding domain facilitates free rotation of binding domain in the chain and bending of chain as well with the aid of the flexible. Therefore, in the complex formed by mixing repeat-chains with monomers, each binding monomer can have satisfactory rotational freedom and vibrational freedom (bending freedom). That is, the binding monomer has little limitations in the direction of rotation and angles for bending but rotates freely in an enough range of directions and angles to avoid inter-monomer collision. Therefore, it is possible for multiple monomers to bind repeat-chain simultaneously. The flexible linker sequence makes the room between binding domains in repeat-chain large enough so as not to hinder the approaching monomers each other, resulting in the successful simultaneous binding to the repeat-chain. The natural protein that has binding domain usable for repeat-chains of the present invention usually does not have such flexibility in its structures of binding domains. Natural proteins do not allow such freedom in around their binding domains, so that they cannot provide high level rotation freedom and vibrational freedom to the monomers.

The binding domain used in the repeat-chain of the present invention is preferably a fragment of a natural protein molecule, and this fragment has lower molecular weight than a whole natural protein. Making artificial repeat-chain by using such low molecular weight binding domain is advantageous in the construction of repeat-chain that has low molecular weight but has many binding domains, compared with a high molecular weight natural protein molecule. Therefore, multiple monomers can possibly bind to the repeat-chain of low molecular weight. The repeat-chain that has multiple binding domains but has low molecular weight is easy to produce and purify, which is a big advantage that natural protein does not have. In this invention, the repeat-chain that contains up to 20 repeats of binding domain has been constructed, but this invention is not limited thereto.

When the repeat-chain having multiple binding domains but low molecular weight is used, the ratio of monomer to binding molecule (natural microorganism protein molecule, or the repeat-chain of the present invention) is increased, compared with natural molecule, suggesting that the effect of monomer can be amplified significantly per binding molecule. The repeat-chain herein has low molecular weight, so that it can be effectively produced as an artificial protein.

In this invention, when monomer has sites a' and b' therein and binding domain has binding sites for them, a and b, the repeat-chain has to have a and b and the monomer has to have at least one of each a' and b' to form a super-complex of multiple-monomer/repeat-chain complexes by cross-binding between complexes.

In this invention, the monomer is in the form of (a' b'), indicating that a' and b' exist together in one monomer. In the binding domain of repeat-chain, the binding sites a and b can be together in one binding domain to form the repeat-chain having the form of (ab)-(ab)-(ab)----(ab) or the binding sites a and b can be separately in different binding domains to form the repeat-chain having the domain a and domain b repeats in the form of a-b-a-b-a-b----a-b. In that case, the number or the order of the independent (separate) domain a and b is not limited. In addition, when a=b, the monomer is (a' a') and the repeat-chain is (aa)-(aa)-(aa)--- or a-a-a-a-a-a------.

The repeat-chain for the formation of cross-binding between complexes that can make super-complex can be made to have the binding domain c and d that bind to each other and are independent from the binding domain for the multiple-monomer/repeat-chain complex formation. If the chain is constructed to be c-a-a-a-------d, where the monomer binds to domain a, the cross-bindings between the complexes are formed through the binding of c to d, c-a-a-a-----a-d . . . c-a-a-a-----a-d . . . c-a-a-a-----a-d . . . , where . . . indicates the cross-bindings between the repeat-chain, and the super-complexes are formed to give amplification of monomer that are bound to these repeat-chains. The structure of repeat-chain should be rigid enough for the c and d domains in one repeat-chain not to bind to each other. If c and d domains bind each other in one chain the possibility of forming super-complex is very low because there is very low chance for cross-binding between complexes of multiple-monomers/repeat-chain. It is also needed for the repeat-chain not forming c of one chain to d of other chain binding between the chains before mixing with the monomers. If it forms chain to chain binding it is very difficult to handle the molecules and to make complexes with monomers.

The present invention also provides repeat-chains which contain a single or multiple kinds of monomer-specific binding domains having at least two binding sites for a monomer repeated therein.

The present invention also provides repeat-chain/multiple-monomer complexes prepared by mixing multiple monomers to the said repeat-chain.

The present invention also provides a super-complex which is the aggregate of the said complexes generated by cross-binding among the repeat-chain/multiple-monomer complexes.

The said monomer is preferably a protein, which is more preferably selected from the group consisting of antibodies, ligands, receptors or fragments thereof, or recombinants thereof, or derivatives thereof, or fusions of biological or chemical functional group therewith.

The antibody is preferably selected from the group consisting of fragments of an antibody, Fab fragment, fragments containing Fab fragment, Fv fragment, fragments containing Fv fragment, Fc fragment, and fragments containing Fc fragment.

The binding domain is preferably a protein, and more preferably a microorganism derived protein, and most preferably selected from the group consisting of streptococcal protein G, *Staphylococcus aureus* protein A, *Peptostreptococcus magnus* protein L, and derivatives thereof.

The present invention also provides a method for amplifying the effect of monomer, comprising the step of preparing a super-complex by mixing the repeat-chain, the repeat-chain/multiple-monomer complex, or the super-complex thereof to the target of the monomer.

In the above method, the step of measuring the effect of the monomer on the target of the monomer can be additionally included.

In the above method, the target of the monomer is preferably selected from the group consisting of antigens, antibodies, peptides, proteins, bacteria, viruses, fungi, and the fragments thereof but not always limited thereto.

The bacteria herein are preferably selected from the group consisting of *Helicobacter pylori, Mycobacterium tuberculosis*, and *Chlamydia trachomatis*, but not always limited thereto.

The virus herein is preferably selected from the group consisting of influenza, foot and mouth disease virus, human papilloma virus (HPV), Dengue fever virus, hepatitis C virus, and hepatitis B surface antigen and antibody, but not always limited thereto.

In this invention, the measurement of the effect of the monomer is preferably performed by using monomer-marker conjugate or secondary probe (antibody)-marker conjugate, and labeling substrate of the marker, but not always limited thereto.

The super-complex of the present invention gives the opportunity to amplify the effect of the monomer, for example the signal amplification, etc, since it contains multiple monomers suggesting that it bears multiple biological and chemical effects on the target of the monomer, compared with a single monomer.

The present invention also provides an analysis kit containing the multiple monomers having analysis target specificity and at least two binding sites to the repeat-chain in one monomer and the repeat-chains of binding domain having binding specificity to the said monomers.

The said kit is preferably composed of,
1) repeat-chains of binding domain having binding specificity to monomers;
2) monomers binding specifically to the analysis target;
3) secondary probe conjugate labeled with a marker showing label function through the reaction with substrate;
4) marker substrate solution for the reaction with the said marker;
5) washing buffer to be used in each reaction stage; and
6) markering reaction stop buffer, but not always limited thereto.

The kit facilitates the analysis selected from the group consisting of immunohistochemical techniques, immunoblot, immunoprecipitation, enzyme linked immunosorbent assay (ELISA), agglutination, immunochromatographic assay, and radio-immuno assay.

The said marker is preferably selected from the group consisting of horseradish peroxidase (HRP), alkaline phosphatase, colloid gold, fluorescein, Quantum dot, glucose oxidase, luciferase, beta-D-galactosidase, malate dehydrogenase (MDH), acetylcholinesterase, radio-isotope, and dye, but not always limited thereto.

The chromogenic substrate herein is preferably selected from the group consisting of 3,3',5,5'-tetramethyl bezidine (TMB), 2,2'-azino-bis(3-ethylbenzothiazoline-6-sulfonic acid) (ABTS), o-phenylenediamine (OPD), diaminobenzidine (DAB), 3-amino-9-ethylcarbasole, 5-bromo-4-chloro-3-indolyl phosphate/iodonitrotetrazolium (BCIP/INT), new fuchin (NF), and fast red TR salts, but not always limited thereto.

The present invention also provides a method for preparing repeat-chain-detection functional group which has detection functional group added to repeat-chain, containing the step of linking, conjugating, or fusing detection functional group to repeat-chains of monomer-specific binding domains.

The present invention also provides a method for preparing multiple-monomer/repeat-chain-detection functional group complex, comprising the following steps:
1) preparing repeat-chain-detection functional group by linking, conjugating, or fusing detection functional group to repeat-chains of monomer-specific binding domains; and
2) mixing monomers to the repeat-chain-detection functional group prepared in step 1).

The present invention also provides repeat-chain-detection functional group of monomer binding domain prepared by linking, conjugating, or fusing detection functional group to repeat-chains of monomer-specific binding domains.

The present invention also provides multiple-monomer/repeat-chain-detection functional group complex which is prepared by mixing multiple monomers to the repeat-chain-detection functional group of monomer binding domain.

The present invention also provides a method for detecting the target of the monomer, containing the step of forming a super-complex bound to the target of the monomer by mixing the multiple-monomer/repeat-chain-detection functional group complex to the target of the monomer.

In the above method, the step of measuring the detection level of monomer for the target of the monomer can be additionally included.

In the above method, the detection functional group is preferably selected from the group consisting of Cy-3, Cy-5, FITC, GFP (green fluorescent protein), RFP (red fluorescent protein), and Texas Red, but not always limited thereto.

In the above method, if the monomer is an antibody, the antibody is preferably selected from the group consisting of fragments of an antibody, Fab fragment, fragments containing Fab fragment, Fv fragment, fragments containing Fv fragment, Fc fragment, and fragments containing Fc fragment.

Practical and presently preferred embodiments of the present invention are illustrative as shown in the following Examples.

However, it will be appreciated that those skilled in the art, on consideration of this disclosure, may make modifications and improvements within the spirit and scope of the present invention.

<Example 1> Preparation of Repeat-Chains Construct of Fab Binding Domain from Streptococcal Protein G The inventors obtained domain III of protein G from Korean Collection for Type Cultures (KCTC) and performed PCR cloning with P1[5'-GGGCA TATGC ATCAC CATCA CCATC ACACC GGTAC ACCAG CCGTG ACAA-3'(SEQ ID No: 1)] and P2[5'-CCCGA ATTCT TATCC GGACC CGCCT CCACC TTCAG TTACC GTAAA-3'(SEQ ID No:2)] primers from chromosomal DNA of *Streptococcus*. The PCR products (243 bp) were cut with NdeI and EcoRI, and was cloned into vector pCW1 which was cut with the same. The encoding sequence of the domain III was confirmed by dideoxy-DNA sequencing. G4S linker for each domain III was added as spacer and thus, pTR1 was obtained (In this specification, GR is also used instead of TR to indicate that it is from protein G.). The plasmid pTR1 was cut again with NdeI and BspEI and 225 bp fragment encoding domain III and one of G4S was ligated to the large fragment of identical pTR1 plasmid cut with NdeI and AgeI, thus pTR2 encoding the two time Tandem Repeat of domain III was obtained. The plasmid pTR2 was cut with NdeI and AgeI again, and the large fragment was ligated to 226 bp fragment to produce new plasmid 'pTR3'. Using the cloning explained above, plasmid (pTR10) having up to 10 repeats of domain III of protein G was prepared (See Table 1). Based on the existing method, pMC75H encoding H6-B3(L) was prepared (See KR 10-0566091).

TABLE 1

Used plasmids and proteins in the present invention

| Plasmid | Proteins | References |
| --- | --- | --- |
| pCW1 | B3(Fd)-ext-PE38:Fd-SKPSIST-KASG4C(G4S)2GGPE-PE38[a] | J. H. Park, et al., Mol Cells 12(2001) 398-402 |
| pMC75H | H6-B3(L): (His)6[b]-Light chain | The detailed description of the present invention |
| pTR1~10 | TR1~10: (His)6-(DIII-G4S)n, n = 1~10[c] | The detailed description of the present invention |

[a]SKPSIST: a mutated sequence of natural-type hinge sequence(CKPCICT); ext: SKPSIST-KASG4C(G4S)2GGPE: extended peptide chains having cysteine residues (Cys residue);
G4S: amino acid sequence of GGGGS (SEQ ID No: 4);
PE38: truncated *Pseudomonas* Exotoxin of 38 kd;
[b](His)6: 6 of Histidine tags; and
[c]DIII: domain III of Streptococcal protein G.

Based on the existing method, the repeat-chains were over-expressed (J. H. Park, et al., Mol Cells 12 (2001) 398-402).

Pure lysate was separated with chelating sepharose fast flow chromatography (Amersham Bioscience, Sweden) and performed size-exclusion chromatography with Hiload Superdex-75 pg or Hiload Superdex-200 pg(26/60 (Amersham Bioscience, Sweden). Proteins of all the constructs were purified over 95% purity (See FIG. 2A).

<Example 2> Preparation of B3(Fab)-ext-PE38 and [B3(Fab)-ext-PE38]$_2$ by Refolding Based on the existing method, the inventors performed over-expression, preparation and refolding of inclusion body of B3(Fd)-ext-PE38 and H6-B3(L) (J. H. Park, et al., Mol Cells 12 (2001) 398-402). The refolded proteins were purified with Q-sepharose FF, Hitrap protein G HP, and Hiload Superdex-200 pg(26/60)(Amersham Bioscience, Sweden) chromatography.

More specifically, B3(Fab)-ext-PE38 was prepared by inter-chain disulfide bond between B3(Fd)-ext-PE38 and H6-B3(L). The two cysteine residues related to inter-chain disulfide bond located one on the end of CH1 domain of B3(Fd)-ext-PE38 and other on the end of CL domain of H6-B3(L). Also, during the refolding process, [B3(Fab)-ext-PE38]2 was also produced by inter-monomeric disulfide bond between two monomers by the intra-monomer counterpartless cysteine residues located on the ext position of B3(Fab)-ext-PE38 monomer. After performing size-exclusion chromatography, 95% purity of B3(Fab)-ext-PE38 and [B3(Fab)-ext-PE38]$_2$ was measured as a result of conducting densitometric analysis of non-reducing SDS-polyacrylamide gel (See FIG. 2B). The conventional refolding yield of [B3(Fab)-ext-PE38]$_2$ was about 0.06%, while the method of the present invention provided 200 times increased yields.

<Example 3> Binding of B3(Fab)-ext-PE38 Monomers with Repeat-Chains Construct from Protein G Domain III For the binding reaction between purified repeat-chain construct of protein G domain III and monomer B3(Fab)-ext-PE38, the inventors mixed B3(Fab)-ext-PE38 (715 μg) and TR proteins (28 μg each) (In this specification, GR is also used instead of TR to indicate that it is from protein G.), warmed the mixture at 4° C. over-night, and then warmed the mixture at 37° C. for 1 hr. The reacting mixture was separated by size-exclusion chromatography (Superdex-200™ HR). The elusion profile of the protein complex was compared to those of B3(Fab)-ext-PE38 only (Kav=0.33) or [B3(Fab)-ext-PE38]2 only (Kav=0.20) as controls. The Kav value of the eluted protein peak was calculated with [Formula 1].

$$Kav = \frac{(Ve - Vo)}{(Vt - Vo)} \qquad [\text{Formula 1}]$$

wherein Ve is elution volume of the peak, Vo is void volume of the column, which is the elution volume of blue dextran 2000; and Vt is bed volume of superdex-200 column.

B3(Fab)-ext-PE38(Kav=0.22) bound to TR3 gave similar elution volume to that of [B3(Fab)-ext-PE38]2. Other complexes had 2 or more of B3(Fab)-ext-PE38 monomer molecules bound simultaneously to TR chains except TR2. TR3 to TR6 complexes were dimers of B3(Fab)-ext-PE38 monomer and TR7~10 complexes were trimers.

<Example 4> Preparation of [B3(Fab)-ext-PE38]$_2$ Dimer from the Complexes of Repeat-Chains of Protein G Domain III and B3(Fab)-ext-PE38 Monomers In order to produce [B3(Fab)-ext-PE38]$_2$ dimer in the complexes of the purified TR1~TR10 chain proteins (In this specification, GR is also used instead of TR to indicate that it is from protein G.) and B3(Fab)-ext-PE38 monomers bound thereto, the inventors performed reduction with 2-Mercaptoethanol, oxidation reactions to the bound monomer molecules on the chains with oxidized form of glutathione (GSSG), and the products were analyzed by non-reducing (FIG. 2A) and reducing (FIG. 2B) SDS-PAGE.

More specifically, The protein complex (10 μg) was mixed with metal-chelating Sepharose beads (20 μl) in a microtube for 1 h at 10° C. The metal-chelating Sepharose beads were in a 50% suspension equilibrated with 100 mM Tris-HCl buffer (pH 8.2). The immobilized protein complex was reduced by the addition of 40 mM 2-merchaptoethanol in 100 mM Tris-HCl buffer (pH 8.2) at room temperature. In a preparatory experiment for deciding the concentration of 2-Merchaptoethanol which was necessary to reduce cysteine residues of B3(Fab)-ext-PE38, it was found that the full reduction of cysteine residues was achieved by adding 20~40 mM of 2-Merchaptoethanol. After the reduction, reduced protein complex was washed 1 time with washing buffer solution including 100 mM of MOPS (pH6.5) and washed 3 times more with 100 mM of TrisHCl (pH8.2). The washed protein complex was oxidized with oxidation buffer solution including 5 mM of GSSG and 100 mM of TrisHCl (pH8.2) and warmed at 37° C. for 2 hrs. After the oxidation, 2×SDS sample buffer solution was added, the product was analyzed and stained with SDS-polyacrylamide gel electrophoresis (SDS-PAGE) and Coomassie. The production rate of [B3(Fab)-ext-PE38]2 was analyzed through densitometry analysis that can measure the amount of protein on the SDS-PAGE samples. Using the data from SDS-PAGE, the yield of dimers in comparison with the total monomers of [B3(Fab)-ext-PE38]2 was calculated with the band intensity of [B3(Fab)-ext-PE38]2 divided by total band intensity which was the sum of the intensity of [B3(Fab)-ext-PE38]2 and B3(Fab)-ext-PE38 (See Table 2.). B3(Fab)-ext-PE38 only and B3(Fab)-ext-PE38 bound to TR1 were used as controls.

TABLE 2

The yield of [B3(Fab)-ext-PE38] 2

| Antibody-toxin complexed with TR chains | The yield (%) |
| --- | --- |
| B3(Fab)-ext-PE38 | N/A |
| B3(Fab)-ext-PE38: TR1 | N/A |
| B3(Fab)-ext-PE38: TR2 | N/A |
| B3(Fab)-ext-PE38: TR3 | 47% ± 0.25 |
| B3(Fab)-ext-PE38: TR4 | 44% ± 0.19 |
| B3(Fab)-ext-PE38: TR5 | 48% ± 0.12 |
| B3(Fab)-ext-PE38: TR6 | 36% ± 0.02 |
| B3(Fab)-ext-PE38: TR7 | 52% ± 0.11 |

In the above experiment result, [B3(Fab)-ext-PE38]2 was not detected in 3 samples (i.e., B3(Fab)-ext-PE38 only, complex with TR1 and complex with TR2). Significant amount of inter-monomeric disulfide bond bridged dimers were produced by the interaction of monomers in the complexes with TR3~TR7 chains. In samples of TR3~TR7 complexes, the yield of [B3(Fab)-ext-PE38]2 was 47%, 44%, 48%, 36% and 52%, respectively. [B3(Fab)-ext-PE38]2 was produced within 2 hrs after the addition of oxidizing agent and no significant increase was observed for extended incubation. It was thus confirmed that cysteine residues in ext sequence of B3(Fab)-ext-PE38 molecule have easier and closer contact to each other via repeat-chains when they are bound to TR chains proteins.

<Example 5> Construction of Protein G IgG-Binding Domain III Repeat-Chain GR8GR20, and GR2-2, -3, -4

We construct the plasmids that has two domain III of protein G with G4S linker up to four times between the two domain III. The DNA sequence for the domain III was obtained from chromosomal DNA of *Streptococcus* (KCTC 3098) received from the Korean Collection for Type Cultures (KCTC), The plasmid that has the domain III sequence, pGR1 (Y. Lee et al, Enhanced Formation of Disulfide-bridged Dimer (Fab-PE38)2 Utilizing Repeats of the Fab Binding Domain of Protein G (2010) J. Biol. Chem. 285, 5127-5131), was used for the site-directed metagenesis to construct pGR1-A that has an additional AgeI restriction site at the end of the coding region of domain III of protein G and at the beginning of G4S sequences.

Both primer 3 [5'-AGACCTTTAC GGTAACTCAA ACCGGTGGAG GCGGGTCCGG ATA-3' (SEQ ID NO: 10)] and primer 4[5'-TATCCGGACC CGCCTCCACC GGTTTCAGTT ACCGTAAAGG TCT-3' (SEQ ID NO:11)] were used for the Quick-change site-directed mutagenesis. After the mutagenesis, the coding sequence of pGR1-A was confirmed by sequence analysis. The plasmid, pGR1-A, was digested by NdeI and BspEI. The small fragment was purified. Also, pGR1 was digested by NdeI and AgeI, where the AgeI site is located after 6His tag. The plasmid, pGR2-A, was constructed by ligation the large fragment of pGR1 that was produced by the digestion of NdeI and AgeI to the small fragment of pGR1-A produced by the digestion of NdeI and BspEI. The digestion of pGR2-A by NdeI and AgeI gives large fragment of plasmid that has the G4S linker in front of domain III. Ligation of this large fragment to the small NdeI and BspEI fragment of pGR1-A, resulted pGR2-2 that has two units of G4S between first and second of domain III of Protein G. Subsequently, the plasmids pGR2-3 and GR2-4 which have three and four units of G4S linker were constructed in the same way that was used for the construction of pGR2-2.

The construction for GR8~20 were done in the same way as in the paper of pGR1 (Y. Lee et al, Enhanced Formation of Disulfide-bridged Dimer (Fab-PE38)2 Utilizing Repeats of the Fab Binding Domain of Protein G (2010) J. Biol. Chem. 285, 5127-5131), and the FIGS. 4A and 4B is the schematic diagrams of expression plasmids constructions of GR1~10.

FIG. 5 shows the results of SDS-PAGE of purified repeat-chains of domain III of Protein G.

<Example 6> Size-Exclusion Chromatography Analysis of the Complexes Formed Between Fab-Toxin Monomer and Protein G Domain III Repeat-Chain GR1~GR10, GR2-2, -3, -4, and the Disulfide-Bridged Dimer Formation in the Complex The immunoglobulin binding domain III of protein G binds both Fc and Fab fragments of IgG. It was reported that the immunoglobulin-binding region (domain III) of protein G can bind to the CH1 of the Fab fragment. Domain III of protein G binds to Fab through an antiparallel alignment of the second β-strand from domain III with the seventh β-strand of CH1 domain of Fab. The β/β interaction between two proteins accounts for five hydrogen bonds between the CH1 domain of Fab fragment and domain III of protein G. A further three hydrogen bounds also involve main atoms from the CH1 domain. There do not appear to be any large changes in conformation of either domain III, or the CH1 domain on formation of the complex between the two proteins.

We construct two different types of the domain III repeat-chain. First type of the constructs has one G4S amino acid between domain IIIs. The repeat-chain that has up to 10 repeats of domain III was used to associate with Fab-PE38 monomer. These repeat-chains are GR1 to GR10. It is expected that multiple number of monomer on the repeat-chain, such as dimer, trimer or tetramer, are formed by association with domain III repeat-chains.

Second, we also construct the proteins that have only two domain III with different length of G4S linkers. It is made to see the differences of complex formation of Fab-PE38 monomer with domain III repeat-chain depending on the length of linker. These repeat-chain are GR2-2, GR2-3, and GR2-4, each having two, three, and four G4S linkers between two domain III. These repeat-chain shows the effect of the length of linker for the formation of the complex of two Fab-PE38 with repeat-chain giving dimeric form of two Fab-PE38 monomers. Using this construct of GR2-2 to GR2-4, non-covalently associated complex could be obtained easily, and complex of dimer of Fab-PE38 monomer with the repeat-chain was confirmed by size exclusion column.

FIG. 6 shows the results of size-exclusion chromatography of the GR complexes. The size-exclusion chromatography was performed with Superdex-200™ HR column. The association of both Fab-ext-PE38 and GR proteins was done with different ratio. 715 µg of Fab-ext-PE38 was associated with each GR protein. From GR1~GR3, Fab-ext-PE38 was associated with GR proteins as a molar ratio of 2:1. From GR4~10, 715 µg of Fab-ext-PE38 was associated with 28 µg of each GR protein. All the chromatogram was aligned and stacked according to the same elution volume. The reference chromatograms of purified [Fab-ext-PE38]2 (D, dimer) and purified Fab-ext-PE38 (M, monomer) eluted with the same condition.

FIG. 7 shows the results of size-exclusion chromatography of the complexes with GR2-2, -3, -4.

FIG. 8 shows the results of analysis on the mixture of [Fab-ext-PE38]2 and Fab-ext-PE38 complexed with GR2 or GR3.

FIG. 9 shows the results of comparison of size-exclusion chromatograms of mixtures of Fab-PE38 monomer and GR2-2, -3, -4 proteins.

FIG. 10 shows the results of size-exclusion chromatography for the purification of the complexes of GR constructs and Fab-PE38 monomer. Proteins were finally purified by size-exclusion chromatography. All the chromatogram was the trace of UV absorption at 280 nm. The chromatograms were aligned according to the same elution volume and stacked with the same interval.

FIG. 11 shows the results of disulfide-bridged-dimer formation of Fab-toxin monomer by redox shuffling in the complex of Fab-toxin monomer with GR10, GR2-2, GR2-3 and GR2-4. The products of the reaction were analyzed on 8% non-reducing SDS-PAGE.

TABLE 3

The calculated fraction of disulfide-bridged dimer formed by redox shuffle reaction of Fab-toxin monomer.

| Antibody-toxin bound to metal chelating bead | action of disulfide dimer |
|---|---|
| B3(Fab)-ext-PE38] | n.d.* |
| B3(Fab)-ext-PE38]:GR1 | n.d.* |
| B3(Fab)-ext-PE38]:GR2 | n.d.* |
| B3(Fab)-ext-PE38]:GR3 | 0.7 |
| B3(Fab)-ext-PE38]:GR4 | 0.5 |
| B3(Fab)-ext-PE38]:GR5 | 0.6 |
| B3(Fab)-ext-PE38]:GR6 | 0.3 |
| B3(Fab)-ext-PE38]:GR7 | 0.6 |
| B3(Fab)-ext-PE38]:GR8 | 0.1 |
| B3(Fab)-ext-PE38]:GR9 | 0.1 |
| B3(Fab)-ext-PE38]:GR10 | 0.3 |
| B3(Fab)-ext-PE38]:GR2-2 | 0.2 |
| B3(Fab)-ext-PE38]:GR2-3 | 0.4 |
| B3(Fab)-ext-PE38]:GR2-4 | 0.3 |

*n.d.: not determined.

<Example 7> Antibody Signal Effect Amplification by Protein G Domain III Repeat-Chain GR10 in Western Blot Analysis Material and Method Western blotting protocol from cell signaling Technology® was used with modification, and modified version of direct ELISA protocol from Abcom® was used.

A. Solutions and Reagents

NOTE: Prepare solutions with Milli-Q or equivalently purified water.

1) 1×SDS Sample Buffer: 62.5 mM Tris-HCl (pH 6.8 at 25° C.), 2% w/v SDS, 10% glycerol, 50 mM DTT, 0.01% w/v bromophenol blue or phenol red.

2) Transfer Buffer: 25 mM Tris base, 0.2 M glycine.

3) 10× Tris Buffered Saline (TBS): To prepare 1 liter of 10×TBS: 24.2 g Tris base, 80 g NaCl; adjust pH to 7.6 with HCl (use at 1×).

4) Chicken egg albumin: (weight to volume [w/v]).

5) Blocking Buffer: 1×TBS, 0.1% Tween-20 with 2% w/v chicken serum albumin.

6) Wash Buffer: 1×TBS, 0.1% Tween-20 (TBS/T).

7) Primary Antibody: mouse anti?beta-actin antibody from Santacruz biotech.

8) Primary Antibody Dilution Buffer: 1×TBS, 0.1% Tween-20 with 2% w/v chicken serum albumin as indicated 9) Secondary Antibody: Goat anti-mouse beta actin-HRP.

10) Blotting Membrane: Nitrocellulose membranes (Wattman), PVDF membranes (PALL).

11) GR recombinant protein. GR10

12) Luminol solution: 100 mM Tris/HCl pH 8.8, 1.25 mM luminol, 2 mM 41PBA, 5.3 mM hydrogenperoxide 13) Super signal femto maximum sensitivity reagent (thermo scientific)

B. Protein Blotting
I. Sample Preparation.

1) A431 or AGS carcinoma cell line was used for preparing the cell lysate.

2) Aspirate media from cultures; wash cells with 1×PBS; aspirate.

3) Lyse cells by adding 1×SDS sample buffer.

4) Heat samples to 95-100° C. for 5 minutes.

5) Microcentrifuge for 5 minutes.

6) Load onto SDS-PAGE gel (10 cm×10 cm).

7) Electrotransfer to nitrocellulose or PVDF membrane.

C. Membrane Blocking and Antibody Incubations

NOTE: Volumes are for 10 cm×10 cm (100 cm2) of membrane; for different sized membranes, adjust volumes accordingly.

I. Membrane Blocking

1) After transfer, wash nitrocellulose or PVDF membrane with appropriate volume of TBS for 5 minutes at room temperature.

2) Incubate membrane in appropriate volume of blocking buffer for one hour at room temperature.

3) Wash three times for 5 minutes each with TBS/T.

II. Super-Complex Preparation.

1) Prepare and incubate GR10 and primary antibody (at the molar ratio as indicated in result) for 1 hr at 37° C.

2) Store on ice and keep the super-complex at 4° C. until use.

III. Primary Antibody Incubation

1) Incubate membrane and primary antibody (at the dilution as indicated in result) in 10 ml primary antibody dilution buffer with gentle agitation for 1 hr at room temperature.

2) Wash three times for 5 minutes each with 15 ml of TBS/T.

3) Incubate membrane with the species appropriate HRP-conjugated secondary antibody (1:2000) in appropriate volume of blocking buffer with gentle agitation for one hour at room temperature.

4) Wash three times for 5 minutes each with 15 ml of TBS/T.

5) Proceed to detection step in section D.

D. Detection of Proteins

1) Incubate membrane with luminol solution prepared or super signal femto maximum sensitivity reagent (thermo scientific) with gentle agitation at room temperature.

2) Drain membrane of excess developing solution (do not let dry), wrap in plastic wrap and expose to x-ray film.

FIG. 12 shows the result of the amplification of chemiluminescence signal by GR10 repeat-chain with conventional Western blotting reagents.

In FIG. 13-a, we observed that the super-complex gave approximately 17-fold higher signal by the complex of monoclonal anti-β-actin mouse antibody and GR10. The complex formation of GR10 and primary antibody was preformed according to the molar ratio, which is indicated in parenthesis. The primary antibody was used at the concentration of 1:1000 dilution, and the super-complex was made at the same concentration of the primary antibody. For secondary antibody, goat anti-mouse-HRP conjugate was used for both experiments. Primary and secondary antibody were incubated for an hour at RT. All the cell lysate samples of the experiment was separated in the same 10% denaturing SDS-PAGE and transferred to nitrocellulose membrane, which is cut into three pieces and probed with primary antibody. Highly sensitive Thermo Supersignal Femto substrate was used.

In FIG. 13-b, A431 clear lysate was separated by 10% denaturing SDS-PAGE and transferred to PVDF membrane to check whether the super-complex shows signal amplification that is comparable to that of nitrocellulose membrane. The membrane was probed by primary antibody alone and secondary antibody with conventional ECL, and instantly washed by TBST and reprobed with Supersignal Femto substrate. We observed the increase of signal and also huge background noise, which is due to nonspecific adsorption of secondary antibody on PVDF membrane and highly sensitive Supersignal Femto substrate. Subsequently, the membrane was stripped by SDS and 2-mercaptoethanol treatment. The stripped membrane was reprobed by the super-complex with conventional ECL. Super-complex increased the sensitivity about 15-fold higher than the conventional method, which is similar increase observed in previous experiment (a) with nitrocellulose membrane. For this experiment we used conventional medium sensitivity chemiluminescence substrate. ECL was prepared by the method of Haan and Behrmann (2007). We could see similar signal amplification as seen on nitrocellulose membrane, and the amplified signal was compatible to that of high sensitivity Supersignal Femto substrate but without background noise increase. Because of higher performance of PVDF membrane, low amount of antigen could be detected with medium sensitivity substrate.

<Example 8> Amplification of Antibody Signal by Protein G Domain III Repeat-Chain GR10 in Enzyme-Linked Immunosorbent Assay Indirect ELISA A. Solutions and Reagents NOTE: Prepare solutions with Milli-Q or equivalently purified water.

1) Bicarbonate/carbonate coating buffer (100 mM) Antigen or antibody should be diluted in coating buffer to immobilize them to the wells: 3.03 g Na2CO3, 6.0 g NaHCO3, 1000 ml distilled water pH 9.6.

2) PBS.

3) Blocking solution: 1% BSA, serum, in PBS.

4) Wash solution: PBS with detergent 0.05% (v/v) Tween20.

5) Antibody dilution buffer: Primary and secondary antibody should be diluted in 1× blocking solution to reduce Non specific binding.

6) Primary Antibody: mouse anti?beta-actin antibody from Santacruz biotech.

7) Secondary Antibody: Goat anti-mouse beta actin-HRP.

8) TR recombinant protein. TR10

B. Coating Antigen to Microplate

1) A431 or AGS carcinoma cell line was used for preparing the cell lysate.

2) Dilute the lysate to a final concentration of 20 μg/ml in carbonate coating buffer.

3) Coat the wells of a microtiter plate with the diluted lysate by pipetting 50 μl of the lysate dilution in the top wells of the plate.

4) Cover the plate with lid and incubate 4° C. overnight.

5) Remove the coating solution and wash the plate twice by filling the wells with 200 μl PBS. The solutions or washes are removed by flicking the plate over a sink. The remaining drops are removed by patting the plate on a paper towel.

C. Blocking

1) Block the remaining protein-binding sites in the coated wells by adding 200 μl blocking buffer, 1% BSA/PBS, per well.

2) Cover the plate with lid and incubate for at least 2 h at room temperature.

3) Wash the plate twice with PBS.

D. Incubation with the Antibody

1) Add 100 μl of the primary antibody or the super-complex, diluted at the indicated concentration in blocking buffer immediately before use.

2) Cover the plate with a lid and incubate for 1 h at room temperature.

3) Wash the plate twice with PBS.

4) Add 100 μl of the secondary antibody-HRP, diluted at the optimal concentration in blocking buffer immediately before use.

5) Cover the plate with a lid and incubate for 1 h at room temperature.

6) Wash the plate trice with PBS.

E. Detection

1) Dispense 100 μl of the TMB substrate solution per well with a multichannel pipet 2) After sufficient color development (30 min) add 100 μl of stop solution to the wells.

3) Read the absorbance (optical density) of each well with a plate reader.

FIG. 14 shows that GR10 significantly enhances the sensitivity of ELISA. In two different ELISA experiments, significant amplification of ELISA signal was observed when the super-complex was used as a primary antibody. AGS cell lysate was incubated overnight at 4° C. in regular cell culture tested 96 well plates and ELISA was done according to the standard procedure. The super-complex was preformed according to the molar ratio, which is indicated in parenthesis. The primary antibody is mouse monoclonal anti-β-actin antibody. For secondary antibody, goat anti-mouse-HRP conjugate was used for both experiments. Primary and secondary antibody were incubated for 1 hour at RT. The substrate, TMB, was incubated for 30 min at RT.

FIG. 15 shows that primary antibody and GR10 complex significantly increase the signal of ELISA and is rather consistent in the tested range of secondary antibody dilution. In this ELISA experiments, significant amplification of ELISA signal was observed when the super-complex of monoclonal anti-β-actin antibody and GR10 was used as a primary antibody. A431 cell lysate was used. The complex of GR10 and primary antibody was made at the molar ratio of 1:10. For secondary antibody, goat anti-mouse-HRP conjugate was used. 1 g of A431 cell lysate was coated each well. The primary antibody was 10-fold serially diluted. With indicated primary antibody dilution factor, the secondary antibody was 2-fold serially diluted.

<Example 9> Sensitivity Enhancement of Influenza Rapid Antigen Test by Protein G Domain III Repeat-Chain GR10

The most common test kit using antibodies, influenza Rapid Antigen Test kits was used to see the amplification of the signal by GR10. Test kits from SD BioLine (SD Inc.) or Green Cross was used. The antigen buffer solution, droppers, tubes, swabs and strips for clinical specimen samples are included in the kit. The antigen buffer was transferred to tube filling the dropper to the indicated amount with the antigen buffer. The swab samples of patients or the antigen sample solution was added to the tube and mixed more than 5 times. The GR10 protein was simply added to the antigen solution in the tube together with the antigen and mixed. After removing the swab, the strip was inserted into the tube, and the results were read after 10 to 15 minutes.

By simply adding GR10 to the commercially available rapid antigen diagnostic kits, the antigen band could be detected until the antigen was 1000 fold more diluted compared the regular test. FIG. 16 shows the signal amplification in rapid antigen test kit by GR10.

<Example 10> The Use of GR Protein as a Labeling Agent to Antibody

Fluoro chromophore fluorescein isothiocyanate was conjugated to GR1 (GR1-FITC) and GR1-FITC was used in immuno-fluorescence probing of the human squamous carcinoma A431 cell. The primary antibody was mouse anti-LC3 antibody, and the prepared GR1-FITC was used instead of secondary antibody. The cells were also probed with Rhodamine-phalloidin (sigma aldrich) for F-actin to compare, and observed under fluorescence microscope.

Very clear fluorescence image of the cell could be obtained with the GR1-FITC conjugate, even though the amount of the GR1-FITC protein used was a lot less than the case of secondary antibody-fluorescence chromophore conjugate. Like GR1-FITC, GR proteins can be linked, conjugated or fused to detection, signal or therapeutic functional group to be used with antibodies, so that each antibody does not need to be conjugated with the functional group. GR proteins has small molecular weight and it is easy to produce and manipulate them. FIG. 17 shows Immuno-fluorescence probing of the human squamous carcinoma A431 cell with GR1-FITC.

<Example 11> Expression Plasmid Construction for Repeat-Chain Protein of Antibody Binding Domain B of *Staphylococcus Aureus* Protein A The plasmid that contains the DNA sequence of Protein A Domain B was synthesized (table 4) and obtained from the Bioneer Corporation. The plasmid was put into *Escherichia coli DH*5a by transformation.

The plasmid was digested with NdeI and BspEI and the small DNA fragment (245 bp) was purified. The small fragment was cloned into the vector fragment of pGR1 (pTR1) obtained by same enzyme digestion, and the plasmid pAR1 that contains one copy of domain B of protein A was obtained. Protein A Domain B Nucleic acid sequence was checked by sequencing analysis of Macrogen corporation The resulting plasmid, pAR1 (table 5) was digested with NdeI and BspEI. The small 245 bp fragment, encoding domain B and two of five amino acid GGGGS(G4S; SEQ ID NO:4) sequence, was ligated with the large fragment of NdeI and AgeI digested pAR1. The resulting plasmid, pAR2, contains two repeat of Protein A Domain B. pAR2 was digested with NdeI and AgeI again, and the large fragment was ligated with the 245 bp fragment to produce a new plasmid, pAR3, that has three time repeat of domain B. Using the same method, plasmids coding up to five repeats of protein A domain B were constructed.

TABLE 4

| Nucleic acid sequence of Protein A Domain B |
|---|
| Nucleic acid sequence of Protein A Domain B |
| (SEQ ID No: 3)<br>5'-CAT<u>ATGCATCATCATCATCACCACACCGGTTCTCAAGCCCCAAA</u><br><u>AGCCGACAATAAATTTAATAAAGAGCAGCAGAACGCGTTTTATGAAA</u><br><u>TCTTGCATCTGCCGAATCTGAATGAAGAACAACGTAACGGATTCATT</u><br><u>CAGAGCCTTAAAGATGATCCTAGTCAGTCCGCTAACTTACTCGCAGA</u><br><u>AGCTAAGAAACTGAATGATGCACAGGCGCCGAAGGGAGGGGGTGGAT</u><br><u>CCGGTGGTGGCGGCTCCGGATAAG</u>AATC-3' |

*under line: coding sequence

TABLE 5

List of plasmids and proteins

| Plamid | Repeat-chain protien | Reference |
|---|---|---|
| pLR1~5 | LR1~5: $(His)_6$-$(B1$-$G_4S$-$G_4S)_n$, $n = 1$~$5.^{a,\ b,\ c.}$ | This specification |

$^a$G4S: Amino acid sequence of GGGGS (SEQ ID No: 4);
$^b$(His)6: six Histidine tag; and
$^c$B: Domain B of *Staphylococcus aureus* Protein A.

Repeat-chain proteins were overexpressed using previously described method (J. H. Park, et al., Mol Cells 12 (2001) 398-402).

The crude cell lysate was subjected to Ni2+-chelating Sepharose fast flow chromatography (Amersham Bioscience, Sweden). The eluted protein was subjected to Hiload Superdex-75 pg or Hiload Superdex-200 pg(26/60)(Amersham Bioscience, Sweden), and purified.

<Example 12> Expression Plasmid Construction for Repeat-Chain Protein of Antibody Binding Domain B1 of *Peptostreptococcus Magnus* Protein L The plasmid that contains the DNA sequence of Protein L Domain B1 was synthesized (table 6) and obtained from the Bioneer Corporation. The plasmid was put into *Escherichia coli* DH5a by transformation.

The plasmid was digested with NdeI and BspEI and the small DNA fragment (299 bp) was purified. The samll fragment was cloned into the vector fragment of pGR1 (pTR1) obtained by same enzyme digestion, and the plasmid pLR1 that contains one copy of domain B1 of protein L was obtained. Protein L Domain B1 Nucleic acid sequence was checked by sequencing analysis of Macrogen corporation The resulting plasmid, pLR1 (table 7) was digested with NdeI and BspEI. The small 299 bp fragment, encoding domain B1 and two of five amino acid GGGGS (G4S; SEQ ID NO:4) sequence, was ligated with the large fragment of NdeI and AgeI digested pLR1. The resulting plasmid, pLR2, contains two repeat of Protein L Domain B1. pLR2 was digested with NdeI and AgeI again, and the large fragment was ligated with the 299 bp fragment to produce a new plasmid, pLR3, that has three time repeat of domain B1. Using the same method, plasmids coding up to five repeats of protein L domain B1 (pLR5) were constructed.

TABLE 6

Nucleic acid sequence of Protein L Domain B1

Nucleic acid sequence of Protein L Domain B1

(SEQ ID No: 5)
5'-CAT<u>ATGCATCACCATCACCATCATACCGGTATCAAGTTCGCCGG</u>

<u>TAAAGAAGAAACGCCGGAAACCCCTGAGACAGACAGTGAAGAGGAAG</u>

<u>TGACAATAAAAGCAAATCTGATTTTCGCCAACGGGTCAACCCAGACG</u>

<u>GCCGAATTCAAAGGGACATTTGAAAAAGCAACTTCTGAGGCTTATGC</u>

<u>ATACGCGGACACTCTGAAGAAGGATAATGGTGAATATACCGTAGATG</u>

TABLE 6-continued

Nucleic acid sequence of Protein L Domain B1

Nucleic acid sequence of Protein L Domain B1

<u>TTGCTGATAAAGGTTATACCCTGAATATTAAATTTGCGGGTGGCGGC</u>

<u>GGCGGAAGCGGTGGCGGAGGTTCCGGATAAG</u>AATTC-3'

*under line: coding sequence

TABLE 7

List of plasmids and proteins

| Plamid | Repeat-chain protien | Reference |
|---|---|---|
| pLR1~5 | LR1~5: $(His)_6$-$(B1$-$G_4S$-$G_4S)_n$, $n = 1$~$5.^{a,\ b,\ c.}$ | This specification |

$^a$G4S: Amino acid sequence of GGGGS (SEQ ID No: 4);
$^b$(His)6: six Histidine tag; and
$^c$B1: Domain B1 of *Peptostreptococcus magnus* Protein L.

Repeat-chain proteins were overexpressed using previously described method (J. H. Park, et al., Mol Cells 12 (2001) 398-402).

The crude cell lysate was subjected to Ni2+-chelating Sepharose fast flow chromatography (Amersham Bioscience, Sweden). The eluted protein was subjected to Hiload Superdex-75 pg or Hiload Superdex-200 pg (26/60) (Amersham Bioscience, Sweden), and purified.

<Example 13> Expression Plasmid Construction for Repeat-Chain Protein of Antibody Binding Domain B1 of *Peptostreptococcus* Magnus Protein L and Antibody Binding Domain B of *Staphylococcus aureus* Protein A The plasmid that contains the DNA sequence of Protein L Domain B1 was synthesized and used to construct pLR1.

The plasmid pLR1 was digested with NdeI and BspEI and the small DNA fragment (299 bp) was purified. The samll fragment was cloned into the vector fragment of pAR1 obtained by same enzyme digestion, and the plasmid pLAR1 that contains one copy of domain B1 of protein L connected to one copy of domain B of protein A (B1-B) was obtained. The nucleic acid sequence was checked by sequencing analysis of Macrogen corporation.

The resulting plasmid, pLAR1 (table 8) was digested with NdeI and BspEI. The small 521 bp fragment, encoding domain B1-B and two of five amino acid GGGGS (G4S; SEQ ID NO:4) sequence between domains, was ligated with the large fragment of NdeI and AgeI digested pLAR1. The resulting plasmid, pLAR2, contains two repeat of B1-B. pLAR2 was digested with NdeI and AgeI again, and the large fragment was ligated with the 521 bp fragment to produce a new plasmid, pLAR3, that has three time repeat of domain B1-B. Using the same method, plasmids coding up to three repeats of protein L domain B1 and protein A domain B (B1-B) (pLAR3) were constructed.

TABLE 8

| Nucleic acid sequence of Domain B1-Domain B |
| --- |
| Nucleic acid sequence of Domain B1-Domain B |
| (SEQ ID No: 6)<br>5'-CATATGCATCACCATCACCATCATACCGGTATCAAGTTCGCCGG<br>TAAAGAAGAAACGCCGGAAACCCCTGAGACAGACAGTGAAGAGGAAG<br>TGACAATAAAAGCAAATCTGATTTTCGCCAACGGGTCAACCCAGACG<br>GCCGAATTCAAAGGGACATTTGAAAAAGCAACTTCTGAGGCTTATGC<br>ATACGCGGACACTCTGAAGAAGGATAATGGTGAATATACCGTAGATG<br>TTGCTGATAAAGGTTATACCCTGAATATTAAATTTGCGGGTGGCGGC<br>GGCGGAAGCGGTGGCGGAGGTTCCGGTTCTCAAGCCCCAAAAGCCGA<br>CAATAAATTTAATAAAGAGCAGCAGAACGCGTTTTATGAAATCTTGC<br>ATCTGCCGAATCTGAATGAAGAACAACGTAACGGATTCATTCAGAGC<br>CTTAAAGATGATCCTAGTCAGTCCGCTAACTTACTCGCAGAAGCTAA<br>GAAACTGAATGATGCACAGGCGCCGAAGGGAGGGGGTGGATCCGGTG<br>GTGGCGGCTCCGGATAAGAATTC-3' |

*under line: coding sequence

TABLE 9

| List of plasmids and proteins | | |
| --- | --- | --- |
| Plamid | Repeat-chain protien | Reference |
| pLAR1~3 | LAR1~3: $(His)_6$-$(B1\text{-}G_4S\text{-}G_4S\text{-}B\text{-}G_4S\text{-}G_4S)_n$, $n$ = 1~3.[a,b,c,d] | This specification |

[a]G4: Amino acid sequence of GGGG (SEQ ID No: 7);
[b](His)6: six Histidine tag;
[c]B1: *Peptostreptococcus magnus* Protein L Domain B1; and
[d]B: *Staphylococcal aureus* Protein A Domain B.

Repeat-chain proteins were overexpressed using previously described method (J. H. Park, et al., Mol Cells 12 (2001) 398-402).

The crude lysate was subjected to Ni2+-chelating Sepharose fast flow chromatography (Amersham Bioscience, Sweden). The eluted protein was subjected to Hiload Superdex-75 pg or Hiload Superdex-200 pg (26/60)(Amersham Bioscience, Sweden), and purified.

<Example 14> Cross Binding of Gold Antibody/Repeat-Chain Complex or Super-Complex to Test Line Antibody of Rapid Antigen Test Kit The cross-bindings of the gold antibody/repeat-chain complexes or super-complexes to the detection line antibody on influenza rapid antigen test kit strip were tested without adding virus antigens. This cross-binding without the antigen is brought by the binding of empty immunoglobulin binding domain of the repeat-chain in the repeat-chain/gold antibody complex or super-complexes to the antibodies of the test line fixed on the strip. We used SD influenza A/B rapid test kit and Green cross influenza A/B rapid test kit. They consist of test strip, assay buffer, disposable droppers and disposable swab. Assay buffer was transferred into a test tube, and the GR, AR, LR, LAR series proteins were added into the test tube. The tube was swirled at least five times to mix. The test strip was placed into the test tube with the arrows mark on the test strip pointing down and read result after 10~15 min.

The cross binding was detected by GR4, GR5, GR7GR10, GR15GR20. The protein amounts of the repeat-chain used were 10 μg, 1 μg and 0.1 μg for SD strips. The bands of Green cross strips were clearer than SD strips. There was no band detected at 0.1 μg of repeat-chain (FIG. 18). AR5, LR3, LR5, LAR1, LAR2, LAR3 also gave cross binding band on SD strip. But Green Cross strip did not give any band with LR series protein. Protein L binds only to kappa light chain and it indicated that the antibody used on Green Cross strip was not kappa light chain. All of AR, LR, LAR proteins did not give cross binding bands at below 0.1 μg (FIG. 19).

<Example 15> The Signal Amplification by Repeat-Chains on Influenza Rapid Antigen Test Kit Rapid Antigen Test is the typical diagnosis technique using antibody as detection probe. The amplifications of the signal effect of Influenza Rapid Antigen Test Kit by repeat chain GR, AR, LR and LAR series repeat-chains were tested. We used SD influenza A/B rapid test kit and Green cross influenza A/B rapid test kit. We used same procedure as previously described example. The amounts of GR, AR, LR, LAR proteins used are indicated in each figure. The virus antigen samples were added in 10-fold serial dilutions.

For GR5, the antigen band could be detected until the antigen was 10^−8 fold diluted. (FIG. 20)

For GR10, the antigen band could be detected until the antigen was 10^−8 fold diluted. (FIG. 21)

For GR15, the antigen band could be detected until the antigen was 10^−9 fold diluted. (FIG. 22)

For GR20, the antigen band could be detected until the antigen was 10^−9 fold diluted. (FIG. 23)

For AR5, there was no amplification of the signal detected. (FIG. 24)

For LR5, the antigen band could be detected until the antigen was 10^−6 fold diluted. (FIG. 25)

For LAR3, the antigen band could be detected until the antigen was 10^−8 fold diluted. (FIG. 26)

<Example 16> Observation of Supercomplex Precipitation Between Repeat-Chain GR, AR, LR, LAR and IgG IgG solution was made by solving IgG powder of Equitech Bio, in PBS. The IgG solution was placed on rocker for 2 hours, and then powder which wasn't solved completely in the solution was removed by centrifugation for 21000 rpm, 2 hours at 4° C. GR1~20 and IgG solutions were used after quantitative analysis by Bicinchoninic Acid protein assay, and diluted to proper concentrations. The GR1~20 solutions are mixed with IgG solution in micro-centrifuge tubes and incubated at room temperature overnight. After the incubation, the precipitation was collected by centrifuge at 13000 rpm for 30 minutes at 20° C. If precipitation was formed, it could be observed with bare eyes at this point. Supernatant was removed and placed a clear new tube by using micro-pipets, and then 500 μl of 75% ethanol was added to the tube and removed to wash out remaining solutions which could be on the inner surface of the tube. After evaporating remaining ethanol completely the pellet was put on SDS-PAGE. The results showed that when IgG was mixed with GR10 in molar ratios of 1:1, 5:1 and 10:1, one in 5:1 ratio had more precipitation than others (FIG. 27).

IgG and GR10 were mixed in 5:1 molar ratio, and same amounts of GR1 & 2 in gram were mixed with IgG and incubated. More precipitation and pellet protein bands on a SDS-PAGE gel were observed with GR10 than GR1 or GR2 (FIG. 28). When GR proteins exist in same gram amounts, the total amounts of binding domains are the same, but in GR10, the ten domains are linked to form a single repeat-chain. When the domains are linked to form a longer repeat-chain, it is able to form super-complex much better.

IgG and GR10 were mixed in 5:1 molar ratio, and same amounts of GR1~9 in gram were mixed with IgG and incubated. The final concentration of IgG was 400n/ml. Precipitation which could be observed with bare eyes (FIG. 29) and pellet IgG bands on a SDS-PAGE gel (FIG. 30) could be seen from GR3 to GR10. This results showed that the precipitatible super-complex by cross-linking between complexes can be formed from GR3 that has three D(III) domains and one GGGGS (SEQ ID NO:4) linker between the domains in it.

IgG only control sample and BSA in place of GR control sample did not give precipitation. This indicated that precipitation did not formed because the addition of other protein in the solution caused the decrease of solubility of IgG protein, but precipitations were formed by the addition of the repeat chain which can cross-bind the complexes forming super-complex of heavy molecular weight.

To see whether GRs bigger than GR10 can make super-complex with IgG, IgG and GR10 were mixed in 5:1 ratio, and GR1, 3, 5, 15 and 20 were tested in the same way as above. Precipitation was observed in all samples except IgG+GR1 and IgG only samples. The SDS-PAGE results showed precipitation were formed from GR3 to GR20 (FIG. 31). GRs bigger than GR10 like GR15 or 20 can also form precipitatible super-complex.

When the final concentrations of IgG were decreased serially and tested in the same way, there were no precipitations below 25 μg/ml of IgG. These results indicated that precipitatible super-complex formation of GR with IgG was dependent on concentration of IgG.

Using the same procedure, AR1, 3, 5, LR1, 3, 5 and LAR1, 2, 3 were incubated with IgG. The concentration of IgG of 500 μg/ml was used. Precipitations couldn't be observed for AR, LR and LAR repeat-chain proteins. These repeat-chain proteins could not make precipitatible insoluble super-complex.

<Example 17> The Increase of Antibody Signal in Enzyme-Linked Immunosorbent Assay (ELISA) by GR10, GR20, AR5, LR5, LAR3

The procedures used are same as in the example 16.
The signal intensities were increased by GR10, GR20, LR5, LAR3, but not by AR5(Table 10).

TABLE 10

The increase of antibody signal in enzyme-linked immunosorbent assay (ELISA) by GR10, GR20, AR5, LR5, LAR3.

| Sample | A450 nm value | Fold Increase |
| --- | --- | --- |
| IgG + (No repeat chain) | 0.79 | 1.0 |
| IgG + GR10 | 2.49 | 3.2 |
| IgG + GR20 | 2.43 | 3.1 |
| IgG + AR5 | 0.89 | 1.1 |
| IgG + LR5 | 1.07 | 1.4 |
| IgG + LAR3 | 1.09 | 1.4 |

INDUSTRIAL APPLICABILITY

The present invention relates to formation of multimers formed by bond bridges. With repeat-chains of affinity domains having specific binding affinity, the formation of a repeat-chain/multiple-monomer complex can be achieved, and thus a formed repeat-chain/multiple-monomer complex can be used to produce multimers linked by bond bridges. Remarkably high formation rate is provided by a method of the present invention and leads to formation of dimers linking with bond bridges in mass quantity; therefore, the present invention is industrially applicable.

Monomers can also be made with many kinds of substances including ligand, or a part fragment of the ligand having binding affinity such as TGF alpha, TGF beta, IL2, IL6, TNF or GMSCF, and various kinds of ligand receptors or a part fragment of ligand receptors having binding affinity such as TBP1, TBP2, IFN alpha or beta, or gonadotropin receptors. (Nienhaus, G. Ulrich. Protein-ligand interactions: methods and applications. Humana Press, 2005).

In addition, The followings may be used to form monomers: various kinds of enzymes catalyzing prodrugs transformation or detection, decomposition and formation of substance, proteins including functional group of cytotoxic toxin, organisms such as virus for gene therapy, cation tail compounds for DNA delivery, liposome produced by chemical engineering method for delivery of drug, biosensor for real-time detection of target molecule, or prodrug, or other functional groups.

In nature, there are various kinds of substances having binding affinity relationship to each other. Ligands and acceptors, antibody and antigen, homodimer, heterodimer, or proteins forming multimers are the known substances. By using these substances having inter-binding-affinity as monomers and affinity domains, multimers linked with bond bridges may be prepared in large quantity from monomers based on a method of the present invention.

In the present invention, the repeat-chains having specific binding affinity are characterized to form a repeat-chain/multiple-monomer complex. Therefore, as fixing the repeat-chains on resin, it is possible to perform affinity purification with high efficiency for the purification of useful protein molecules in monomeric or multimeric form in biotechnology and medical industry (Zachariou M., Affinity Chromatography: Methods and Protocols (Methods in Molecular Biology) Humana Press; 2nd edition).

The present invention relates to a super-complex prepared by cross-binding between repeat-chain/monomer complexes, and a method for amplifying the effect of monomer through the formation of the said super-complex. Particularly, the repeat-chain/monomer complex is prepared by containing repeat-chains of binding domain having binding specificity to monomers as active ingredients, and then the super-complex is prepared by cross-binding between such complexes. Since the super-complex contains multiple monomers, the biological and chemical effect becomes very strong, based on which the present invention provides a method for amplifying the effect of monomer including signal amplification, etc.

In this invention, multiple monomers and repeat-chains are bound to each other to form a complex. By cross-binding between such complexes, an insoluble super-complex can be generated at high concentration, which gives precipitations. Aggregation, precipitation, and size of the super-complex depend on the structures of monomer and repeat-chain. The number of repeat in the binding domain affects the cross-binding between complexes. Water-solubility and molecular size of the monomer affect the chance of cross-binding. The said super-complex demonstrates multiple biological and chemical effect on target of the monomer since it contains multiple monomers therein. Therefore, it can be effectively used for the amplifications of detection signal, reaction effect, and therapeutic treatment effect, etc.

What is claimed is:

1. A method for preparing a super-complex, comprising the following steps:
   (a) preparing a repeat-chain protein comprising at least one linker and at least three or more copies of immunoglobulin binding domain wherein the at least three or more copies of the immunoglobulin binding domain is:
   domain III of protein G encoded by a DNA sequence obtained from the primers of SEQ ID NO: 1 and SEQ ID NO: 11,
   domain B of protein A encoded by SEQ ID NO:3,
   domain B1 of protein L encoded by SEQ ID NO:5, and/or
   domain B1 of protein L and domain B of protein A encoded by SEQ ID NO:6; and
   (b) mixing or contacting the repeat chain of step (a) with an antibody monomer with or without antigen to form super-complex by inter-complex cross-binding that is formed by the antibody binding two repeat-chain, wherein the antibody monomer has at least two binding sites that bind to the repeat-chain protein.

2. The method as set forth in claim 1, wherein the antibody monomer is a whole antibody, an antibody fragment, or the antibody monomer is fused to a biological or chemical compound selected from the group consisting of an enzyme and toxin.

3. The method as set forth in claim 2, wherein the antibody monomer is selected from the group consisting of a whole antibody, a Fab fragment, a Fv fragment and a Fc fragment and fragment containing a Fab fragment, fragment containing a Fv fragment, and fragment containing a Fc fragment, wherein the antibody monomer comprises at least two independent binding sites to the repeat-chain protein.

4. The method as set forth in claim 1, wherein the domain III of protein G is from *Streptococcus*, the domain B of protein A is from *Staphylococcus aureus*, and the domain B1 of protein L is from *Peptostreptococcus* magnus.

5. A method for preparing a super-complex comprising the following steps:
   (a) preparing a repeat-chain-detection functional group by linking, conjugating, or fusing a detection functional group to a repeat-chain protein comprising at least one linker and at least three or more copies of immunoglobulin binding domain wherein the at least three or more copies of the immunoglobulin binding domain is:
   domain III of protein G encoded by a DNA sequence obtained from the primers of SEQ ID NO: 1 and SEQ ID NO: 11,
   domain B of protein A encoded by SEQ ID NO:3,
   domain B1 of protein L encoded by SEQ ID NO:5, and/or
   domain B1 of protein L and domain B of protein A encoded by SEQ ID NO:6; and
   (b) mixing the repeat-chain-detection functional group of step (a) with an antibody monomer with or without an antigen to form super-complex by inter-complex cross-binding that is formed by the antibody binding two repeat-chain, wherein the antibody monomer has at least two binding sites that bind to the repeat-chain protein.

6. The method as set forth in claim 5, wherein the detection functional group is selected from the group consisting of Cy-3, Cy-5, FITC, GFP (green fluorescent protein), RFP (red fluorescent protein), Texas Red, colloid gold, fluorescein, Quantum dot, radio-isotope, and dye.

* * * * *